United States Patent
Dharmarajan

(10) Patent No.: US 12,419,829 B2
(45) Date of Patent: Sep. 23, 2025

(54) TOPICAL PRODUCT HANDS-FREE APPLICATOR DRUG DELIVERY SYSTEM AND METHODS OF MAKING AND USING THE SAME

(71) Applicant: Annadurai Dharmarajan, Morrisville, NC (US)

(72) Inventor: Annadurai Dharmarajan, Morrisville, NC (US)

(*) Notice: Subject to any disclaimer, the term of this patent is extended or adjusted under 35 U.S.C. 154(b) by 122 days.

(21) Appl. No.: 17/885,163

(22) Filed: Aug. 10, 2022

(65) Prior Publication Data
US 2024/0050361 A1 Feb. 15, 2024

(51) Int. Cl.
A61K 9/00 (2006.01)
A61K 9/70 (2006.01)
A61M 35/00 (2006.01)
A61K 31/167 (2006.01)

(52) U.S. Cl.
CPC .......... *A61K 9/0014* (2013.01); *A61K 9/7092* (2013.01); *A61M 35/006* (2013.01); *A61K 31/167* (2013.01)

(58) Field of Classification Search
CPC .. A61K 9/0014; A61K 9/7092; A61K 31/167; A61M 35/006
See application file for complete search history.

(56) References Cited

U.S. PATENT DOCUMENTS

| | | | | |
|---|---|---|---|---|
| 3,949,746 A | * | 4/1976 | Wallach | A61M 5/20 604/152 |
| 2001/0033766 A1 | * | 10/2001 | Gueret | A45D 34/046 401/121 |
| 2002/0039591 A1 | * | 4/2002 | Dahle | A61Q 17/04 424/401 |
| 2002/0076256 A1 | * | 6/2002 | Gueret | A45D 33/00 401/126 |
| 2006/0189968 A1 | | 8/2006 | Howlett et al. | |
| 2009/0216204 A1 | * | 8/2009 | Bhavaraju | A61F 13/05 604/290 |
| 2020/0214425 A1 | * | 7/2020 | Thorpe | A61M 35/003 |
| 2020/0268681 A1 | | 8/2020 | Kochinke | |
| 2021/0369153 A1 | | 12/2021 | Heikenfeld et al. | |

FOREIGN PATENT DOCUMENTS

| | | | | |
|---|---|---|---|---|
| CN | 102824016 A | * | 12/2012 | ............ A45D 34/04 |
| KR | 20140110263 A | * | 9/2014 | |
| KR | 20140115097 A | * | 9/2014 | |
| KR | 200477997 Y1 | * | 8/2015 | |

OTHER PUBLICATIONS

International Search Report.
PCT Written Opinion.

* cited by examiner

*Primary Examiner* — Bob Zadeh
(74) *Attorney, Agent, or Firm* — Ashley D. Johnson; Dogwood Patent and Trademark Law

(57) ABSTRACT

The invention is directed to a method of treating one or more topical diseases and enhancing patient compliance using a topical drug delivery system, applicator, composition and adhesive bandage pod (APPOD™).

19 Claims, 19 Drawing Sheets

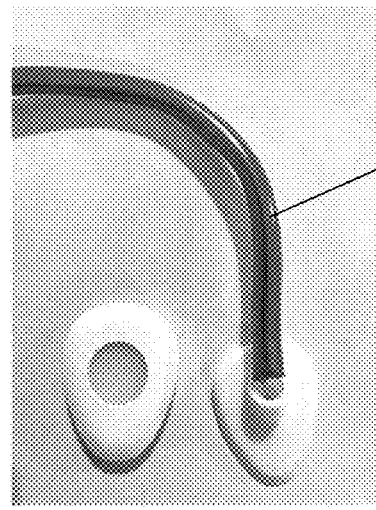 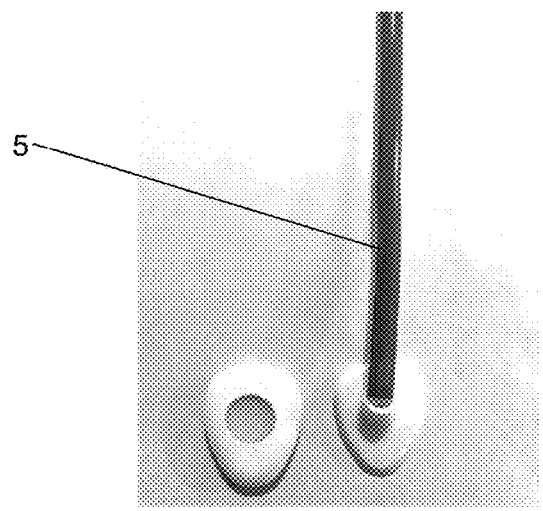
Fig. 4a    Fig. 4b
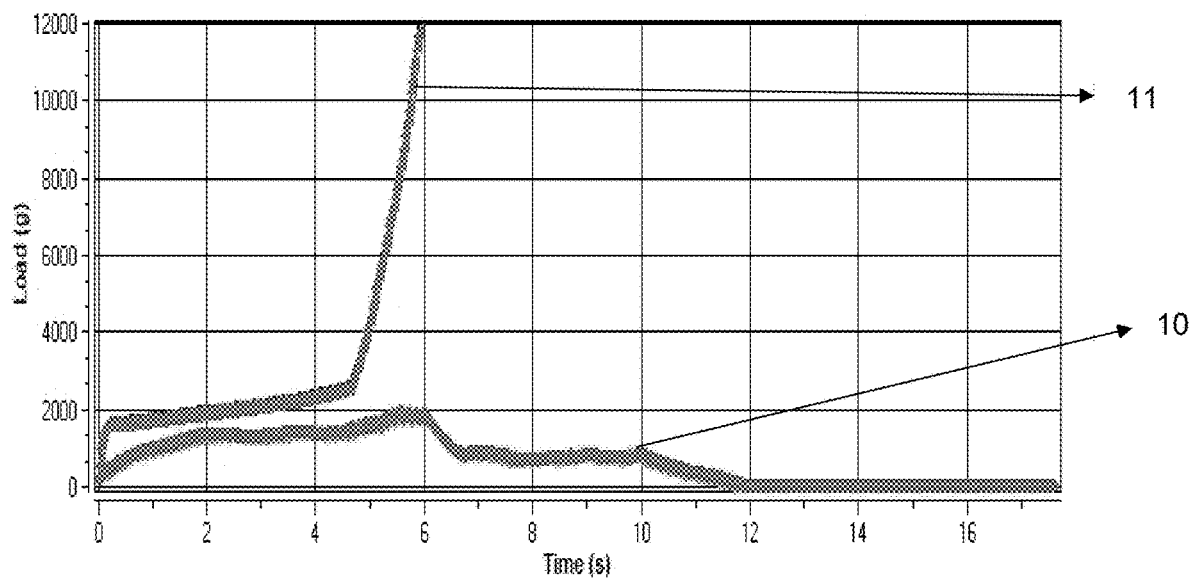
Fig. 5

TOPICAL PRODUCT HANDS-FREE APPLICATOR DRUG DELIVERY SYSTEM AND METHODS OF MAKING AND USING THE SAME

TECHNICAL FIELD

The presently disclosed subject matter is generally directed to a topical product hands-free applicator drug delivery system, and to methods of making and using the disclosed system. Topical dosage forms that administer drugs to the skin are traditionally constituted in the form of creams (oil in-water & water-in-oil type based), gels (aqueous & hydro-alcohol based), ointments (hydrocarbon & polyethylene glycol based) or pastes and transdermal films. These marketed topical preparation requires to take it in hand and apply to the affected areas of skin, part of topical product will be sticking to the hand and there is no exact quantity of drug can be taken from an ointment or cream products and when applied, the drug will take time to dissolve and separate from the greasy inactive ingredients that are purposely included so that the ointment can stick to the skin surface and final step after separation of the drug from the excipients, the drug will take the moisture from the skin and dissolve and finally penetrate through the skin for its action, and after applying the greasy nature of the ointment will stick to the dress. The invention relates to topical formulation compositions and device includes hands-free applicator along with appod that will enhance patient compliance and efficacy for the topical product administration.

BACKGROUND

The skin is a complex multilayered structure extending over an area of 1.5 to 2 $m^2$ in adults. Its primary role is to act as a barrier between the body and the relatively hostile external environment. The stratum corneum is a highly structured lipid-rich region that minimizes the ingress and egress of water, oxygen, and chemicals. Topical drug delivery system is for local delivery of agents, particularly those which have toxic effects if administered systemically, used to treat most dermatologic sickness and avoid first pass metabolism. Delivery of topical drug delivery is challenging, due to the constraint of the stratum corneum the drug must be on hold in the skin for a long time to be absorbed through the skin, the currently marketed topical drugs are in ointment and creams that can hold the drug for longer time to the skin. Adherence to topical treatment has been found challenging, application of topical medications is often considered and reported by the patients as being more difficult than simply taking a pill (20), [61,62]. Patient, treatment, and disease factors have been appointed to justify poor adherence. Regarding treatment, poor acceptability of the topical vehicles (in ointment and creams) properties as very greasy, desiccating, or sticky vehicles and the smell of the preparation and staining of clothes, time required for its application have been reported by patients with chronic skin disorders as barriers to optimal treatment adherence. It is therefore not surprising that patients commonly consider topical treatment as unpleasant and time consuming and are commonly reporting their non-adherence to the recommended treatment [5].

U.S. Pat. No. 3,616,970 to Baumann adds a closed exit end with an exit hole or holes, making it suitable for liquids and gels. U.S. Pat. No. 4,139,127 adds a ratchet mechanism to prevent repel motion, making it a propel dispenser only. U.S. Pat. No. 1,568,178 to Noble shows a configuration in which the drive screw is disposed entirely outside of the product reservoir. U.S. Pat. Nos. 5,851,079, 7,751,934 to Konietzko and U.S. Pat. No. 5,397,178 to Konietzko, discloses a one-way ratchet mechanism as well that are tied to metered incremental doses for compounding liquids, creams, and gels for pharmaceutical formulations.

U.S. Pat. Nos. 7,213,994 and 7,303,348 to Phipps, et al, and U.S. Pat. No. 8,544,684 to Perez. These are propel/repel containers of conventional construction with the additions of an indexed dose metering capability, These are commercially available as the Topi-CLICK™ from DoseLogix. The above inventions are providing the metered doses for topical product that are compounder in pharmacies, but it is not addressing the applying without rubbing the product and patient convenience and compliance for once-a-day application.

U.S. Pat. No. 7,241,065—Tuffs, et al. enables an applicator for coloring antiseptic.

Tuffs teaches body and porous plug does not teach or suggest an applicator with an integral handle and dosing end.

U.S. Pat. No. 5,112,297—Stalcup, et al. enables a topical anesthetic applicator, dispenser system, and method. In part, Column 2 reads, "Referring now to FIG. 1, a preferred embodiment of the applicator 20 for topical anesthetics is illustrated. The preferred embodiment is discussed in the context of dental applications, although it is to be understood that the invention has utility generally to apply topical anesthetics to mucosal tissue. Thus, other medical applications exist to apply anesthetic to such exemplary areas as the mucosal tissue in the nose.

U.S. Pat. No. 6,364,862—Bonilla enables a single pad for providing both an anesthetic and an antiseptic for an injection site. Bonilla teaches a pad capable of applying at least two chemical compositions. However, the '862 patent does not teach a shaft, a bulbous member, a topical anesthetic carried by a first segment of the dosing end of the bulbous member and a second segment of the bulbous member carrying temporary marker circumscribed by the first segment, wherein upon contact with tissue.

U.S. Pat. No. 7,008,392—Beaudry enables a hemostatic cleansing swab.

Wound treating element 20 is secured to stick 12 at its distal portion 16. Wound treating element 20 comprises a wound cleaning element 22 and a hemostat-containing element 24. In the embodiment under discussion, and as seen in FIGS. 3 and 4 of the drawings, wound cleansing element 22 is in the shape of a tear-drop and is attached over distal end 17 of stick 12 and continued downwardly over the upper part of distal portion 16. Wound cleansing element 22 may be secured to the outer surface of stick 12 by frictional engagement; alternatively, an adhesive (not shown in the drawings) may be used for this purpose.

U.S. Pat. No. 3,179,108—Bloch enables an applicator. In part, Column 3 reads, "The swab comprises a thin-walled hollow thermoplastic stick 16 and a wad 17 of absorbent fibrous material secured to each end of the stick."

U.S. Pat. No. 3,508,547—Deuschle enables an applicator swab. In part, Column 2 reads, "The applicator 10 of this invention includes a handle portion 12, preferably a thin elongate member of substantially rigid plastic, or the like. One end of the handle is provided with an opening 14 which preferably is of an irregular shape, such as the generally trapezoidal shape illustrated . . . . A swab portion 16, preferably of an expanded foam polyurethane or similar sponge-like material, is attached to the end of the handle 12 in the area of opening 14."

U.S. Pat. No. 3,757,782—Aiken enables a fluid pressurizable swab applicator for medicament, antiseptic or the like. In part, Column 2 reads, A first version of the applicator, generally designated by the reference number 10, is shown in FIGS. 1 and 1 and comprising an axially elongated tubular applicator handle rod 12 of relatively small diameter . . . the material must be chemically inert to the treatment liquid, represented by a charge 14 of antiseptic or medicament contained in tube member 12. The charge substantially fills the interior of said member between extreme opposite ends.

U.S. Pat. No. 3,876,314—Nehring enables a pre-filled applicator or scrubber. In part, Column 3 reads, "Referring first to FIG. 1 the applicator generally indicated at 10 is shown as comprising a tubular handle 12 preferably made of a semi-rigid plastic material, such as a medium density polyethylene, extruded or molded. The thickness of the wall of the handle 12 should be such as to afford sufficient rigidity for use as a handle to apply a required amount of pressure to a surface being treated while at the same time to permit squeezing of the handle to force liquid contained therein into the applicator head from time to time as required. With the polyethylene material just referred to, a wall thickness of about 30 mils (0.030 inch) will be adequate for accomplishment of both of these purposes, when the applicator is to be used, for example, as a surgical skin scrubber where vigorous action and relatively high rubbing pressures are involved. Other plastic materials such as polyamides (nylon) or polyvinyl chlorides also may be used. Wall thickness in all cases may be chosen for various intended uses and thinner walls are chosen when scrubbing or high pressures are not required."

U.S. Pat. No. 4,173,978—Brown enables a self-contained antiseptic applicator swab. In part, Column 2 reads, "A foam tip 46, as seen in FIGS. 6 and 7, is preferably of a two pound density polyester foam and is provided with an adhesive strip 48 that is adhesive both on the front and back and is porous so that the antiseptic liquid 32 can penetrate therethrough when the glass ampoule 30 is crushed and the antiseptic liquid flows through the channel 42 in the blister package and into the foam tip 46. The adhesive is of the type known as Micropore adhesive, a registered trademark of the 3M Company, and will not lose its adhesiveness when exposed to the alcohol present in the antiseptic."

U.S. Pat. No. 4,740,194—Barabino, et al. enables a self-contained liquid swab applicator and method for its manufacture. In part, Column 3 reads, "Referring now to the drawings there is shown in FIG. 1 a self-containing liquid swab applicator 10 constructed of a hollow flexible plastic material and forming a supply liquid-containing shaft or tubing 12 and shown prepared for use. Sealed ends 14, 16 are sealed and upon removal of an adhesive tape or tab 18, the liquid 22 gravitates through an exit orifice 20 to saturate an outer surface of an adsorbent material 24 forming a swab 66, an open cell foam material or cotton form having a good quality of wickability or one that is found to permit wicking of the supply liquid that thoroughly saturates the outer surface thereof."

U.S. Pat. No. 4,887,994—Bedford enables applicator swabs and method of making same. In part, Columns 2 and 3 read, "When impregnated with an antibacterial or disinfectant fluid, the applicator swabs of the present invention are advantageously packaged in a fluid-impervious package or pouch 31. The pouch is sealed at its periphery to completely encase the plurality of applicator swabs 35, 37 and 39 contained therein. The pouch provides a disinfected environment for storage of the swabs 35, 37 and 39. The pouch may be opened by tearing along a tear line 33, for example, or by utilizing any other convenient opening device. The package 31 is preferably made of an aluminum foil material that is well known for this use. Each of the applicators 35, 37 and 39 stored within the pouch 31 may contain an anti-germicide or disinfectant solution 41, or any other solution that can be conveniently applied by a swab applicator of the type illustrated herein. Besides the solution contained within the open-cell foam applicators 35, 37 and 39, a certain amount of the solution might be found in the bottom of the pouch. This type of disinfected packaging of the applicator swabs is designed to encourage the swabs to be thrown away."

U.S. Pat. No. 5,762,494—Archambault enables an applicator device and method. In part, Column 4 reads, "The anesthetic delivery member 10 is a member formed of material which can retain and deliver an amount of anesthetic suitable for use in the mouth, such as lidocaine. Preferably the delivery member 10 is pre-dosed with a measured amount of anesthetic and packaged in suitable material to create a relatively long shelf life, the package being opened at the time of use, but the device could also be used where the anesthetic is applied to the delivery member 10 from a common container or source. The delivery member 10 may be composed of any suitable material capable of retaining and delivering the anesthetic and of being fixedly attached to a second retention means 30, such as spun or woven cotton or other natural or synthetic fibers, polymer or natural foam or sponge material, or polymer-based gels or matrices. The delivery member 10 may be shaped in various configurations such as round, oval, square or rectangular, and can be spheroid or relatively flat. Preferably the delivery member 10 is generally round or ovoid to better match the curve of the alveolar mucosa area. Such delivery members 10 are well known in the art."

U.S. Pat. No. 5,919,152—Zygmont enables antibacterial swabs. In part, Column 2 reads, "Swabs, especially cotton swabs can be rendered less susceptible to microbial contamination by impregnating antibacterial agents onto cotton or other absorbent coverings surrounding ends of the swab.

U.S. Pat. No. 6,623,440—Weldon enables a topical applicator and method of use. In part, Column 2 reads, "To perform the method, the physician first dips the absorbent means of the applicator into topical anesthetic. The physician then lightly abrades the desired oral site with the abrasive means, followed immediately by applying the absorbent means containing the topical anesthetic to the abraded mucosal area. The application of the topical anesthetic is followed by an injection given by an injection device in which the depth of the injection is automatically limited to penetrate only into the area anesthetized by the topical. As a result, the patient experiences greatly reduced discomfort and pain."

US Published patent application No. 20050261639—Herwick discloses a medicated ink marker with the porous applicator. The Herwick Application discloses that drugs can be carried by ink marker 60. However, among other things, the '639 Application does not teach or suggest a bulbous member, a topical anesthetic carried by a first segment of the dosing end of the bulbous member and a second segment of the bulbous member carrying temporary marker circumscribed by the first segment, wherein upon contact with tissue, the topical anesthetic and temporary marker are released onto a zone of the tissue.

US Published patent application No. 20060211978—Do discloses a method for treatment of skin diseases and the like. Paragraph 18 reads, "As shown in FIG. 2, the pharmacological active agent can also be applied as a layer 16 on the swab 14 at the end of the applicator 10. The layer 16 can be on the surface only, diffused somewhat into the swab material, or completely diffused throughout the swab. The pharmacological agent can be mixed homogenously throughout the swab or can be fixed within or on the swab material on the applicator, so long as they can be dispersed after hydration onto the skin." U.S. Published patent application Ser. No. 10/814,114—Boyajian Thomas discloses a method an applicator for dispensing a solution having two or more components includes a hollow body having a head provided at one end of the hollow body for dispersion of the solution and a breaking mechanism attached to the hollow body that uses ampoules for topical application.

20200297654, Marchant; Nancy S.; et al. A transdermal delivery device comprising: at least one of a backing layer and a removable release liner; an active layer supported by the at least one of the backing layer and the removable release liner, the active layer comprising: a polymer matrix, a therapeutically or cosmetically effective amount of an active agent dispersed in the polymer matrix, and a pressure sensitive adhesive, the pressure sensitive adhesive being least one of: incorporated in the polymer matrix, and adhered to the polymer matrix.

20170291020, TOLIA; Gaurav Thakersi; et al. A dermal device for administration of one or more active agents to the skin or mucosa comprising: an active inner disk comprising: an active inner reservoir layer comprising, an active adhesive layer; and a film layer adjacent to the active adhesive layer.

20130337032, SHUDO; JUTARO Topical patch preparations that contain an odorless physiological cooling agent, and methods for using the same are provided. The subject topical patch preparations are made up of an adhesive gel composition that is present on a support, where the adhesive gel composition includes the odorless physiological cooling agent, a water-soluble polymer gel, water and a water holding agent.

20120135225, Colas; Andre et al. This invention pertains to a construction including in the order from the outside towards the inside: An occlusive or non-occlusive external film layer; a non-curing pressure sensitive adhesive (PSA) that has been blended with a therapeutic concentration of at least one or a combination of cosmetic or pharmaceutical active ingredients.

U.S. patent Ser. No. 11/178,952; Abadilla An applicator used for evenly spreading a cream from a tube to which the applicator is attached. The applicator has a base unit that fits over the opening in the tube of cream and directs the cream through a hole in applicator unit, which is the upper part of the invention. The applicator unit has a spreader, which evenly distributes the cream onto a non-planar surface. The spreader is made from flexible, resilient material, and has a tip and wings that emanate out from the hole in the top of the spreader.

U.S. patent Ser. No. 10/974,037; Colombo; Aldo The present invention regards an applicator device for the preparation and application of at least one medical substance, preferably a colored liquid, comprising: a hollow chamber having a hosting end and an opposite distal end in communication with means for contact with the patient; a cartridge slidingly inserted into said hollow chamber, containing at least one first medical substance, and having a first end external to the hollow chamber, and a second end completely inserted into the hollow chamber; a breaking means positioned at the distal end, capable of establishing a fluid communication between the internal of the cartridge and the means for contact with the patient; said second end being sealed by a filled double layer closure system containing at least one second substance, preferably colored, mixable and/or soluble with the first medical substance contained in the cartridge.

U.S. patent Ser. No. 10/478,601; Ueta, et al To provide a solution applicator with which irritation on an affected part of a patient may be reduced even when a solution is used. According to the present invention, an applicator comprises a solution container which comprises an opening, and a columnar brush member formed by bundling synthetic fibers in a columnar shape. The columnar brush member is disposed at the opening of the solution container, a tip portion of the columnar brush member at an outside of the solution container has a fan shape expanding in a perpendicular lateral direction against a pillar axial lengthwise direction, and a thickness of the fan-shaped tip portion of the columnar brush member decreases in a perpendicular lengthwise direction against the pillar axial lengthwise direction toward the tip portion of the columnar brush member. The solution applicator of the present invention has the fan-shaped tip portion so that irritation on an affected part may be decreased and a liquid tinea unguium medicine may be applied to the affected part.

Above patents provide details using screw type or rachet type mechanism to propel the topical product. Later patents use a premixes solution that was on hold and breaking the barrier allows the solution to flow to the sponge tip and it does not address the multiuse requirement and also these patents did not address consumer compliance of the greasiness stickiness, soiling to clothes and bed-clothing and enhancing the ready to use efficacy of topical dosage products.

SUMMARY

In some embodiments, the presently disclosed subject matter is directed to a topical product Hands free Applicator Drug delivery System (THADS™) for individual or for multimodal method of drug treatment, includes an airless metered pump product container or a suitable container with a modified nozzle to hold the applicator wand/tube that is intended for unit dose or multiple dose application, holds pharmaceutical product preferable topical product in "ready to act state" in which product outlet can connect and disconnect the one end (end #1) of wand of the applicator, the wand is straight or flexible/bendable, is 0.01 inch to 30 inch in length that directs drug product to another end (end #2) which is connected to a applicator sponge tip, the sponge tip can be connected or disconnected, the applicator sponge tip includes soft sponge which holds the drug product, the wand can be disconnected from end #1 after pumping the drug product, and drug is applied to the skin in the area of treatment, with little pressure or rubbing, the drug will be released from the sponge tip or being applied to the skin as "Hand free approach". When the soft sponge tip of the applicator end #2 can be disconnected and the wand tube can be inserted into the opening of an adhesive application pod (Appod™) which is adhered to the any part of the skin at the area of treatment, the drug product(s) can be pumped one dose or multiple doses required for one day or more can be pumped into the Appod™. The Appod™ system can spread and deliver the drug and biological molecules continuously for one application or drug intended for one day or more and make it more efficacious and consumer compliant topical drug treatment. THADS™ treatment can be used for human and animals. THADS™ system will be used on drugs to treat acute and chronic disorder for systemic and topical, drugs that are toxic, potent and require containment manufacturing that does require special handling instructions such drugs included are hormonal, cytotoxic, immunosuppressant, antibiotic, biological preparation, steroids, sensitizing drug substance, excipients, beta lactam antibiotics, drugs that goes through hepatic first pass metabolism and treatment situation in which can't be administered by mouth like nausea and vomiting.

In some embodiments, the topical products composition is in "Ready to Act State" a liquid, preferably, the drug is completely dissolved state and "ready to act form" and provide consistent effect as a solution or nanosized or micronized suspension, gel or an emulsion with a viscosity of 5000 cP or less more preferable viscosity below 3000 cP, drug releases above 15% in 15 minutes using a Franz diffusion cell using a 3.0 micron Nylon filter at 800 rpm stirring rate and a volumes of 10 ml dissolution medium (dissolution medium Water: Ethanol 70:30). The formulation does not freeze or change its mobility or rheological properties when it is stored at a refrigerated condition for 2 hours between 35° F. and 38° F. The refrigerated for 2 hours products show the load below 200 grams when tested using Brookfield Ametek CT3 Texture analyzer, using probe TA-11 at the following settings, Test Type: Compression, Test Target: Distance with Target value of 15 mm and target load of 10 grams with test speed of 1.0 mm/second.

In some embodiments, the pharmaceutical composition may also contain anti-itch to prevent the skin irritation. The solution also contains 5 to 90% water and a skin permeation enhancer. The topical product may be mixed with polymers to provide a sustainable action for longer period. This pharmaceutical composition can be applied using an applicator or an Adhesive bandage pod (Appod™) for skin, mucus, vagina, urethral and rectal applications.

In some embodiments, an adhesive bandage pod called as Application pod (Appod™), is similar to an adhesive bandage that will be applied or adhered into the area of treatment of the skin, when product composition solution added, the solution will spread and the Appod™ will hold the drug (solution, suspension, gel, lotion, emulsion, cream and ointment) in place for delivery of drug through the skin with adhesive covered in the bottom part of Appod™ that adheres to the skin. The drug can be pumped or added from a syringes or from a single unit dose or from a multi dose container, after removing the applicator tip sponge from the airless bottle applicator, the Appod™ will stick or adhere to the topical treatment area in the skin, like back, shoulder, knee, wrist etc., from which the drug will be held in the affected area for treatment for local and systemic action. Appod™ can be used to treat for 1 minute or an hour for 3 hours or of for one day or for multiple day treatment for months. This Appod™ can be a non-irritating and waterproof one.

In some embodiments, two or more topical products can be administered as multi-modal treatment without any drug-drug incompatibility at the same time to enhance the synergy in topical treatment as combination product using an Appod™. The active drug in the composition can be nano-sized, micro-sized, lipid encapsulated and dispersed evenly for topical application. The solution will penetrate passively after applying to the skin, it does not require rubbing on to the skin like an ointment or creams for drug penetration. Appod™ can have multiple compartments to administer more than one drug simultaneously in respective compartment for improved efficacy of the treatment. Two different drugs with different dose regimen can be administered in one Appod™ with multiple compartments for the drugs synergistic effect. The Appod™ can be sterile or non-sterile. Unit dose ready to act product can be added through a syringe or a unit dose container or other mechanism directly into Appod™.

In some embodiments, a multimodal method for the treatment of topical disease condition by not touching the drug product by hand and just pumping the drug solution to the Appod™ for systemic and local use for three time a day or once a day application, for 2-day application, for 3-day application, for 4-day application, for 5-day application, for 6-day application, for weekly application and up to one month application. Appod™ can have integrated solution reservoir that can deliver the drug passively or through a battery operated miniature pump that can delivery 1 microliter/min to 1000 microliter/min through a programable logic system for drug treatment for 1 hour or for 4 hours or for 8 hours or for 12 hours or for day or for 2 days, or for 3 days or for 4 days or for 5 days or for 6 days or for 7 days of for months. to treat various disease conditions using local action and for systemic action.

In some embodiments, a method for the treatment includes method of treatment for systemic disease condition with high drug concentration using Appod™ in one place or more than one place of the body like in both arms or both thighs or both arms and both thighs or a larger size. Appod™ can be adhered into stomach or back, thigh, arm areas for treatment of high dose drugs for systemic use that has issue in which the oral administration of the drug causes liver diseases or liver toxicity or goes through first pass metabolism or has severe adverse effects by administering the drug by oral, injection or nasal route of drug administration to treat chronic and acute disease conditions.

In some embodiments, the wand can be flexible and can bend to any direction or may not be flexible or may not bend, so that it is very convenient to apply the drug to skin or tissue in any part of the body. The wand can be connected into the product container as snap on or other suitable mechanism so that the end #1 can be closed with the product container and seamless transfer of the drug product to the end #2 of the wand or drug solution can be poured/pumped through a syringe or other means into a not connected or open end #1 of the wand to the product container, so that drug product can be poured or pumped on to the end #1, so that the product solution can travel to end #2 to the applicator. The wand can also have a flow control mechanism of the drug product after the end #1 of the wand, so that after pumping the wand can be disconnected and taken to the application area of the skin and the drug product flow control mechanism can be opened, so that drug can travel to end #2 for application. The wand end may have a sponge applicator or a leveling mechanism or an opening to take the drug product solution to the Appod™.

In some embodiments, the products texture testing show the load below 190 grams, preferably load below 80 grams when tested using Brookfield Ametek CT3 Texture analyzer, using probe TA-11 at the following settings, Test Type: Compression, Test Target: Distance with Target value of 15 mm and target load of 10 grams with test speed of 1.0 mm/second.

In some embodiments, the container of the dispensing pump spring tension testing shows the load above 1.0 kg and optimally above 5.0 kg when tested using Brookfield Ametek CT3 Texture analyzer, using probe TA-11 at the following settings, Test Type: Compression, Test Target: Distance with Target value of 10 mm and target load of 250 grams with test speed of 1.0 mm/second. This tension of the pump dispenser will prevent the back flow of the pumped solution from the applicator wand even in the upright position.

In some embodiments, the Appod™ can have more than one compartment to hold multiple drugs separately, or it can hold one compartment where multiple drugs can be added to it. The adhesive pod can have a chamber that can have uncontrolled delivery of the drug or also control drug delivery over 6 hours period or 12 Hours of period, or 24 hours or 72 Hours of controlled delivery for a week.

In some embodiments, the loaded drug will release 40 to 90% of drug in 5 minutes by testing dissolution using USP Apparatus 5 (paddle over disk method), the medium volume per vessel was 200 mL. The temperature should be maintained at 32±0.5° C. a distance of 25±2 mm between the paddle blade and the surface of the disk assembly. The rotation speed was set at 50 rpm.

In some embodiments, the method of treatment using THADS™. for multimodal topical drug delivery system, that has penetration enhancers along with skin anti-irritants are added to one compartment of the Appod™ and the drugs like small molecules, peptides and biological drugs intended for the treatment will be held in another compartment of the Appod™. The penetration enhances will be pumped continuously on to the treatment are for fixed number of hours follows by pumping the desired dose of the drug like small molecules, peptides and Biologicals from another compartment pod, this method enhances the drug penetration, this method can be used as a standalone dosage form or multimodal drugs treatment as a kit to treat various skin disease conditions requires multiple drug combinations for treatment of Atopic dermatitis, Shingles, Psoriasis, eczema, nausea vomiting, cancer central nervous system treatment, pain disorder, Gastrointestinal disorder, acute disease conditions, etc. where all the drug are administered using THADS™ make more effective, high patient compliance using with or without Appod™. The drug combination can be all drug in one formulation or two drug in one formulation or three drug in one formulation or individual drug can be administered using Appo™d.

In some embodiments, the ready to act drug solution that added into the Appod™ may contain anti-itching drug like antihistamine or steroids, antimicrobial drug along with the drug product intended for treatment to prevent the itching or irritation or infection that can cause by Appod™, the PVA ring or non-woven or woven fabric in the Appod™ can be coated with anti-itching and antimicrobial drugs to prevent skin itch and infection that comes from immediate contact of the Appod™ to the skin.

In some embodiments, the Appod™ of the rate controlling layer is made up of a non-woven fabric or woven fabric that may be coated with Diphenhydramine HCl or Hydrocortisone to prevent irritation with 0.1 g/cms$^2$ to 3.0 g/cms$^2$ that will control the flow or retain the ready to act solution intended for local action or systemic action and also may have a pod or a liquid or suspension holding pod or bag that will hold 0.1 ml to 50 ml and deliver the 0.25 to 25 ml/day intended for local and systemic administration. The Appod™ may have a skin barrier seal ring that will contain the drug product solution of the liquid, or suspension, emulsion, ointment cream within the ring, the ring may be soft, flexible and have adhesive to it, the outer layer of the skin may have an absorbent to any residual solution or drug product seeping or leaking out of the ring, the Appod™ will have a bag or pod that will contain the drug product in liquid or semi-liquid state that will control the delivery into the Appod™ to deliver the drug for treatment for 0.1 hours to 3 months, this bag can be connected with a micro-motor to pump a predetermined amount of solution from the bag or pod to the treatment area, the motor that is connected to a smart watch or a device that can control the flow rate of the drug product. The inside of the ring may have a non-woven fabric or may not have then non-woven fabric. The ring may be coated with antibacterial, antiviral, or anti itching and anti-irritating drug.

In some embodiments, the Appod™ is used for immediate release application like one time a day, 3 times a day and for extended-release application for 2 day, 3, days, 4, days, 5 days, 6 days, 7 days, weeks, or months. The Appod™ uses a silicone or suitable medical grade polymer open dome with duckbill valve or silicone or suitable medical grade polymer closed dome with duckbill valve and a micro porous opening or a micro hole at the bottom to drip the drug solution as a capillary movement to the treatment are of the skin surface or a silicone or a suitable medical grade reservoir bag connected to a micro or nano peristaltic pump or Piezo electric liquid pump or micro pump to pump the required quantity of solution to the treatment area of the skin. The bottom layer of the Appod™ has nonirritating adhesive layer, the adhesive layer is applied on to the non-woven or woven fabric, the non-woven or the woven fabric is coated with drug that prevents irritation to the skin. The Appod™ includes the Ethylene vinyl acetate (EVA) foam ring or other suitable polymer ring that is non absorbent but retains the drug solution within the ring and exposes the skin directly for the topical drug, the ring can hold 0.1 mL to 10 mL of that can used the apply drugs, the EVA ring may be covered with non-woven or woven fabric. The top layer of the Appod™ includes breathable or non-breathable fabric.

In some embodiments, the Appod™ or an applicator pod this is a wearable, adheres to the skin to which drug product that is liquid and semi liquid in nature can be filled and refilled for topical treatment and it spread itself with in the Appod™ for the area of treatment.

In some embodiments, the Appod™ will enable to wear cloths without interfering the drug delivered into the skin, The Appod™ will reduce the odor of the drug. The drug product will not mixed with the adhesive of the Appod™, the drug will remain free (not bonded with adhesive or embedded in matrix) and ready to act condition in the pod to provide better efficacy and better consistency Appod™ intended to treat topical drug administration minimized, prevents or does not cause irritant contact dermatitis (ICD) and blisters during topical treatment and some instance Hydrocortisone solution or other steroid solution or Antiallergenic solution can be added into the Appod™ along with drug intended for treatment to eliminate skin irritation and blisters.

In some embodiments, Appod™ has a polymer dome preferably silicone dome that has an opening to inlet for the topical drug products and to allow air and make the skin breath. The dome has a Duckbill vale to prevent the back flow of the topical drug products. In some embodiments, topical product like solution or suspension or emulsion that contains one or more pain-relieving drugs like diclofenac sodium, Ibuprofen, acetaminophen, Menthol, Camphor, Methyl salicylate, Naproxen, benzocaine, lidocaine, tetracaine, propofol, meloxicam, piroxicam, gabapentin, pregabalin, corticosteroids like dexamethasone, hydrocortisone, clobetasol, cortisone and natural and synthetic pain-relieving drugs and Inorganic salts like Magnesium sulphate, sodium chloride, potassium chloride, potassium nitrate, strontium chloride, strontium nitrate, zinc chloride along with 5 to 95% water to treat, pian, surgery pain, muscle cramps and recovery after workout.

In some embodiments, Appod™ can be prefilled with the drug product, by removing the release liner, will initiate the drug release from the Appod™ to the skin for the intended treatment of the skin.

In some embodiments, Appod™ has a direct visualization area, which allows to inspect the spreading of added topical solution and treatment progress in cases like wounds or swelling, itching, bruising, skin etc.

BRIEF DESCRIPTION OF THE FIGURES

FIG. 4a is an illustration of a bent wand 5 with sponge tip.

FIG. 4b is an illustration of a straight wand 5 with sponge tip.

FIG. 5 is a texture analyzer graph of two different bottles that shows the load on the airless bottle spring to prevent the back flow of the solution.

DETAILED DESCRIPTION

Figure 1A:
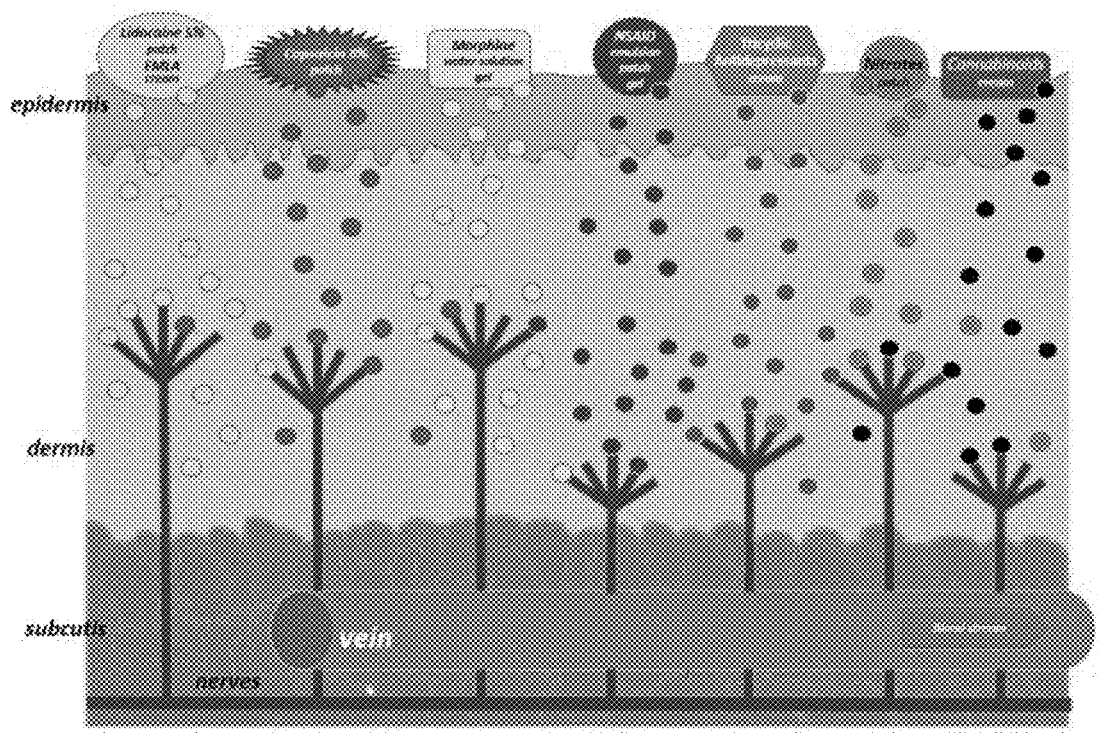
FIG. 1a is an illustration of the topical products, i.e., transdermal patches intended for systemic circulation application.

The presently disclosed subject matter is introduced with sufficient details to provide an understanding of one or more particular embodiments of broader inventive subject matters. The descriptions expound upon and exemplify features of those embodiments without limiting the inventive subject matters to the explicitly described embodiments and features. Considerations in view of these descriptions will likely give rise to additional and similar embodiments and features without departing from the scope of the presently disclosed subject matter.

Unless defined otherwise, all technical and scientific terms used herein have the same meaning as commonly understood to one of ordinary skill in the art to which the presently disclosed subject matter pertains. Although any methods, devices, and materials similar or equivalent to those described herein can be used in the practice or testing of the presently disclosed subject matter, representative methods, devices, and materials are now described.

Following long-standing patent law convention, the terms "a", "an", and "the" refer to "one or more" when used in the subject specification, including the claims. Thus, for example, reference to "a device" can include a plurality of such devices, and so forth. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise indicated, all numbers expressing quantities of components, conditions, and so forth used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, and/or percentage can encompass variations of, in some embodiments +/−20%, in some embodiments +/−10%, in some embodiments +/−5%, in some embodiments +/−1%, in some embodiments +/−0.5%, and in some embodiments +/−0.1%, from the specified amount, as such variations are appropriate in the disclosed packages and methods.

As used herein, the term "and/or" includes any and all combinations of one or more of the associated listed items.

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

Technical Problem: There are three primary issues with topical dosage forms 1) Efficacy and 2) Patient compliance and 3) Clinical needs.

Efficacy: No fast acting Topical creams & Ointments.

Pharmaceutical dosage from in oral dosage forms there are immediate release and orally disintegrating product. However, topical products do not have an immediate release product for a rapid onset. This is primarily the topical product ointments and creams that are made with active drugs along with excipients that that have a thick consistency to hold the drug for a longer time when applied on to the skin. Also, the excipients intend to melt at body temperature when applied into a thin layer on to the skin. When the ingredients are exposed to cold conditions like in Minnesota, New York, and other Northern states that experience cold weather conditions, the excipients may become hard in the cold conditions and may have inconsistent release of drug and it may prolong the onset effect.

Transdermal Patches: The drug is stored in the Transdermal drug delivery system (TDDS) either in a reservoir or impregnated into the fabric or to the adhesive of the patch.

Pharmacokinetics of topical products (ointment and creams): The drug absorbed into the skin follows a three-step process from ointment creams and TDDS. Step #1: Drug concentration gradient is developed with in the formulation and the drug starts to move down the gradient. The ointment or cream of topical product needs to absorb water from the skin and dissolve the drug in the formulation and form a concentration gradient within the formulation. Step #2: A second drug reservoir is established in the stratum corneum. As the drug moves further into the skin, Step #3: The drug is absorbed into the local capillary vasculature and is then transported into the systemic circulation.

As a result of this absorption process, there is a delay between Topical drug products/TDDS application and the development of a desired minimum effective concentration (MEC). This delay varies between drugs. There is an initial period in which drug concentrations are hardly measurable. The time to reach steady-state plasma concentrations vary considerably and may be achieved completely only after two to three patch applications (1).

The disadvantage of the topical drug delivery is on the lack of rapid onset of action as the drug takes some time to get released from its vehicle and then to penetrate (absorb) through the skin and there are variations between individuals in the rate at which drugs are absorbed via the skin due to factors such as thickness of the stratum corneum, skin hydration, underlying skin diseases or injuries, ethnic differences, and body temperature.

Patient Compliance: Patients feel uncomfortable on application of topical medications, as it is often considered and reported by the patients as being more difficult than simply taking a pill (2, 3, 4). Patient, treatment, and disease factors have been appointed to justify poor adherence. Regarding treatment, poor acceptability of the topical vehicles properties as very greasy, desiccating, or sticky vehicles and the smell of the preparation and staining of clothes, time required for its application have been reported by patients with chronic skin disorders as barriers to optimal treatment adherence. Staining or messing of clothes is often associated with the use of ointments, creams, pastes, and gels. Also, the topical route is that it has no dosing accuracy, and it is difficult to formulate with different drugs and ingredients.

In the study on chronic skin diseases, stickiness (44%), and attachment to clothes (34%) and bed-clothing (27%) were reported to be the reasons of poor adherence, furthermore, being busy (25%). These results suggest that the reason for poor adherence to use topical ointment is complex. (6).

Clinical needs: Multimodal therapy approaches that combine interventions aimed at different aspects of disease are emerging as potential—and perhaps essential—ways to enhance clinical outcomes for patients and this multimodal therapy approach in topical drugs is impossible except few combinations therapy in which two drugs are combined in one ointment or cream as a standalone topical product. If multiple drugs need to be applied for treatment at the same time, it is impossible to apply two or more products at the same time one up on another in the form of ointment or a cream but can be applied in different area of the skin. It is impossible to provide multimodal drug therapy for effective treatment in topical dosage forms.

Disease conditions: Shingles is a viral infection that causes a painful, burning rash that may appear as a stripe on the trunk of the body. There is oral treatment available, but due to constant pain and burning sensation, THADS™ technology will be helpful to keep the pain killer medication along with Antiviral and blister healing drug at all the time in contact with the rash associated with the Shingles to minimize the pain and expedite the healing process.

Multimodal drug administration: Romita Paolo Et al. (7). indicated in their study, that all the transdermal patches cause skin irritation and Allergic contact dermatitis, with THADS™ technology, Chlorpheniramine solution and Hydrocortisone 1% can be used along with the drug intended for treatment will eliminate the skin irritation and allergic contact dermatitis associated with topical delivery of drugs using transdermal patches.

With multimodal drug approach many acute disease conditions like pain, cancer and diabetes can be treated. Using THADS™ Appod™, more than one drug or combination of two or three or more drugs can be administered at the same time, THADS™ system allows multiple drugs to be held in the treatment area for its absorption at the same time and helps the multimodal drug treatment of acute disease conditions.

Liver Toxicity from oral drugs. Topical delivery of large molecules like proteins and peptides of biotechnology products: most of the peptides and proteins of biotechnology products are delivered through subcutaneously or other parental route, due to high molecular weight of the compounds. THADS™ has the provision to deliver constantly the skin permeation agent along with proteins and peptides to deliver it through the skin. High drug content in Transdermal patches: FDA approved transdermal patches had very high drug content than it is really required, as shown below:

EMSAM transdermal systems are available in three strengths that deliver approximately 6 mg, 9 mg, or 12 mg of selegiline over 24 hours. Each corresponding system has an active surface area of 20 cm$^2$, 30 cm$^2$, or 40 cm$^2$ containing 20, 30, or 40 mg of selegiline.

Lidoderm adhesive patch contains 700 mg of lidocaine, per 10 cm×14 cm, but only 3% is bioavailable, i.e., only 21 mg of drug enter into to blood stream. Apply the prescribed number of patches (maximum of 3), only once for up to 12 hours within a 24 hour period.

Excelon 5 cm$^2$ patch contains 9 mg rivastigmine base, with in vivo release rate of 4.6 mg/24 hours. Each 10 cm$^2$ patch contains 18 mg rivastigmine base, with in vivo release rate of 9.5 mg/24 hours Oxytrol 39 cm$^2$ patch contains 36 mg of oxybutynin for nominal delivery of 3.9 mg oxybutynin per day when dosed in a twice weekly regimen.

Salonpas Pain relieving Lidocaine patch of 10 cm×14 cm contains 560 mg of Lidoaine, Aspercreme patch 10×14 cms contain 246 mg of lidocaine, Icyhot patch of 10 cm×14 cm contains 240 mg of lidocaine and 60 mg of menthol. also, per package inserts a 100 mcg/h fentanyl TDDS containing 10 mg of fentanyl while a 0.3 mg/day clonidine TDDS has 7.5 mg of clonidine.

The marketed transdermal patches comprising the drug candidates mixed with adhesive, the drug has low diffusivity through the adhesive, so the drug content of the transdermal patches is very high than the quantity of drug is bioavailable.

The risk of toxicity and adverse outcomes are further increased if the TDDS is tampered with or used improperly. Solution to Problems:

The present invention has been made in view of the problems associated with the topical products/TDDS for human and animal products of ointment, creams, sprays, emulsion, suspension etc., an object of the present invention is to provide a rapid onset of action and patient compliance of hands free application using Topical product Hand free Applicator Drug delivery System (THADS™) and a multi-modal method for treating using the THADS™.

The present inventors have conducted relevant study to achieve the above object. As a result, the inventors have found the following Topical product Hand free Applicator Drug delivery System (THADS™). Specifically, Topical product Hand free Applicator Drug delivery System (THADS™) System comprise a) A metered dose container that is airless container that can deliver a measured amount of drug at any (360° C.) angles of the container and formulation that is made as "ready to act "state which the drug is present in highly dissolved state less viscous compared to ointment and contains polypropylene that prevents freezing from cold conditions, alcohol for rapid drying after application and dimethyl sulfoxide to solubilize the hydrophilic and hydrophobic drug components and enhance skin penetration, b) A wand is a flexible and has two ends. end #1 can be attached and detached to the airless bottle and end #2 can be attached and detached to the sponge tip applicator. after connecting the wand end #1 to the airless container, drug is pumped from airless container, after pumping the drug the wand will be disconnected at end #1 and applied into the skin through the smooth sponge tip "without using the hand", the solution is non-greasy and spreads easily, and it will dry rapidly. c) Appod™, an adhesive bandage pod that can be applied to a part of the skin that needs to be treated for local and systemic application, the Appod™ will have an opening through which the end #2 of the wand will be inserted and the ready to act drug product solution will be pumped in for the necessary dose i.e. either one dose or multiple dose of the drug, from there the Appod™ will hold the drug very close in contact with the skin and for longer time and deliver the drug continuously in predetermined manner to the skin, The Appod™ act as reservoir that can deliver multiple drug continuously for treatment and the Appod™ will cover the drug product, cloths will not be soiled and will provide very efficacious treatment and high patient compliance for topical treatment.

Appod™ has adhesive on the border of the outer polymeric film, most of the on inner non-woven fabric or pad does not contain adhesive, the adhesive does not interfere the drug release through the skin, so the drug content requirement by using Appod™ will be low compared to the marketed transdermal patches.

Advantageous Effects of Invention: The present invention makes it possible to provide a THADS™ a multimodal method for delivering the drug product topically with enhanced ready to act drug form for immediate action, with exact dose needed producing the same efficacy each and every time and also with the use of Appod™, which will cover the drug product from the cloths, unpleasant odor from drug, poor cosmetic properties, messy, sticky, or greasy vehicles and also enhance the consumer compliance from once-a-day dose administration.

Topical products are classified, and its description given in Table 1 below:

TABLE 1

Classification of topial formulation
Classification of topical formulations

| | |
|---|---|
| Solution | Water or alcoholic lotion containing a dissolved powder. It is used as tincture or wash and it will run through the skin if applied. |
| Lotion | Usually considered thicker than a solution and more likely to contain oil as well as water or alcohol. A shake lotion separates into parts with time so needs to be shaken into suspension before use. It can be applied on to the skin by taking in hand and applying it, it will stick on to the hand and cloths |
| Cream | Thicker than a lotion, maintaining its shape, for example, a 50/50 emulsion of oil and water. Requires preservative to extend shelf life. Often moisturizing. It can be applied on to the skin by taking in hand and applying it, it will stick on to the hand and cloths |

TABLE 1-continued

Classification of topial formulation
Classification of topical formulations

| | |
|---|---|
| Ointment | Semi-solid, water-free or nearly water-free (80% oil). Greasy, sticky, emollient, protective, occlusive. No need for preservative, so contact allergy is rare. May include a hydrocarbon (paraffin), wool fat, beeswax, macrogols, emulsifying wax, cetrimide or vegetable oil (olive oil, arachis oil, coconut oil). It can be applied on to the skin by taking in hand and applying it, it will stick on to the hand and cloths |
| Gel | Aqueous or alcoholic monophasic semisolid emulsion, often based on cellulose and liquefies upon contact with skin. Often includes preservatives and fragrances. It can be applied on to the skin by taking in hand and applying it, it will stick on to the hand and cloths |
| Paste | A concentrated suspension of oil, water and powder. It can be applied on to the skin by taking in hand and applying it, it will stick on to the hand and cloths |
| Aerosol foam or spray | A solution with pressurized propellant. Hands will be used to rub the spray; it will stick on to the hand and cloths. |
| Powder | Solid, for example, talc (a mineral) or corn starch (vegetable). It can be applied on to the skin by taking in hand and applying it, it will stick on to the hand and cloths |
| Solid | Antiperspirant or sunscreen stick. May melt on reaching body temperature (eg, a suppository). it can stick to the cloths |
| Transdermal Patch | Drug delivery system allows precise dosing includes an adhesive. The drug is embedded as matrix with polymer Example Fentanyl Patch and Buprenorphine patch |

Figure 1B:
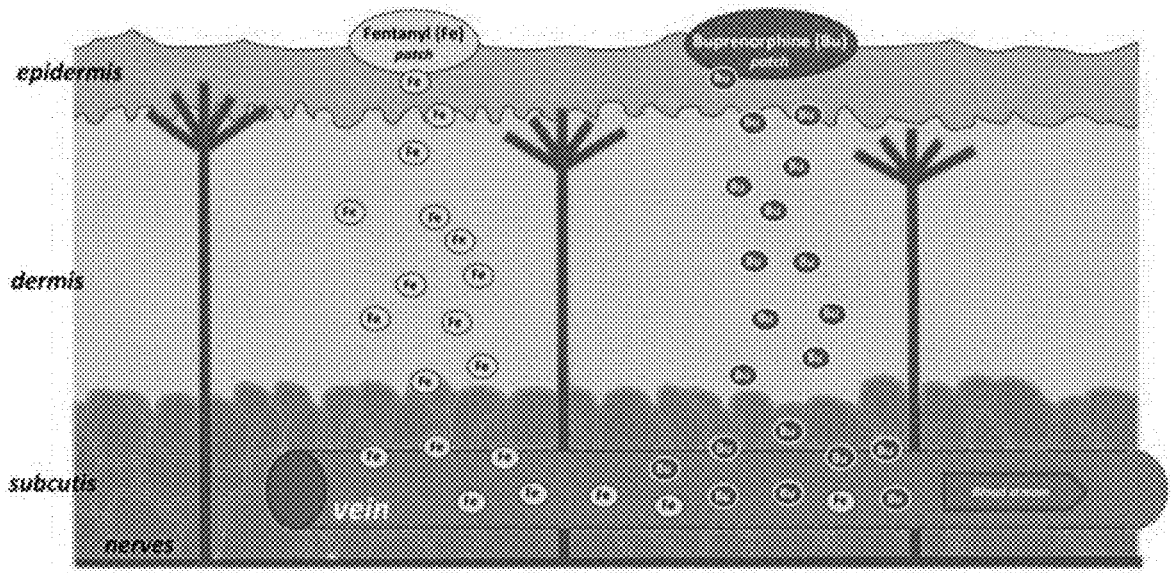
FIG. 1b is an illustration of efficacy of topical products using THADS™.

Illustration of the topical product (i.e. Ointment, gel, creams and some patch) intended to be treatment for local action for the skin is shown in FIG. 1a. Illustration of the topical products (8) i.e., transdermal patches intended for systemic circulation application are illustrated in FIG. 1b.

Efficacy of topical products using THADS™: Pharmacokinetics of currently marketed topical products (ointment, creams, and transdermal patches): The drug absorbed into the skin follows a three-step process from ointment creams and TDDS. Step #1: Drug concentration gradient is developed with in the formulation and the drug starts to move down the gradient. The ointment or cream of topical product needs to absorb water from the skin and dissolve the drug in the formulation and form a concentration gradient within the formulation. Step #2: A second drug reservoir is established in the stratum corneum. As the drug moves further into the skin, Step #3: The drug is absorbed into the local capillary vasculature and is then transported into the systemic circulation.

Pharmacokinetics of topical products using THADS™: The drug absorbed into the skin follows a two-step process. Step #1 A reservoir is established at the stratum corneum directly, as the ready to act drug is held closer to the skin by Appod™. As the drug moves further into the skin. Step #2 The drug is absorbed into the local capillary vasculature and is then transported into the systemic circulation.

THADS™ eliminates the one-time consuming step (step #1) of the pharmacokinetics of the topical products like ointment, creams and transdermal patches and put the step #2 directly and enhance the efficacy of the drug with the hands-free application, fast acting and with Appod™ it enhances the patient compliance.

Efficacy of the Topical Products

List of currently marketed topical products and how the product is applied on the skin Here are the FDA approved products and its way of application into the skin source (9):

TABLE 2

List of FDA approved topical products and its dose administration

| Drug Product | How is applied on the skin |
|---|---|
| Tacrolimus Ointment | Apply a thin layer of PROTOPIC (tacrolimus) Ointment to the affected skin twice daily. The minimum amount should be rubbed in gently and completely |
| Enstilar ™ (calcipotriene and betamethasone dipropionate) Foam is indicated for the topical treatment of plaque psoriasis | Gently rub in Enstilar Foam to your affected areas. |
| EXTINA (ketoconazole) Foam, 2% is indicated for the topical treatment of seborrheic dermatitis | Pick up small amounts of EXTINA Foam with the fingertips, and gently massage into the affected area(s) until the foam disappears. |
| DIFFERIN ™ Cream | A thin film of the cream should be applied to the skin areas where acne lesions appear, using enough to cover the entire affected areas lightly |
| EPIDUO FORTE gel is indicated for the topical treatment of acne vulgaris | Apply a thin layer of EPIDUO FORTE gel to affected areas of the face and/or trunk once daily after washing. |

TABLE 2-continued

List of FDA approved topical products and its dose administration

| Drug Product | How is applied on the skin |
| --- | --- |
| Panretin ™ gel 0.1% contains alitretinoin and is intended for topical application only. | Sufficient gel should be applied to cover the lesion with a generous coating. |
| Finacea(azelaic acid) Foam, 15% is indicated for topical treatment of the inflammatory papules | Apply Finacea Foam twice daily (morning and evening) to the entire facial area (cheeks, chin, forehead, and nose). Wash hands immediately following application of Finacea Foam. |
| FINACEA ™ (azelaic acid) Gel, 15% is indicated for topical treatment of the inflammatory papules | Apply and gently massage a thin layer of FINACEA Gel into the affected areas on the face twice daily (morning and evening). Wash hands immediately following application |
| DIPROLENE ™ Ointment is a corticosteroid indicated for the relief of the inflammatory and pruritic manifestations | Apply a thin film of DIPROLENE Ointment to the affected skin areas once or twice daily. |
| DIPROLENE ™ AF Cream is a corticosteroid indicated for the relief of the inflammatory and pruritic manifestations | Apply a thin film of DIPROLENE cream to the affected skin areas once or twice daily. |
| SERNIVO Spray is indicated for the treatment of mild to moderate plaque psoriasis | Apply SERNIVO Spray to the affected skin areas twice daily and rub in gently. |
| Enstilar ™ (calcipotriene and betamethasone dipropionate) Foam is indicated for the topical treatment of plaque psoriasis | Apply Enstilar Foam to affected areas once daily for up to 4 weeks. Rub in Enstilar Foam gently. Wash hands after applying the product. |
| WYNZORA Cream is indicated for the topical treatment of plaque psoriasis | Apply WYNZORA Cream to affected areas once daily for up to 8 weeks. Rub in gently to ensure that the plaques are saturated with the cream |
| Taclonex ™ Ointment is indicated for the topical treatment of plaque psoriasis | Apply an adequate layer of Taclonex ™ Ointment to the affected area(s) once daily for up to 4 weeks. Taclonex ™ Ointment should be rubbed in gently and completely. Patients should wash their hands after applying Taclonex ™ Ointment. |
| Taclonex ™ Topical Suspension is indicated for the topical treatment of plaque psoriasis | Apply Taclonex Topical Suspension to affected areas on the scalp and body once daily for up to 8 weeks. Instruct patients to wash their hands after applying the product |
| LOTRISONE (clotrimazole and betamethasone dipropionate) cream, 1%/0.05%, | Apply a thin film of LOTRISONE cream into the affected skin areas twice a day for one week. Gently massage a sufficient amount of LOTRISONE cream into the affected skin areas twice a day for two weeks. |
| Targretin ™ (bexarotene) gel 1% contains bexarotene and is intended for topical application | Apply Targretin gel to your CTCL lesions using a clean washed finger. |
| SORILUX Foam is indicated for the topical treatment of plaque psoriasis | Apply a thin layer of SORILUX Foam twice daily to the affected areas and rub in gently and completely. |
| LOPROX ™ Cream (ciclopirox) 0.77% is for topical use. | Gently massage LOPROX ™ Cream into the affected and surrounding skin areas twice daily, in the morning and evening. |
| LOPROX ™ (ciclopirox) Topical Suspension, 0.77% is for topical use. | Gently massage LOPROX ™ Topical Suspension into the affected and surrounding skin areas twice daily, in the morning and evening |
| VELTIN ™ (clindamycin phosphate and tretinoin) Gel, 1.2%/0.025% is indicated for the topical treatment of acne vulgaris | VELTIN Gel should be applied once daily in the evening, gently rubbing the medication to lightly cover the entire affected area. |
| OLUX Foam is a corticosteroid indicated for treatment of moderate to severe plaque psoriasis | Apply a thin layer of OLUX Foam to the affected skin areas 2 times each day. Wash your hands after using OLUX foam |
| CLOBEX ™ (clobetasol propionate) Spray, 0.05% contains clobetasol propionate, a synthetic fluorinated corticosteroid, for topical use | CLOBEX ™ (clobetasol propionate) Spray, 0.05% should be sprayed directly onto the affected skin areas twice daily and rubbed in gently and completely. |
| CLOBEX ™ Lotion, 0.05% is a super-high potent topical corticosteroid formulation indicated for the relief of the inflammatory and pruritic manifestations | CLOBEX Lotion, 0.05% should be applied to the affected skin areas twice daily and rubbed in gently and completely. Patients should wash their hands after applying the medication. |

TABLE 2-continued

List of FDA approved topical products and its dose administration

| Drug Product | How is applied on the skin |
|---|---|
| EUCRISA is indicated for topical treatment of mild to moderate atopic dermatitis | Apply a thin layer of EUCRISA twice daily to affected areas. |
| ACZONE™ Gel, 5%, is indicated for the topical treatment of acne vulgaris. | apply approximately a pea-sized amount of ACZONE Gel, 5%, in a thin layer to the acne affected areas twice daily. Rub in ACZONE Gel, 5%, gently and completely. |
| VERDESO ™ (desonide) Foam, 0.05% is indicated for the treatment of mild to moderate atopic dermatitis | A thin layer of VERDESO Foam should be applied to the affected area(s) twice daily. Dispense in hands and gently massage into affected areas of the face until the medication disappears |
| Topicort ™ (desoximetasone ointment USP) 0.25% is indicated for the relief of the inflammatory and pruritic manifestations | Apply a thin film of Topicort ™ (desoximetasone ointment USP) 0.25% to the affected skin areas twice daily. Rub in gently. |
| PENNSAID is indicated for the treatment of the pain of osteoarthritis of the knee | dispense PENNSAID into the palm of your hand and apply on to the knees |
| Ecoza (econazole nitrate) topical foam, 1%, is indicated for the treatment of interdigital tinea pedis caused by Trichophyton rubrum | Small amount of foam about the size of a goal ball in the palm of your hand. Use your finger tips to scoop up small amount of Ecoza topical foam and apply the affected skin areas on your feet. Gently rub the foam into the skin. |
| TRI-LUMA Cream is a combination of fluocinolone acetonide (a corticosteroid), hydroquinone (a melanin synthesis inhibitor), and tretinoin (a retinoid) that is indicated for the short-term treatment of moderate to severe melasma of the face, | Apply a thin film of TRI-LUMA Cream to the affected area once daily, |
| Tolak (fluorouracil) Cream is indicated for the topical treatment of actinic keratosis lesions of the face, | Apply Tolak Cream once daily in an amount sufficient to cover the lesions of the face, ears, and/or scalp with a thin film, using the fingertips to gently massage the medication uniformly into the skin. |
| Cordran Lotion is indicated for the relief of the inflammatory and pruritic manifestations of cortico-steroid-responsive dermatoses. | A small quantity of Cordran Lotion should be rubbed gently into the affected area 2 or 3 times daily. |
| CUTIVATE ™ Lotion is a corticosteroid indicated for the relief of the inflammatory and pruritic manifestations of atopic dermatitis | Apply a thin film of CUTIVATE ™ Lotion to the affected area 1 time each day. Gently rub into your skin |
| HALOG OINTMENT (Halcinonide Ointment, USP) 0.1% is indicated for the relief of the inflammatory and pruritic manifestations | Apply a thin film of 0.1% HALOG OINTMENT (Halcinonide Ointment, USP) to the affected area two to three times daily. |
| BRYHALI ™ (Halobetasol propionate) lotion, 0.01% is indicated for the topical treatment of plaque psoriasis in adults | Apply a thin layer of BRYHALI Lotion to affected areas once daily. Rub in gently. Wash hands after each application |
| Texacort Topical Solution 2.5% is indicated for the relief of the inflammatory and pruritic manifestations | generally applied to the affected area as a thin film for three or four times daily depending on the severity of the condition |
| ZYCLARA Cream, 2.5% and 3.75% are indicated for the topical treatment of clinically typical visible or palpable, actinic keratoses | ZYCLARA Cream should be applied as a thin film to the entire treatment area and rubbed in until the cream is no longer visible. |
| SOOLANTRA cream is indicated for the treatment of inflammatory lesions of rosacea | squeeze a pea-sized amount of SOOLANTRA cream from the tube onto your fingertip., Spread the cream smoothly and evenly in a thin layer |
| EXTINA (ketoconazole) Foam, 2% is indicated for the topical treatment of seborrheic dermatitis in immunocompetent | Pick up small amounts of EXTINA Foam with the fingertips, and gently massage into the affected area(s) until the foam disappears. |

TABLE 2-continued

List of FDA approved topical products and its dose administration

| Drug Product | How is applied on the skin |
| --- | --- |
| Noritate ™ (metronidazole cream) Cream, 1%, is indicated for the topical treatment of inflammatory lesions and erythema of rosacea | Apply and rub in a thin film of Noritate once daily to entire affected area |
| ZILXI is indicated for the treatment of inflammatory lesions of rosacea in adults | small amount of topical foam (e.g. a cherry-sized amount) should be expressed from the can onto the fingertips of the hand and then applied as a thin layer over all areas of the face |
| ELOCON ™ Cream is a corticosteroid indicated for the relief of the inflammatory and pruritic manifestations | apply a thin film of ELOCON Cream to the affected skin areas once daily. |
| ELOCON ™ Lotion is a corticosteroid indicated for the relief of the inflammatory and pruritic manifestations | Apply a few drops of ELOCON Lotion to the affected skin areas once daily and massage lightly until it disappears. |
| ELOCON ™ Ointment is a corticosteroid indicated for the relief of the inflammatory and pruritic manifestations | Apply a thin film of ELOCON Ointment to the affected skin areas once daily. |
| Naftin ™ Cream, 1% and Naftin ™ Gel, 1% contain the synthetic, broad-spectrum, antifungal agent naftifine hydrochloride | A sufficient quantity of NaftinTM Cream, 1% should be gently massaged into the affected and surrounding skin areas once a day |
| Naftin - ™ Gel, 1% contains the synthetic, broad-spectrum, antifungal agent naftifine hydrochloride. | A sufficient quantity of Naftin ™ Gel, 1% should be gently massaged into the affected and surrounding skin areas twice a day, |
| ELIDEL ™ (pimecrolimus) Cream, 1% is indicated as second-line therapy for the short-term and non-continuous chronic treatment of mild to moderate atopic dermatitis | Apply a thin layer of ELIDEL Cream, 1% only to the affected skin areas, twice a day, Wash hands before using ELIDEL Cream |
| Protopic ™ Ointment, both 0.03% and 0.1% for adults, and only 0.03% for children aged 2 to 15 years, is indicated as second-line therapy for the short-term and non-continuous chronic treatment of moderate to severe atopic dermatitis | Apply a thin layer of Protopic ™ Ointment, 0.03% to the affected skin twice daily. The minimum amount should be rubbed in gently and completely |
| FABIOR ™ (tazarotene) Foam, 0.1% is indicated for the topical treatment of acne vulgaris | Dispense a small amount of foam into the palm of the hand. Using fingertips, apply only enough foam to lightly cover the entire affected areas of the face and/or upper trunk with a thin layer; gently massage the foam into the skin until the foam disappears |
| TAZORAC ™ (tazarotene) Cream, 0.05% and 0.1% are indicated for the topical treatment of patients with plaque psoriasis. | Apply TAZORAC Cream only to psoriasis skin lesions, avoiding uninvolved skin. Wash hands thoroughly after applying TAZORAC Cream |

Figure 2A:
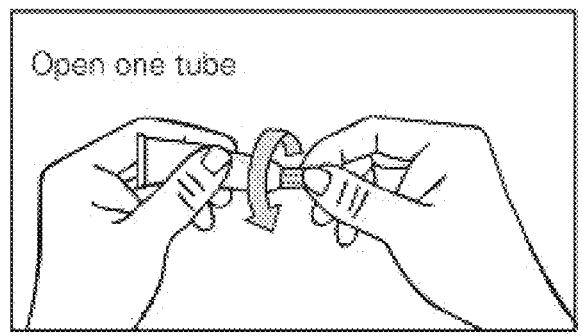
FIGS. 2a-2d are illustrations of application of prior art current topical products applied to the skin.
Figure 2B:
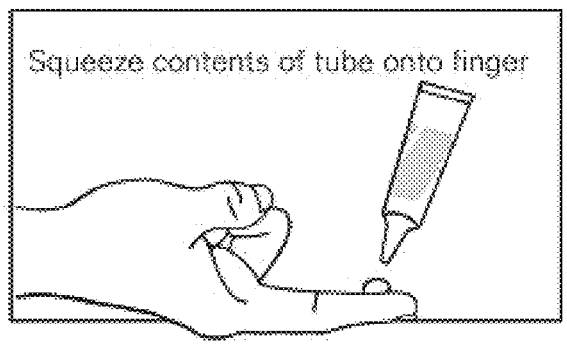
Figure 2C:
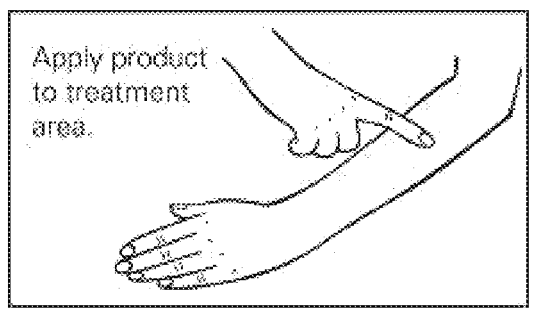
Figure 2D:
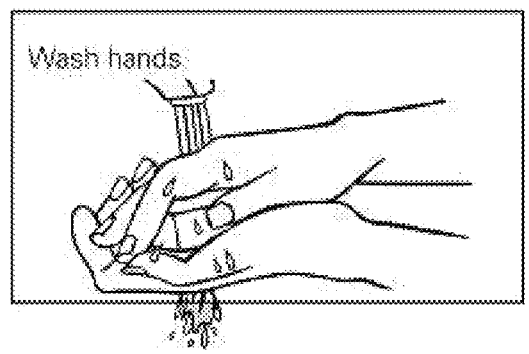

Most of the FDA approved topical products are packed in a tube, and it is impossible to take the exact dose each time for use and here is the instruction provided for the application of topical drug from its tube. FIGS. 2a-2d illustrate the method by which current topical products are applied on to the skin. In FIG. 2a, the tube in opened. In FIG. 2b, squeeze the gel or an ointment or a cream from the tube onto a fingertip. In FIG. 2c, Spread the gel or an ointment or a cream evenly over only the skin area to be treated. In FIG. 2d, wash your hands right away after applying.

With all the above FDA approved topical products except transdermal patches, (1) there is no possible way to take the exact dose needed for the topical treatment from the product container; (2) There is no possible way to transfer or apply all the topical product from your hand to skin, there is always inconsistent amount of drug will be sticking to you hand and it will be washed away; (3) When you put on clothes, it gets solid and it takes away part of the topical product. All the above factors create the underdose or overdose with current marketed topical products.

The topical solutions, which has the drug in dissolved state can act rapidly and can penetrate the skin faster, but it can't be hold on to the skin to the treatment, so most of the currently existing topical formulations in the market (ointment, cream, gel, etc. are made up by adding ingredients to make it viscous and thick in consistency and ability to stick to the skin surface, so that the products need to be rubbed on to the skin, whereby the ingredients will melt and by its viscous nature it will hold the drug on to the skin till it penetrates the skin for treatment. Hence longer onset for its activity.

The current topical products when applied to the skin and there is no mechanism to hold on the skin for longer period, so it is applied 3 to 4 times a day for local treatment, hence there are not many topical products (ointments, creams and gels) that can be applied on the skin to treat the drug for systemic circulation for which the drug will release into the Epidermis and needs to go to the blood vessel for systemic circulation.

Transdermal patches can be applied for both local and for systemic circulation that will be held on the skin for longer periods like EXELON PATCH (rivastigmine transdermal system) Apply patch on intact skin for a 24-hour period; replace with a new patch every 24 hours.

Surprisingly, we have found a novel way to provide a topical product that incorporates both hands free approach for the application and much more efficacy with rapid onset of action at ready to act format for local and systemic treatment. Fast acting: The invention uses readily dissolved version of the drug in solution with penetration enhancers, that can act rapidly for the treatment and provides faster onset of action.

Exact dose: with the airless container metered dose, exact dose can be applied each time through a metered dose system. During application, when it is pumped the exact dose required for treatment.

Hands Free application: When the airless container is pumped, the drug solution is delivered into the applicator, and the drug product can be applied from the applicator to the treatment area without using the hand and will not leave any residue or greasiness d) Patient compliance: With Appod™ all the three doses required for treatment per day can be added all at once in the Appod™, it spreads and continuously delivers for one day treatment without administering 3 times and cloths can we worn Appod™ protect the treatment area and cloths/beds will not get soiled.

It is an object to provide a handheld THADS™ system that includes a topical applicator for dispensing a precise amount of liquid or exact dose and can be applied hands free application on a particular surface such as a skin of a human or animal.

It is an object to provide a THADS™ system that can provide a ready to act product that may act fast compared to conventional ointment, creams and transdermal patches for a single vertical press of the airless container.

It is an object to provide a THADS™ system that can provide a fast acting and administer a topical does once a day application compared to conventional ointment, creams for a single vertical press of airless container and the products pumps into the Appod™.

It is an object to provide a topical applicator with a housing and grip that is ergonomic and help hands free application of a topical product.

It is an object to provide a topical applicator with a liquid delivery system that releases a sufficient amount of liquid upon application onto a surface without producing any blotches or mess.

It is an object to provide a THADS™ system that can provide a, efficacious, multimodal topical method of treatment and prevent soiling of cloths and bed and provide effective dose for treatment effectively.

The following marketed topical products, Aspercreme no mess liquid, Icy Hot no mess applicator, Voltaren Emulgel with no mess applicator and Aleve X roller ball applicator are the topical applicators, these commercial ones are integrated with the container and are pull/push or roll-on mechanism. Roll-on applicators are in common use today. They comprise a container for the liquid and a nozzle having a ball seat and a ball rotatably supported on said seat. To apply the liquid to a selected surface, all that need be done is to invert the container so that its nozzle faces downwardly and said container is then moved across said surface with its ball in rolling contact therewith. The ball becomes coated with the liquid contents of the container and it in turn then coats the selected surface, the container is specially made to receive the nozzle and in some cases the container and nozzle are integral with each other and all these technology does not provide the exact dose or metered dose of drug and the applicator is not flexible to apply difficult to reach parts of the body.

Figure 3:
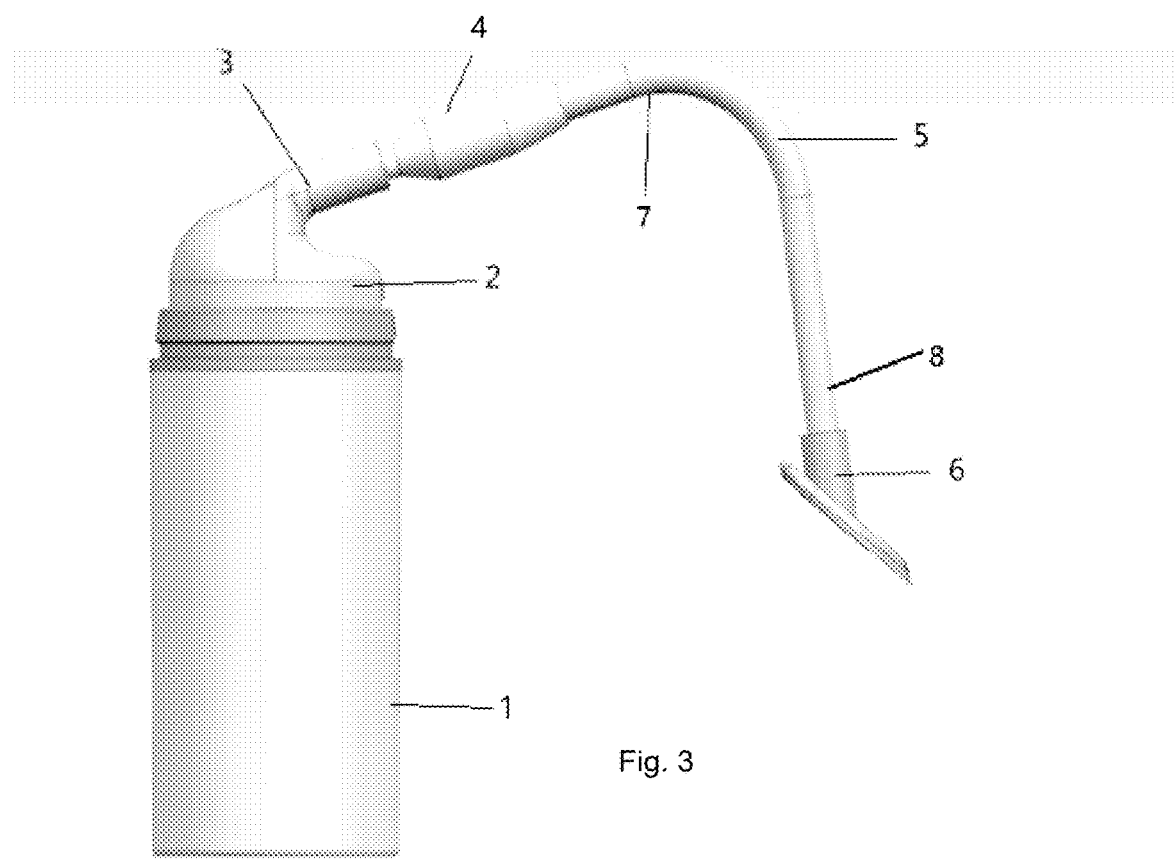
FIG. 3 is an illustration of an Airless, child resistant, metered dose container to hold multiple doses of the topical product with a detachable wand and applicator.

In specific embodiments, the airless container body 1 from FIG. 3, is manufactured using an oil resistant plastic, plastic, metal, or other suitable material such as chemically resistant polypropylene, high density polyethylene, other homopolymers, silicone etc. and hold the drug product in the volume ranges from 0.25 ml to 500 ml as a single dose container or as a multidose container. The airless bottle is a metered dose system to deliver 0.1 ml to 5 ml per pump of the drug solution without back flow from the wand 5, the pumping of drug solution is ergonomically designed, just to press from the top of the cap 2 by palm, especially this process is friendly to arthritis/elderly patient population to deliver pain relief drugs through this airless container system.

The airless container cap 2 from FIG. 3 holds the airless pumping mechanism, that can pump a metered dose of 0.1 mL to 5 mL per pump, child resistant container mechanism and modified nozzle for an adapter that will hold the wand 5 and the applicator sponge tip 6.

The specific embodiment the drug product volume in a form fill seal single unit dose of 0.25 ml to 50 ml and an airless container for a multidose drug product from 2 ml to 500 ml volume, most preferred volume is in between 10 ml to 300 ml for a multidose volume.

In specific embodiment, the cap 2 can directly attached to the applicator sponge 6 without the wand.

In specific embodiment, the cap 2 has a turn in mechanism to operate for a child resistant container.

In specific embodiment, the wand or tube 5 as illustrated in FIGS. 4a and 4b is made up of flexible soft plastic, soft Aluminum, medical grade non-toxic Polyvinyl chloride, Polyethylene, polypropylene. The wand 5 is made it flexible so one can bend the desired shape to apply any curved shape of the body required for treatment. Wand 5 may compose of a metal wire with a thickness of 0.5-1.5 mm, is embedded tube/wand. This metal wire has the specific purpose of allowing the tube to be bent into any shape or U-shape and remain on the shape for application of the drug solution using the sponge tip, then the wand/tube can be straightened out.

FIG. 5 indicates the graph of the pump core, when tested using the CT3 Ametek Texture analyzer, when the bottle with cap is subjected to a compression mode test the pump core exerts a pressure when a load of pressure is constantly applied, the 10 indicates the normal container has the load around 2000 grams, and 11 indicated an improved version of the bottle with a maximum load of around 12000 grams, when normal container of 200 grams load was used it showed the back flow of the drug solution from the wand 5 to the airless bottle, 10 with improved core pump form the graph showed maximum pressure load of 12000 grams, when the drug solution is pumped using 12000 grams load container, there is no back flow from the wand 5 of the drug solution.

In specific embodiments, the texture analyzer data on the pump core 12 is minimum of 2500 grams and maximum of 20,000 grams to prevent the back flow of the liquid product that will be pumped through the wand 5.

Figure 6:
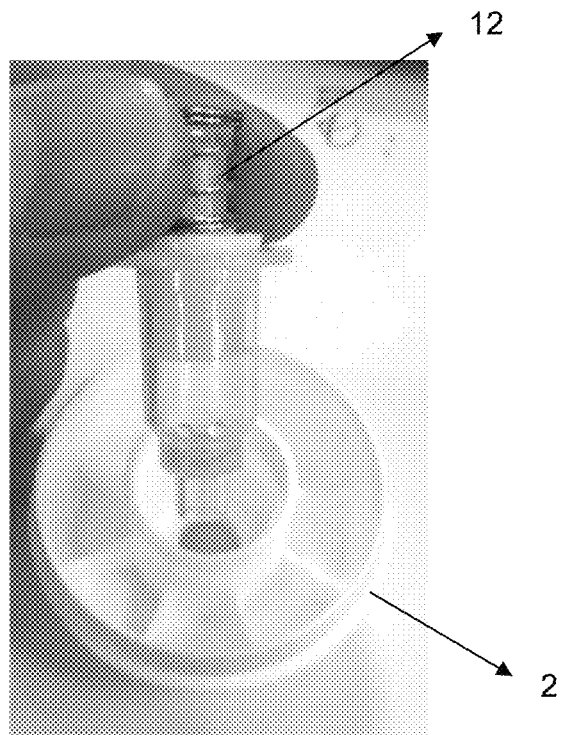
FIG. 6 is a photograph of photograph of a spring in the cap of the airless bottle that will be tested by Texture analyzer graph which prevents the back flow of the solution after pumping it.

In specific embodiments, the cap 2 which include the pump core 12 as shown in FIG. 6 has a minimum tension of 7500 grams when tested the cap tension with the bottle using a CT3 Ametek texture analyzer. This pump core of 7500 grams load prevents the back flow of the drug solution after it gets pumped from the wand back to the airless bottle. In specific embodiments, the applicator adaptor 4, is made up of medical or food grade Poly vinyl chloride, Polyethylene, Silicone, poly propylene, plastic materials, it is a handle to hold the applicator wand and sponge, 4 can have a soft sponge embedded on top of it to provide a soft cushion for hands while connecting and disconnecting it. 13 is a wider hole than that of 14 for the insert of the wand, the fitting on 13 has a notch that locks the wand/applicator sponge into the nozzle of the airless container for an easy application for multiuse applications. The 13 has a snap lock-in mechanism to hold the applicator wand assembly tightly when the solution is pumped. After pumping the solution 13 can pulled to disconnect the wand to apply the drug solution on the skin. The connection can be made using quick connection fittings. The 14 is comparatively smaller opening than 13 is place, this setup prevents the pressure build up while pumping the drug solution from the airless bottle to the applicator wand. The thickness of 4 adaptor is critical to hold it for application, the thickness is critical for arthritis patients, its thickness in this specific embodiment is 10 mm to 30 mm and length of 30 mm to 80 mm.

In specific embodiments, the applicator adaptor 4, is having a luer lock or snap on or push in or twist lock mechanism to lock the applicator with a syringe In specific embodiments, the applicator adaptor 4, the sponge tip 6 can be directly connected without the wand.

In specific embodiments, the applicator adaptor 4, is soft to hold and it lock in and locks out by screw type mechanism or as a snap on mechanism.

Figure 7:
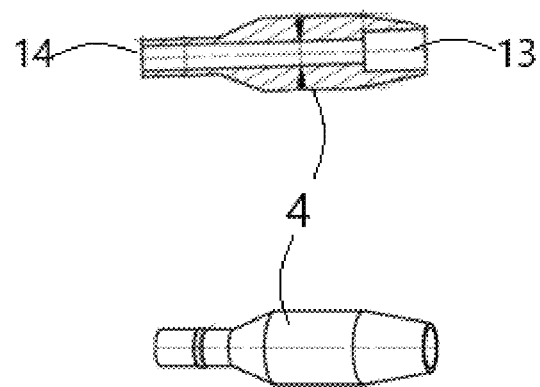
FIG. 7 is an illustration of the applicator adaptor.

In specific embodiment. The airless bottle system may not have the applicator adaptor 4, but the wand 5 will have the built-in adaptor that can attached to the airless bottle or the airless bottle cap 2 will have a built-in adaptor to insert the wand 5, as shown in FIG. 7.

Figure 8:
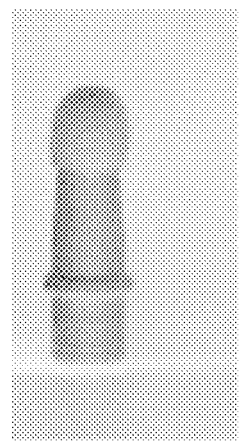
FIG. 8 is an illustration of a nasal applicator.

In specific embodiment, the wand or tube 5 having a first end 7 connectable to an applicator adaptor and second free end 8 connected to the applicator end to which applicator sponge adaptor for topical dosage, nasal applicator as shown in FIG. 8 for nasal drug delivery and rectal applicator/vaginal applicator for rectal/vaginal administration can be attached for its respective application.

In specific embodiment, the wand or tube 5, the end 8 of the wand can be inserted with 6 applicator sponge adaptors for topical application or with 9 for anal application or 10 with for a nasal application and it can be removed and can be administered drugs for oral application, there can be sleeve, which can be a disposable one for oral administration that can be inserted in 8.

In specific embodiment, the applicator sponge adaptor 6 contains a hole through with product can be delivered after pumping the cap 2 of the airless bottle, this allows to pump the drug product directly into the treatment area with or without applicator sponge 16.

In specific embodiment. The applicator sponge adaptor 6 can be directly inserted into the nozzle 3 of the airless bottle and the needed solution can be pumped and applied into the treatment area.

In specific embodiment, the applicator sponge adaptor 6 contains a hole and also 3 to 4 small wheels for a provision for a massage and through which the product can be delivered after pumping the cap 2 of the airless bottle, this allows to pump the drug product directly into the treatment area with or without applicator sponge 16.

Figures 9A, 9B, 9C:
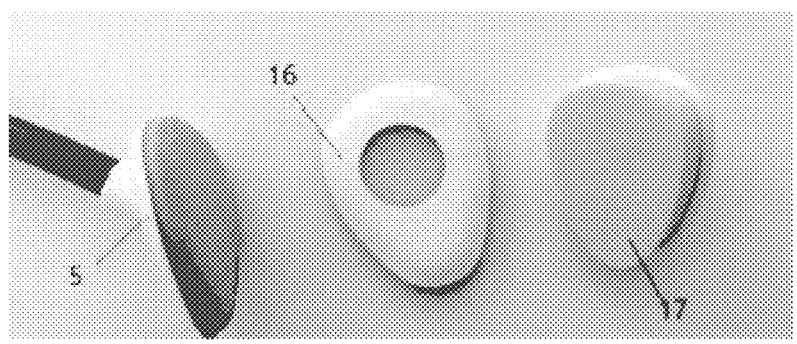
FIGS. 9a-9c are images showing an applicator sponge tip.

In specific embodiment, the applicator sponge 16 is made up of hypoallergenic sponge or foam materials, preferably polyurethane foam, or sponge, it holds the drug product without dripping till applied on to the skin with little pressure. The applicator sponge 16 can be a disposable one and van be shrouded to the applicator sponge adaptor 6 as shown in FIGS. 9a-9c.

In specific embodiment, the applicator sponge 16, when pumped 0.1 mL or 0.1 grams using the metered dose of 0.1 mL, the applicator sponge holds 0.1 mL without dripping and it will release the drug product when the sponge is applied to the skin with little force.

In specific embodiment, the applicator sponge 16, when pumped 0.2 mL or 0.2 grams using the metered dose of 0.2 mL, the applicator sponge hold 0.1 mL without dripping and it will release the drug product when the sponge is applied to the skin with little force.

In specific embodiment, the applicator sponge 16, when pumped 0.25 mL or 0.25 grams using the metered dose of 0.25 mL, the applicator sponge hold 0.25 mL without dripping and it will release the drug product when the sponge is applied to the skin with little force.

In specific embodiment, the applicator sponge 16, when pumped 0.3 mL or 0.3 grams using the metered dose of 0.3 mL, the applicator sponge hold 0.3 mLl without dripping and it will release the drug product when the sponge is applied to the skin with little force.

In specific embodiment, the applicator sponge 16, when pumped 0.35 mL or 0.35 grams using the metered dose of 0.35 mL, the Applicator sponge hold 0.35 mL without dripping and it will release the drug product when the sponge is applied to the skin with little force.

In specific embodiment, the applicator sponge 16, when pumped 0.4 mL or 0.4 grams using the metered dose of 0.4 mL, the Applicator sponge hold 0.4 mL without dripping and it will release the drug product when the sponge is applied to the skin with little force.

In specific embodiment, the applicator sponge 16, when pumped 0.45 mL or 0.45 grams using the metered dose of 0.45 mL, the Applicator sponge hold 0.45 mL without dripping and it will release the drug product when the sponge is applied to the skin with little force.

In specific embodiment, the applicator sponge 16, when pumped 0.5 mL or 0.5 grams using the metered dose of 0.5 mL, the Applicator sponge hold 0.5 mL without dripping and it will release the drug product when the sponge is applied to the skin with little force.

In specific embodiment, the applicator sponge 16, when pumped 0.55 mL or 0.55 grams using the metered dose of 0.55 mL, the Applicator sponge hold 0.55 mL without dripping and it will release the drug product when the sponge is applied to the skin with little force.

In specific embodiment, the applicator sponge 16, when pumped 0.6 mL or 0.6 grams using the metered dose of 0.6 mL, the Applicator sponge hold 0.6 mL without dripping and it will release the drug product when the sponge is applied to the skin with little force.

In specific embodiment, the applicator sponge 16, when pumped 0.65 mL or 0.65 grams using the metered dose of 0.65 mL, the Applicator sponge hold 0.65 mL without dripping and it will release the drug product when the sponge is applied to the skin with little force.

In specific embodiment, the applicator sponge 16, when pumped 0.7 mL or 0.7 grams using the metered dose of 0.7 mL, the Applicator sponge hold 0.7 mL without dripping and it will release the drug product when the sponge is applied to the skin with little force.

In specific embodiment, the applicator sponge 16, when pumped 0.75 mL or 0.75 grams using the metered dose of 0.75 mL, the Applicator sponge hold 0.75 mL without dripping and it will release the drug product when the sponge is applied to the skin with little force.

In specific embodiment, the applicator sponge 16, when pumped 0.8 mL or 0.8 grams using the metered dose of 0.80 mL, the Applicator sponge hold 0.8 mL without dripping and it will release the drug product when the sponge is applied to the skin with little force.

In specific embodiment, the applicator sponge 16, when pumped 0.85 mL or 0.85 grams using the metered dose of 0.85 mL, the Applicator sponge hold 0.85 mL or 0.85 grams without dripping, and it will release the drug product when the sponge is applied to the skin with little force.

In specific embodiment, the applicator sponge 16, when pumped 0.9 mL or 0.9 grams using the metered dose of 0.9 mL, the Applicator sponge hold 0.9 mL or 0.9 grams without dripping, and it will release the drug product when the sponge is applied to the skin with little force.

In specific embodiment, the applicator sponge 16, when pumped 0.95 mL or 0.95 grams using the metered dose of 0.95 mL, the Applicator sponge hold 0.95 mL or 0.95 grams without dripping, and it will release the drug product when the sponge is applied to the skin with little force.

In specific embodiment, the applicator sponge 16, when pumped 1.0 mL or 1.0 grams using the metered dose of 0.1 mL, the Applicator sponge hold 1.0 mL or 1.0 grams without dripping, and it will release the drug product when the sponge is applied to the skin with little force.

In specific embodiment, the applicator sponge 16, when pumped 1.1 mL or 1.1 grams using the metered dose of 0.1 mL, the Applicator sponge hold 1.1 mL or 1.1 grams without dripping, and it will release the drug product when the sponge is applied to the skin with little force.

In specific embodiment, the metered dose pump can pump 0.1 mL to 5 mL per pump, so that it can be utilized for topical application, vaginal application, rectal application, nasal application, and oral administration of drugs.

In specific embodiment, the applicator sponge 16, when pumped 1.25 ml or 1.25 grams using the metered dose of 0.1 mL, the Applicator sponge hold 1.25 mL or 1.25 grams without dripping, and it will release the drug product when the sponge is applied to the skin with little force.

In specific embodiment, the applicator sponge 16, when pumped 1.5 mL or 1.5 grams using the metered dose of 0.1 mL, the Applicator sponge hold 1.5 mL or 1.5 grams without dripping, and it will release the drug product when the sponge is applied to the skin with little force.

In specific embodiment, the applicator sponge 16, when pumped between 0.1 mL or 0.1 grams to 2 mL or 2 grams using the metered dose of between 0.1 mL or 0.1 grams to 2 mL or 2 grams, the Applicator sponge hold 0.1 ml without dripping and it will release the drug product when the sponge is applied to the skin with little force.

In specific embodiment the 6 is wrapped with a sponge 16 and it can be disposable, or it can have a sponge sticking 17 to the 6 as shown in FIGS. 9a-9c.

Figure 10A:
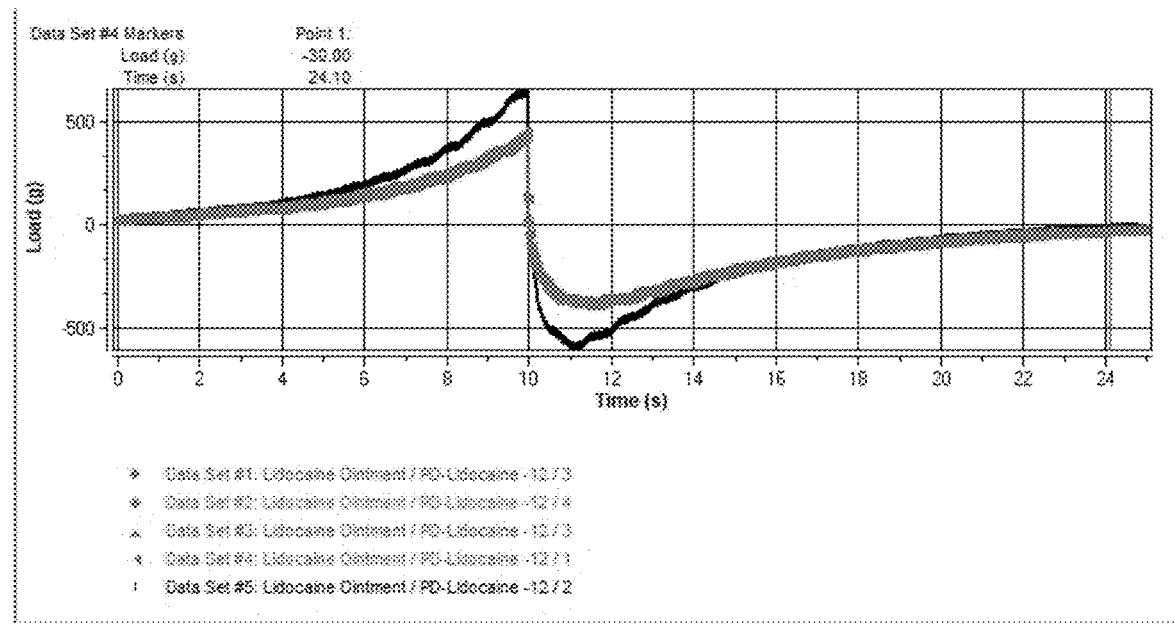
FIG. 10a is is texture analyzer graph on the texture of the lidocaine ointment.
Figure 10B:
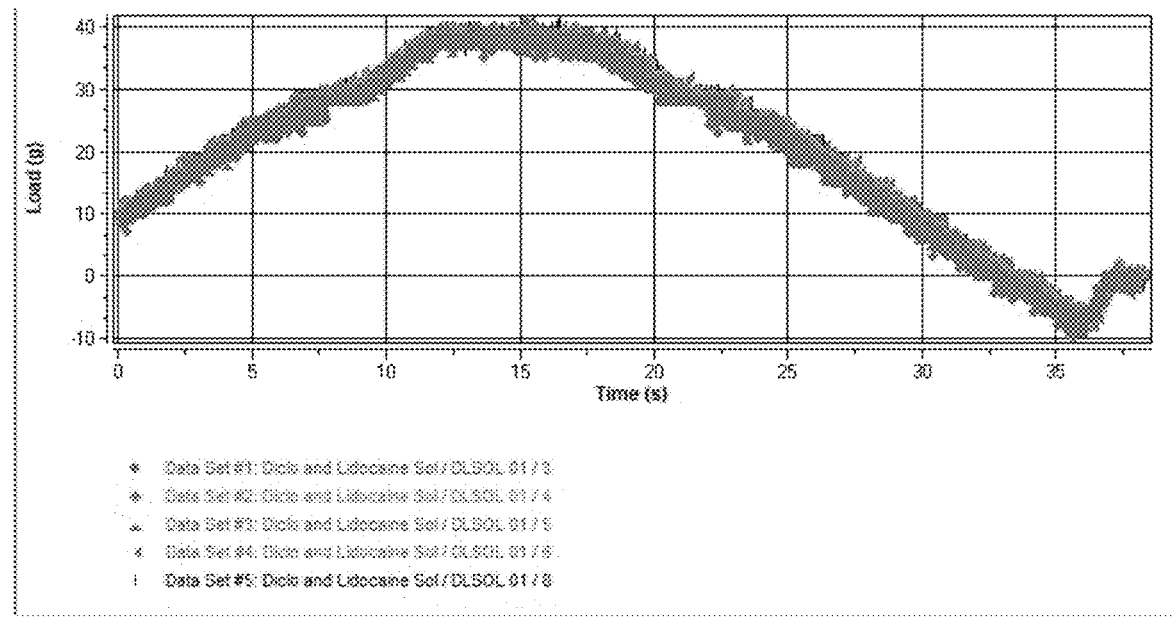
FIG. 10b is is texture analyzer graph on the texture of the THADS™ Dicclofenac/lidocaine solution.

The graphs from FIGS. 10a and 10b illustrate the topical products texture testing shows the load of 450 grams to 600 grams from the FIG. 10a for the conventional ointment, which needs hands to spread it, with this high load of above 400 grams can't be used in the Appod™. The load of around 40 grams from the FIG. 10b for THADS product of Diclofenac and Lidocaine solution when tested using Brookfield Ametek CT3 Texture analyzer, using probe TA-11 at the following settings, Test type: Compression, Test Target: Distance with Target value of 15 mm and target load of 10 grams with test speed of 1.0 mm/second. The lower the load of less than 100 grams will enable the THADS™ product to spread itself through the inner non-woven fabric of the Appod™ for an efficient and hands-free topical treatment.

In specific embodiments texture testing load on the THADS™ drug product less than 100 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 90 grams to 100 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 80 grams to 90 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 70 grams to 80 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 60 grams to 70 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 60 grams to 50 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 50 grams to 60 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 50 grams to 60 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 40 grams to 50 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

In specific embodiments texture testing load on the THADS™ drug product less than 30 grams to 40 grams tested using Brookfield Ametek CT3 Texture analyzer, using probe TA-11 at the following settings, Test Type: Compression, Test Target: Distance with Target value of 15 mm and target load of 10 grams with test speed of 1.0 mm/second is preferable to use in Appod™.

Figure 11:
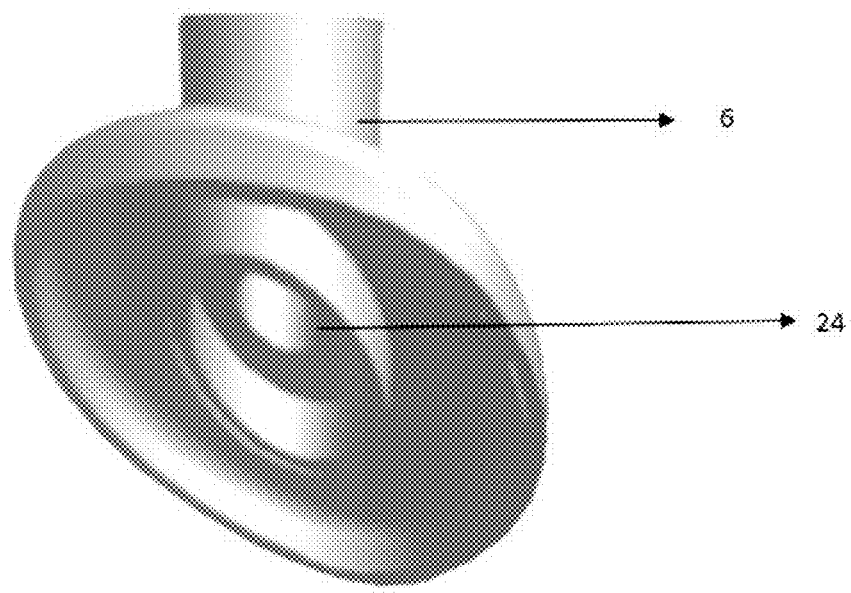
FIG. 11 is a bottom view of the hosing to hold the sponge tip.
Figure 12:
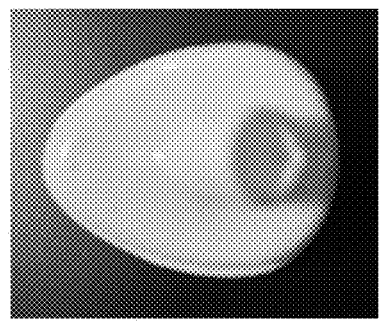
FIG. 12 is is a top view of the hosing to hold the sponge tip.

FIGS. 11 and 12 illustrate the applicator sponge adaptor 6, in which the wand end 8 get inserted, when the topical product is pumped using the cap 2, the drug product after pumped from the container, it travels through the wand 5 and through the hole 24 in the applicator sponge adaptor, it is collected the applicator sponge. If the THADS™ solution texture analyzer load is less than 100 grams by testing using Brookfield Ametek CT3 Texture analyzer, using probe TA-11 at the following settings, Test Type: Compression, Test Target: Distance with Target value of 15 mm and target load of 10 grams with test speed of 1.0 mm/second. The THADS solution will soak into the sponge.

Figure 13:
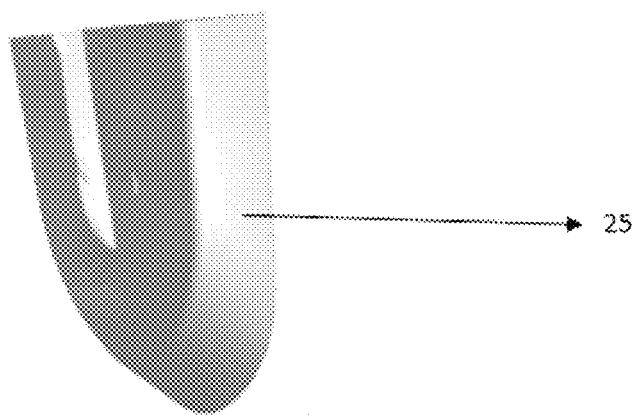
FIG. 13 is an illustration of a cover for the sponge tip.

FIG. 13 is the cover 25 that can be inserted to cover up the applicator sponge from dust and any external contamination for multiple use, the 25 has 'U' shaped grove, that is inserted into the neck of the applicator sponge adaptor 6 where it is gets locked. The grove on the 25 locks into the neck of the sponge applicator adaptor 6.

In a specific embodiment the cover 25 for the sponge tip locks into the sponge applicator adaptor and protects the sponge tip from the dust and other external contaminants.

Figure 14:
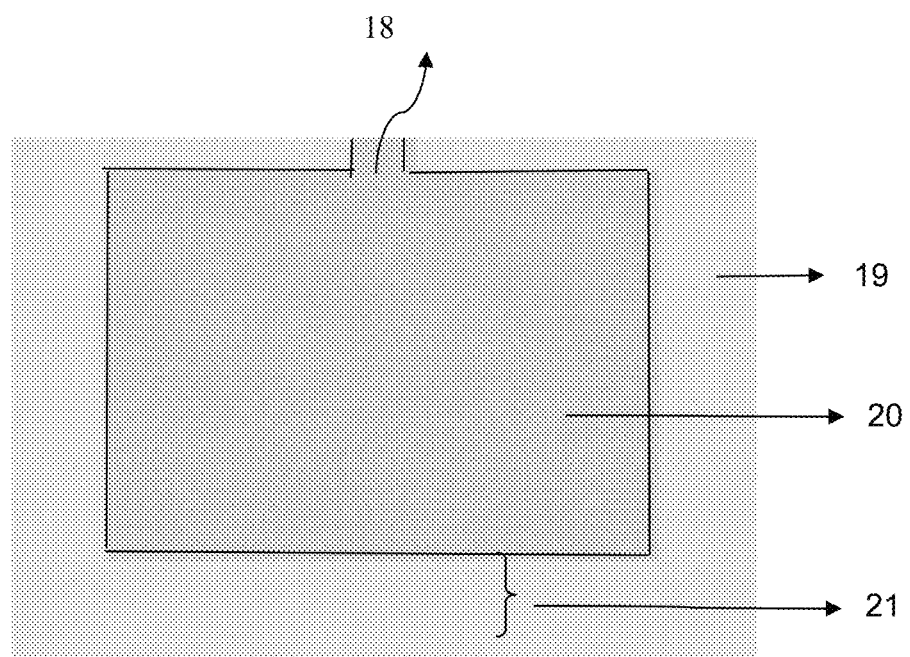
FIG. 14 is an illustration of a perspective view of applicator pod (Appod™).

FIG. 14 illustrates an application pod which will be called as an Appod™, that will be adhered to the skin or the treatment area for a treatment period of 0.1 hours, to few hours, to multiple days and months, if needed Appod™ can be replaced hourly, or every 4 hours or every 12 hours or every 24 hours or every 2 days or every week or every month, Appod™ is a pod or reservoir or a system that will spread and hold the ready to act topical product(s) in which the topical product solution or suspension or emulsion or cream, or gel or an ointment can be added or pumped using a metered dose by airless bottle 1 from FIG. 3. The Appod™ makes the drug product to spread uniformly and held for the treatment period and can be utilized for immediate application and for extended duration of application. FIG. 14 illustrates that the appod has an inlet 18 to add or pump the drug product solution, An outer polymeric fabric 19 is the top layer and provides the various shape/structure and holds all the components of the Appod™, followed by the inner non-woven fabric/pad 20 that spread or hold the added drug product and keeps the drug product very close contact to the skin, part of the outer polymeric fabric 19 on the outer or periphery or border of it includes adhesive area 21 that adheres to the skin surface and hold the Appod™ to the treatment area during its treatment period In some embodiments the Appod™ system that shown in FIG. 14, the outer polymeric fabric 19 includes 10 to 100% area of Appod™ with hypoallergenic adhesive that adheres to the skin.

In some embodiments the Appod™ system that shown in FIG. 14, the outer polymeric fabric 19 includes less than 80% area of Appod™ with hypoallergenic adhesive that adheres to the skin.

In some embodiments the Appod™ system that shown in FIG. 14, the outer polymeric fabric 19 includes less than 70% area of Appod™ with hypoallergenic adhesive that adheres to the skin.

In some embodiments the Appod™ system that shown in FIG. 14, the outer polymeric fabric 19 includes less than 60% area of Appod™ with hypoallergenic adhesive that adheres to the skin.

In some embodiments the Appod™ system that shown in FIG. 14, the outer polymeric fabric 19 includes less than 50% area of Appod™ with hypoallergenic adhesive that adheres to the skin.

In some embodiments the Appod™ system that shown in FIG. 14, the outer polymeric fabric 19 includes less than 40% area of Appod™ with hypoallergenic adhesive that adheres to the skin.

In some embodiments the Appod™ system that shown in FIG. 14, the outer polymeric fabric 19 includes less than 30% area of Appod™ with hypoallergenic adhesive that adheres to the skin.

In some embodiments the Appod™ system that shown in FIG. 14, the outer polymeric fabric 19 includes less than 20% area of Appod™ with hypoallergenic adhesive that adheres to the skin.

In some embodiments the Appod™ system that shown in FIG. 14, the outer polymeric fabric 19 includes less than 15% area of Appod™ with hypoallergenic adhesive that adheres to the skin.

In some embodiments the Appod™ system the shown in FIG. 14 includes 10 to 90% area of Appod™ with hypoallergenic adhesive that adheres to the skin.

In some embodiments the Appod™ system the shown in FIG. 14 includes 10 to 80% area of Appod™ with hypoallergenic adhesive that adheres to the skin.

In some embodiments the Appod™ system the shown in FIG. 14 includes 10 to 70% area of Appod™ with hypoallergenic adhesive that adheres to the skin.

In some embodiments the Appod™ system the shown in FIG. 14 includes 10 to 60% area of Appod™ with hypoallergenic adhesive that adheres to the skin.

In some embodiments the Appod™ system the shown in FIG. 14 includes 10 to 50% area of Appod™ with hypoallergenic adhesive that adheres to the skin.

In some embodiments the Appod™ system the shown in FIG. 14 includes 10 to 40% area of Appod™ with hypoallergenic adhesive that adheres to the skin.

In some embodiments the Appod™ system the shown in FIG. 14 includes 10 to 30% area of Appod™ with hypoallergenic adhesive that adheres to the skin.

In some embodiments the Appod™ system the shown in FIG. 14 includes 10 to 20% area of Appod™ with hypoallergenic adhesive that adheres to the skin.

In some embodiment, the inlet 18 is between 0.25 mm to 100 mm in diameter to add the ready of act solution, suspension, gel, ointment, foam, cream, emulsion for the treatment.

In some embodiment, the inlet 18 is between 2 mm to 50 mm in diameter to add the ready of act solution, suspension, gel, ointment, foam, cream, emulsion for the treatment.

In some embodiment, the inlet 18 is between 5 mm to 12 mm in diameter to add the ready of act solution, suspension, gel, ointment, foam, cream, emulsion for the treatment.

In some embodiment, the inlet 18 is between 6 mm to 10 mm in diameter to add the ready of act solution, suspension, gel, ointment, foam, cream, emulsion for the treatment.

Figure 15:
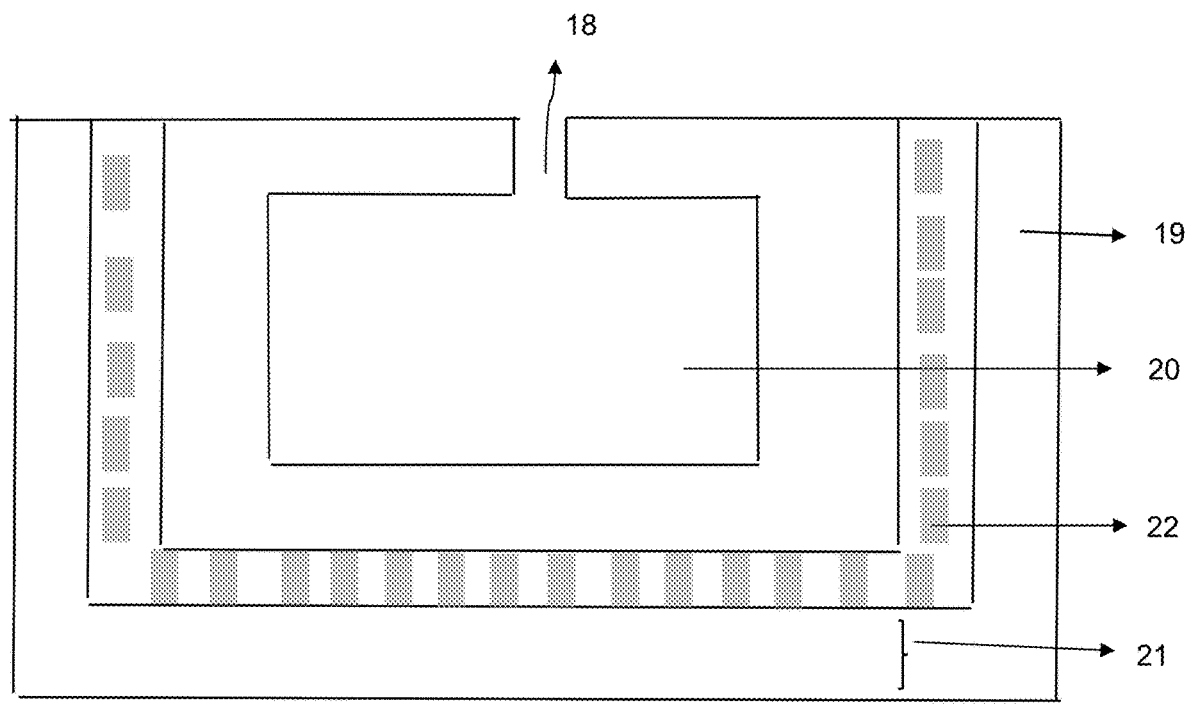
FIG. 15 is is an illustration of a perspective view Appod™ with leak protection.

FIG. 15 illustrates an Appod™ that has additional protection pad 22, that absorbs the extra solution that might be seeping out of the area of the inner non-woven fabric 20, to prevent the adhesive area to be compromised by the different solvents or solution from the topical product by dissolving the adhesive, which may result in the seeping drug solution out of the Appod™.

As shown in FIGS. 14 and 15, the border 21 contains the adhesive material in the periphery of the Appod™, that will seal of the border areas of the APPOD™, which will hold the ready to act solution inside the Appod™ from leaking. The protective layer 22 includes highly absorbent material to absorb the excess ready to act solution from the non-woven fabric, so that this protective layer will prevent the ready to act solution reaching the adhesive and prevent any compromise of the adhesiveness of the APPOD™. The FIGS. 14 and 15 Appod™ may be in the form of a generally available rectangular shape, However, other embodiments of the FIG. 15 may have different shapes like circular, heart shape, triangle and uncommon shapes represent various configuration of the body and configurations for different placements on the skin, and for use by persons of different sizes.

TABLE 3

| | % Drug dissolved | | |
|---|---|---|---|
| | 5 min | 10 min | 15 min |
| Icy Hot patch | 6.3 | 7.9 | 74.8 |
| THADS ™ Lidocaine | 85 | 96.0 | 96.2 |

Figure 16:
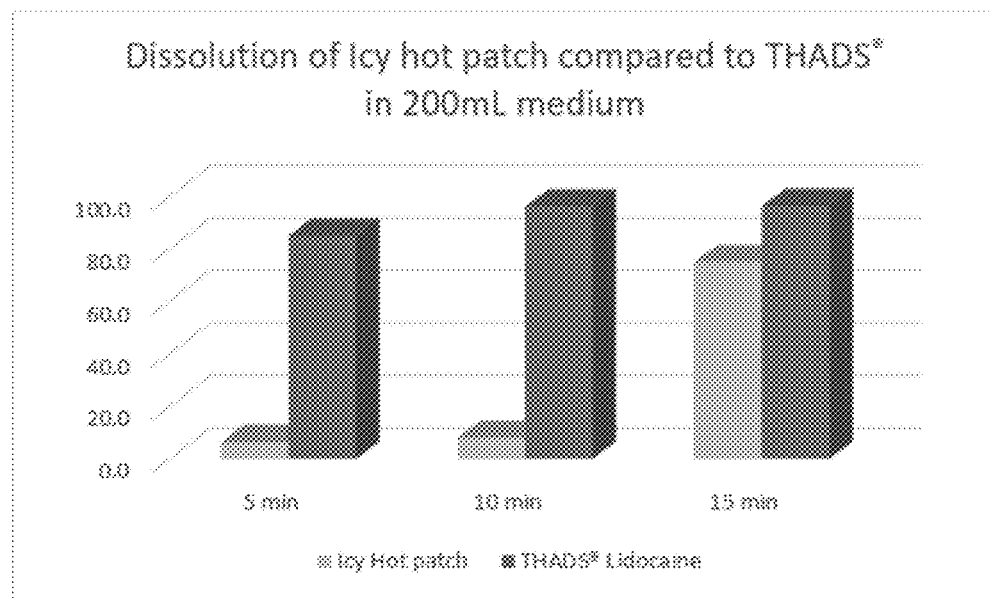
FIG. 16 is a graph of dissolution of icy hot patch compared to THADS™.

FIG. 16 Illustrates the dissolution testing of the Lidocaine in the Appod™ with the marketed Icy Hot patch that contains Lidocaine 4% and Menthol 1% and by testing dissolution using USP Apparatus 5 (paddle over disk method), Purified water as the dissolution medium, 200 mL volume per vessel was used. The temperature was maintained at 32±0.5° C. a distance of 25±2 mm between the paddle blade and the surface of the disk assembly was maintained. The rotation speed was set at 50 rpm. The dissolution data shows that the THADS™ Lidocaine product releases 85% of drug in 5 minutes of dissolution, whereas the Marketed Icy Hot patches released only 6.3% of the drug. This dissolution indicates THADS™ solution in the Appod™ is in ready to act state, whereas the marketed product is of low dissolution this is due to the drug is mixed with the adhesive. The application of THADS™ product with Appod™ will provide "rapid onset" of action compared to the marketed product. THADS™ Appod™ the inner non-woven fabric just spreads and holds the drug solution also the dissolution data shows that the non-woven fabric does not hold back the drug.

In specific embodiments, the Appod™ loaded drug will release above 30% of drug in 5 minutes by testing dissolution using USP Apparatus 5 (paddle over disk method), with purified water as the medium volume, 200 mL per vessel. The temperature is maintained at 32±0.5° C. a distance of 25±2 mm between the paddle blade and the surface of the disk assembly. The rotation speed was set at 50 rpm.

In specific embodiments, the Appod™ loaded drug will release above 40% of drug in 5 minutes by testing dissolution using USP Apparatus 5 (paddle over disk method), with purified water as the medium volume, 200 ml per vessel. The temperature is maintained at 32±0.5° C. a distance of 25±2 mm between the paddle blade and the surface of the disk assembly. The rotation speed was set at 50 rpm.

In specific embodiments, the Appod™ loaded drug will release above 50% of drug in 5 minutes by testing dissolution using USP Apparatus 5 (paddle over disk method), with purified water as the medium volume, 200 mL per vessel. The temperature is maintained at 32±0.5° C. a distance of 25±2 mm between the paddle blade and the surface of the disk assembly. The rotation speed was set at 50 rpm.

In specific embodiments, the Appod™ loaded drug will release above 60% of drug in 5 minutes by testing dissolution using USP Apparatus 5 (paddle over disk method), with purified water as the medium volume, 200 mL per vessel. The temperature is maintained at 32±0.5° C. a distance of 25±2 mm between the paddle blade and the surface of the disk assembly. The rotation speed was set at 50 rpm.

In specific embodiments, the Appod™ loaded drug will release above 70% of drug in 5 minutes by testing dissolution using USP Apparatus 5 (paddle over disk method), with purified water as the medium volume, 200 ml per vessel. The temperature is maintained at 32±0.5° C. a distance of 25±2 mm between the paddle blade and the surface of the disk assembly. The rotation speed was set at 50 rpm.

In specific embodiments, the Appod™ loaded drug will release above 80% of drug in 5 minutes by testing dissolution using USP Apparatus 5 (paddle over disk method), with purified water as the medium volume, 200 mL per vessel. The temperature is maintained at 32±0.5° C. a distance of 25±2 mm between the paddle blade and the surface of the disk assembly. The rotation speed was set at 50 rpm.

In specific embodiments, the Appod™ loaded drug will release above 90% of drug in 5 minutes by testing dissolution using USP Apparatus 5 (paddle over disk method), with purified water as the medium volume, 200 mL per vessel. The temperature is maintained at 32±0.5° C. a distance of 25±2 mm between the paddle blade and the surface of the disk assembly. The rotation speed was set at 50 rpm.

Figure 17:
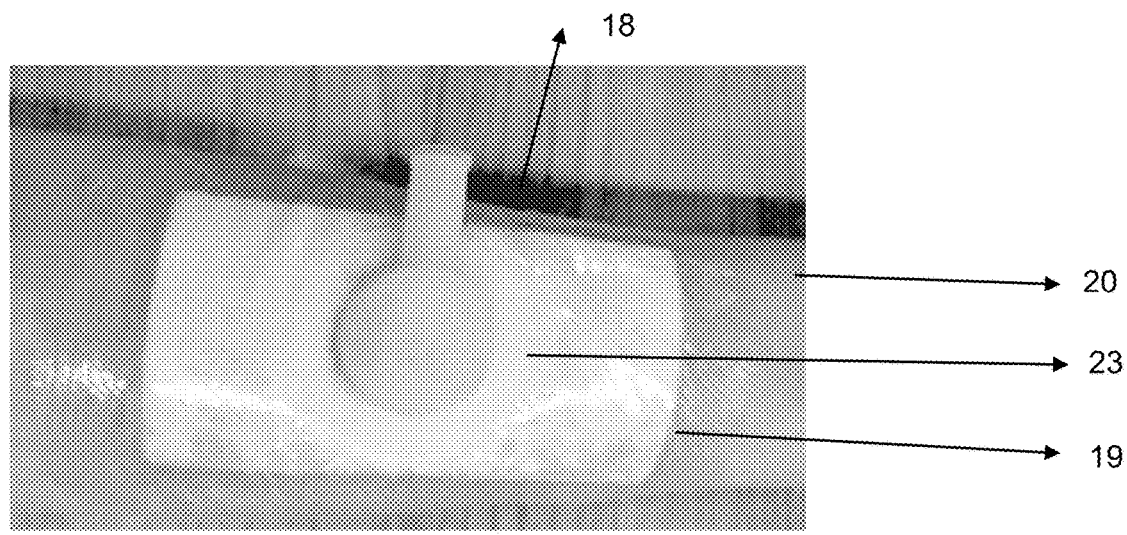
FIG. 17 is a photograph of an Appod™ adhered to arm.

FIG. 17 illustrates an Appod™ includes a reservoir pod 23, which allows easy way to add or pump drug solution into the Appod™ and also it can hold the drug solution and release over a period of time. When the solution was added inlet of the reservoir pod, the solution gets into the inner non-woven fabric 20 and spread the entire area and keeps the drug constantly to the skin where Appod™ is applied for treatment. The reservoir pod allows to keep the Appod™ for longer period of time may be for a day or for two days or for a week or for a moth and just keep adding the drug solution though the inlet of the reservoir pod 23.

Figure 18:
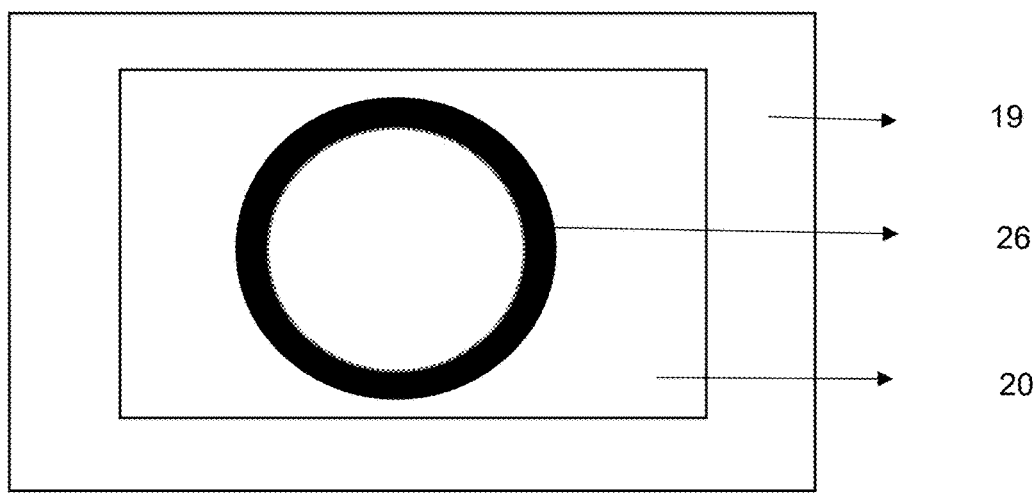
FIG. 18 is an illustration of a perspective view Appod™ with Ethyl Vinyl Acetate ring to deliver drug to specified area of the skin.

FIG. 18 illustrates an Appod™ with an isolation ring 26 at the middle made up of polymer, so that the drug solution can be contained within the ring to maintain the specific area of treatment. The inside of the isolation ring can have a non-woven fabric or may openly expose the skin area intended for treatment like surgery and wounds etc. The isolation ring 26 contains the drug solution within the ring area.

In some embodiments the Appod™ system the isolation ring 26 is non absorbing and it is made up of silicone, Ethyl vinyl acetate and does not sensitize or irrigate the skin.

In some embodiments the Appod™ system the isolation ring 26 is non absorbing and is 1 cm to 19 cms in diameter.

In some embodiments the Appod™ system the isolation ring 26 is non absorbing and is 2 cm to 4 cms in diameter.

In some embodiments the Appod™ system the isolation ring 26 is non absorbing and is 4 cm 6 cms in diameter.

In some embodiments the Appod™ system the isolation ring 26 is non absorbing and is 6 cm to 8 cms in diameter.

In some embodiments the Appod™ system the isolation ring 26 is non absorbing and is 8 cm to 10 cms in diameter.

In some embodiments the Appod™ system the isolation ring 26 is non absorbing and is 10 cm to 12 cms in diameter.

In some embodiments the Appod™ system the isolation ring 26 is non absorbing and is 12 cm to 14 cms in diameter.

In some embodiments the Appod™ system the isolation ring 26 is non absorbing and is 14 cm to 16 cms in diameter.

In some embodiments the Appod™ system the isolation ring 26 is non absorbing and is 16 cm to 18 cms in diameter.

In some embodiments the Appod™ system the isolation ring 26 is non absorbing and is 18 cm to 20 cms in diameter.

Figure 19:
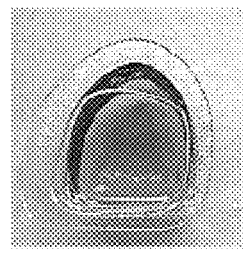
FIG. 19 is an image of a pouch filled with the THADS™ solution.

In some embodiments, the Appod™ system the isolation ring 26 has spikes so that the THADS drug product solution can be filled in the pouch of FIG. 19 and adhered to the top layer of reservoir pod 23 or outer polymeric fabric 19 as a unit dose for once-a-day application or for more than one a day application. After applying the Appod™ into the skin of the treatment area, by tapping the top part of the Appod™ by hand the pouch of FIG. 19 gets ruptured by the spike in the isolation ring and the drug product solution is released for its activity within the Appod™.

In some embodiments, the Appod™ system the pouch showed in FIG. 19 is made up of very soft, flexible materials like silicone, Polyethylene, polypropylene, or polyethylene/polypropylene co-polymers and can be in different shapes and can hold 0.25 mL to 10 mL per pouch.

In some embodiments, the Appod™ system the pouch showed in FIG. 19 is sterile.

In some embodiments, the Appod™ system the pouch showed in the FIG. 19 is sterile used to treat pain after surgery, infections, wounds, and burns.

In some embodiments, the Appod™ system the pouch showed in the FIG. 19 can hold 0.1 mL to 12 mL of drug product solution, suspension, or emulsion.

In some embodiments, the Appod™ system the pouch showed in the FIG. 19 can hold 0.5 mL to 2 mL of drug product solution, suspension, or emulsion.

In some embodiments, the Appod™ system the pouch showed in the FIG. 19 can hold 2 mL to 4 mL of drug product solution, suspension, or emulsion.

In some embodiments, the Appod™ system the pouch showed in the FIG. 19 can hold 4 mL to 7 mL of drug product solution, suspension, or emulsion.

In some embodiments, the Appod™ system the pouch showed in the FIG. 19 can hold 7 mL to 10 mL of drug product solution, suspension, or emulsion.

Figure 20:
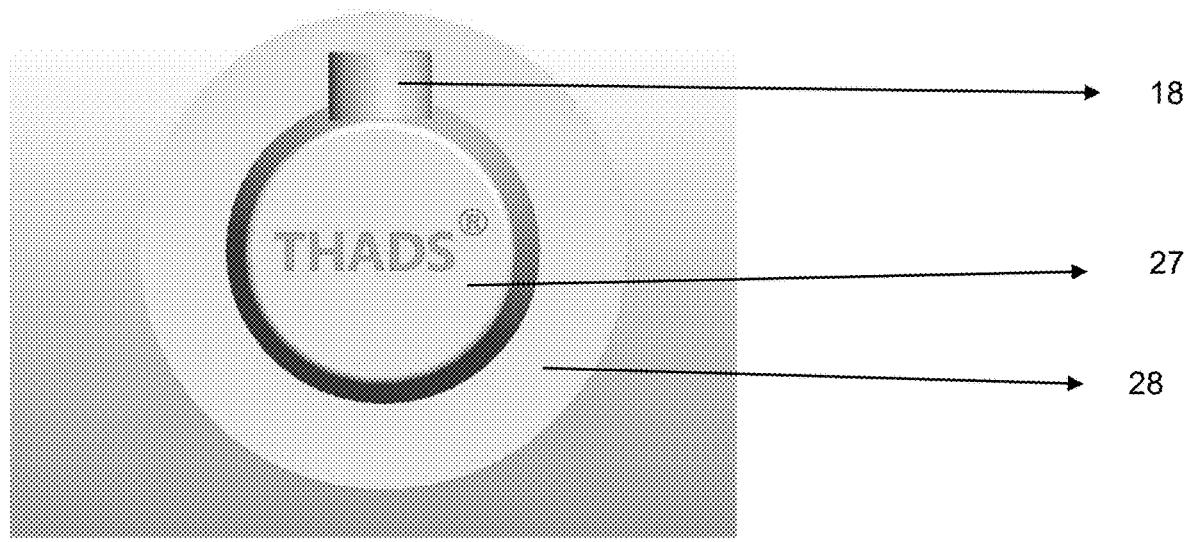
FIG. 20 is a silicone dome a part of an Appod™ embossed with THADS™ logo.

FIG. 20 illustrates the top view of the reservoir pod 23, which has an inlet 18 for the drug product solution, which can be added from the airless bottle wand 5. The reservoir pod 23 has an elevated dome 27 and a collar 28 extending outwards. The collar 28 was adhered to the outer layer Polyurethane film 19, beneath the reservoir dome 23 will be the inner non-woven fabric 20 or in some case it will be the isolation ring 26.

Figure 21:
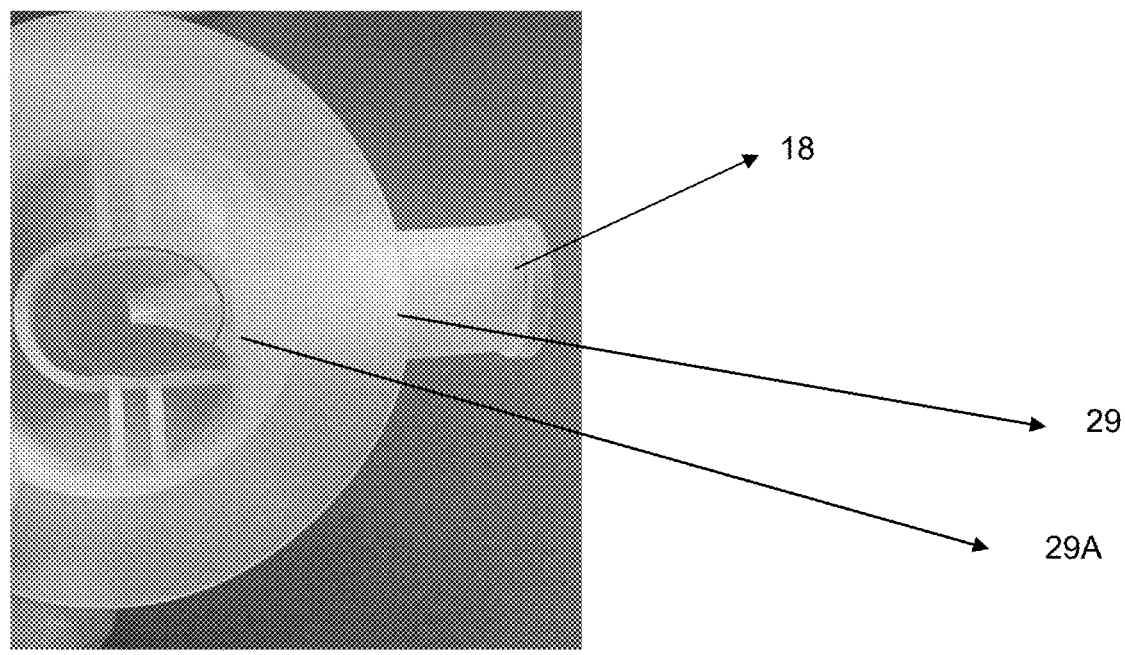
FIG. 21 is is a cross sectional view of the silicone dome that shows the duckbill valve to prevent the back flow of liquids.

FIG. 21 illustrates the bottom or cross section view of the reservoir pod 23, the bottom part includes a duckbill valve 29 to prevent the back flow of the added solution from the reservoir or from the Appod™ and 29A, a wall to stop the further advancement of the wand 5 while pumping the drug product. in some instance the dome wall 27 of the will act like a wand stopper like 29A.

In some embodiments the Appod™ system has a back flow prevention with the reservoir pod 23 like Duckbill vale as shown in FIG. 21 or a screw cap on the inlet tube 18 or a snap on lid attached to the inlet tube 18 or a plug that can be used to close the inlet and prevent back flow of the added drug product solution.

In specific embodiments the reservoir pod 23, has embossing on top of it as THADS™ or other name on it.

In some embodiments the Appod™ system the reservoir pod 23 is made up of very flexible and ductile materials preferable silicone, so that it is light weight and modulate the body curvatures as flexible so that it will not feel its presence or pinching effect while sleeping.

In some embodiments the Appod™ system the reservoir pod 23 is made up of flexible polymer or a non-flexible polymer with a wall thickness of 0.1 mm to 30 mm, preferable 0.2 mm to 10 mm.

In some embodiments the Appod™ system the reservoir pod 23 act as a reservoir or pod and holds 0.1 ml to 50 ml of drug solution preferably from 0.25 mL to 10 mL.

In some embodiments the Appod™ system the reservoir pod 23 act as a reservoir or pod and has a capillary delivery at the bottom of the reservoir pod 23 for the drug solution to pass through porous ceramic wick to the skin in a predetermined control flow rate.

In some embodiments the Appod™ system the reservoir pod 23 ceramic wick is not soluble in water or in ethanol, methanol, propylene glycol, Dimethyl sulfoxide, ethyl acetate, and isopropyl alcohol.

In some embodiments the Appod™ system the reservoir pod 23 the flow control wick can be made up of fibers like Cotton, jute, paper, or rayon.

In some embodiments the Appod™ system the reservoir pod 23 act as a reservoir or pod and has a capillary delivery of the drug solution through porous ceramic wick to the skin and flow is controlled to 0.001 mL/hour to 1 mL/hour for extended hours of time.

In some embodiments the Appod™ system the reservoir pod 23 act as a reservoir or pod and has a passive capillary delivery of the drug solution through porous sintered particles and bonded fabric.

In some embodiments the Appod™ system the reservoir pod 23 act as a reservoir or pod and the drug solution is actively controlled the flow using by pumping the drug product through a piezoelectric micro pump or peristaltic micro pump.

In some embodiments the Appod™ system the reservoir pod 23 act as a reservoir or pod and the drug solution is actively controlled by peristaltic micro pump manufactured by Takasago RP-Q1.2N-P20Z.

In some embodiments the Appod™ system the reservoir pod 23 act as a reservoir or pod and the drug solution is actively controlled by a piezoelectric micro pump manufactured by Bartel mp6.

In some embodiments the Appod™ system the reservoir pod 23 act as a reservoir or pod and the drug solution is pumped through a piezoelectric micro pump or peristaltic micro pump and flow is controlled to 0.001 mL/hour to 1 mL/hour for extended hours of time or for 3 times a day through an electronic process control mother board that can be easily controlled and locked by care giver, pharmacist, doctor, nurse, or the consumer.

In some embodiments the Appod™ system the reservoir pod 23 act as a reservoir or pod can deliver 0.01 mL to 1.0 mL/hour of the drug solution to the treatment area of the skin through the capillary wick, sintered material or bonded fabric or using a micro pump. In some embodiments the Appod™ system the reservoir pod 23 act as a reservoir or pod can deliver 0.01 mL to 1.0 mL/hour of the drug solution to the treatment area of the skin through the combination of the passive capillary wick, sintered material or bonded fabric and active flow control by using a micro pump.

In specific embodiments the a second flexible reservoir is provided within the Appod™ for housing a volume of same drug or second drug for bolus dose delivery to the user or synergistic treatment or multi-model drug delivery system. The pre-programmed Appod™ pump can be programmed either by the manufacturing facility or a health care provider and preferably requires no additional user programming to deliver the drug in a periodic time for multiple days.

In some embodiments, the outer polymer fabric layer 19 is a nonwoven fabric layer. In some embodiments, the polymer fabric layer 19 is a non-woven fabric includes at least one of a polyurethane film, a polyolefins film, a polyesters film, a polyalkylenes film, a polyamides film, a polystyrenes film, a polyarylsulfones film, a polydienes film, a polyethylene film, a polypropylene film or, a PVC film, the 19 can be a nonwoven material, and/or a woven material.

In some embodiments, the Outer polymeric fabric layer 19 is highly breathable and/or porous, making the THADS™ Appod™ comfortable to wear.

In some embodiments, the Outer polymeric fabric layer 19 is colorless and transparent.

In some embodiments, the Outer polymeric fabric layer 19 is in skin color shades.

In some embodiments, the Outer polymeric fabric layer 19 is in multicolor shades.

In some embodiments, the Outer polymeric fabric layer 19 is polyurethane film.

In some embodiments, the Outer polymeric fabric layer 19 is polyurethane film and upon another layer of polymer film to have a colorful design on it.

In some embodiments of the invention, the Outer polymeric fabric layer 19 may be a polyurethane film having a thickness in the range of 5-450 microns, preferably, 10-150.

In some embodiments of the invention, the Outer polymeric fabric layer 19 may be a polyurethane film having a thickness in the range of 5-450 microns, preferably, 10-80 microns.

In some embodiments of the invention, the Outer polymeric fabric layer 19 may be a polyurethane film having a thickness in the range of 5-450 microns, preferably, 10-50 microns.

In some embodiments of the invention, the Outer polymeric fabric layer 19 may be a polyurethane film having a thickness in the range of 5-450 microns, preferably 20 to 35 microns.

In some embodiments, the Outer polymeric fabric layer 19 is highly stretchable and elastic in nature, preferable polyurethane, and combination of Polyurethane and other resins/polymers, so that it can applied to the highly movement required areas like knees and elbows.

In some embodiments of the invention, the Outer polymeric fabric layer 19 may be a polyurethane film having a thickness in the range of 5-450 microns, has 100% adhesive area, so that it can adhere to the skin for a treatment period.

In some embodiments of the invention, the Outer polymeric fabric layer 19 may be a polyurethane film having a thickness in the range of 5-450 microns, has 80% to 60% adhesive area, so that it can adhere to the skin for a treatment period.

In some embodiments of the invention, the Outer polymeric fabric layer 19 may be a polyurethane film having a thickness in the range of 5-450 microns, has 60% to 40% adhesive area, so that it can adhere to the skin for a treatment period.

In some embodiments of the invention, the Outer polymeric fabric layer 19 may be a polyurethane film having a thickness in the range of 5-450 microns, has 40% to 20% adhesive area, so that it can adhere to the skin for a treatment period.

In some embodiments, the Outer polymeric fabric layer 19 is liquid-impervious, moisture-vapor permeable polymeric films include synthetic organic polymers including, but not limited to: polyurethanes, poly-amide block copolymers, poly-ester block copolymers. The polymeric films can be made of one or more types of monomers (e.g., copolymers) or mixtures (e.g., blends) of polymers.

In some embodiments, the Outer polymeric fabric layer 19 composed of non-woven fabric, including polyester, polypropylene, viscose, cotton, rayon, and blended nonwoven fabrics. The blended nonwoven fabrics, including: Cotton/Rayon, Fine Denier Polyester/Course Denier Polyester, Polyester/Rayon. The blend ratio an 90/10 to 10/90 of any two fibers or resins that can include Acrylics, Vinyl Acetate (VAC), Vinyl Acrylics, Ethylene Vinyl Acetate (EVA), Styrene Butadiene Rubber (SBR), Starch, Poly Vinyl Chloride (PVC).

In some embodiments, the Outer polymeric fabric layer 19 includes adhesive, this adhesive adheres the Appod™ to the skin for the treatment area.

In specific embodiment inner non-woven fabric/pad 20 material includes adhesive, this adhesive adheres the Appod™ to the skin for the treatment area.

In specific embodiment inner non-woven fabric/pad 20 material is selected from the group including a polymeric foam, a non-woven material, a fibrous material, a gel forming fiber, a hydrogel, a matrix containing hydrocolloids, a woven fiber, and a knitted fiber.

In specific embodiment inner non-woven fabric/pad 20 is perforated and highly porous in nature and can adsorb the liquid.

In specific embodiment inner non-woven fabric/pad 20 is perforated and highly porous in nature and may adsorb the liquid.

In specific embodiment inner non-woven fabric/pad 20 is perforated and highly porous in nature and may not absorb the liquid.

In specific embodiment inner non-woven fabric/pad 20 is perforated and highly porous, it spreads the added drug product solution within the Appod™

In specific embodiment inner non-woven fabric/pad 20 is perforated and highly porous, it spreads the added drug product solution and holds the drug product for treatment period within the Appod™.

In specific embodiment inner non-woven fabric/pad 20 is perforated and highly porous, multiple layers of the non-woven fabric/pad 20 can be added into the Appod™, to control the drug delivery rate and the treatment period.

In specific embodiment inner non-woven fabric/pad 20 does not contain adhesive.

In specific embodiment inner non-woven fabric/pad 20 may contain adhesive, that helps to adhere to the skin.

In specific embodiment inner non-woven fabric/pad 20 thickness is from 30 grams/m$^2$ to 950 grams/m$^2$ and it is non swellable and it can be one or multilayered fabric.

In specific embodiment inner non-woven fabric/pad 20 thickness is from 30 grams/m$^2$ to 600 grams/m$^2$ and it is non swellable and it can be one or multilayered fabric.

In specific embodiment inner non-woven fabric/pad 20 thickness is from 30 grams/m$^2$ to 500 grams/m$^2$ and it is non swellable and it can be one or multilayered fabric.

In specific embodiment inner non-woven fabric/pad 20 thickness is from 30 grams/m$^2$ to 400 grams/m$^2$ and it is non swellable and it can be one or multilayered fabric.

In specific embodiment inner non-woven fabric/pad 20 thickness is from 30 grams/m$^2$ to 300 grams/m$^2$ and it is non swellable and it can be one or multilayered fabric.

In specific embodiment inner non-woven fabric/pad 20 thickness is from 30 grams/m$^2$ to 200 grams/m$^2$ and it is non swellable and it can be one or multilayered fabric.

In specific embodiment inner non-woven fabric/pad 20 thickness is from 30 grams/m$^2$ to 100 grams/m$^2$ and it is non swellable and it can be one or multilayered fabric.

In specific embodiment inner non-woven fabric/pad 20 thickness is from 10 grams/m$^2$ to 80 grams/m$^2$ and it is non swellable and it can be one or multilayered fabric.

In specific embodiment inner non-woven fabric/pad 20 thickness is from 30 grams/m$^2$ to 800 grams/m$^2$ and it is a swellable and it can be one or multilayered fabric.

In specific embodiment, the adhesive area 21 use a pressure sensitive adhesive that are sticky or tacky to the slight touch of the finger, with light touch of the finger on the surface of the polymeric film 19 is sufficient to adhere Appod™ to the surface of the skin.

In specific embodiment, the adhesive area 21 use a pressure sensitive adhesive over 100% of the Appod™.

In specific embodiment, the adhesive area 21 use a pressure sensitive adhesive from 70 to 100% area of the Appod™.

In specific embodiment, the adhesive area 21 use a pressure sensitive adhesive from 50 to 70% area of the Appod™.

In specific embodiment, the adhesive area 21 use a pressure sensitive adhesive from 20 to 50% area of the Appod™.

In specific embodiment, the pressure sensitive adhesive used in the Appod™ is from the polyarylates (arlylates), polyisobutylene (PIB) and polydimethylsiloxane (silicone) family of adhesives.

Figure 22:
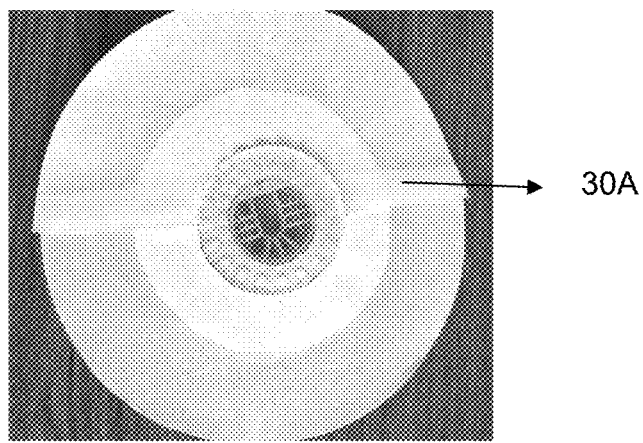
FIG. 22 is an image showing release liners on both the side of the Appod™.

In some embodiments, the Appod™ has two release liners one on the top and one on the bottom on the Appod™, the two release liners provides the structural integrity for the Appod™ and easy of application to consumers. The skin contact adhesive layer of the Appod™ is adhered to the release liner 30A at the bottom prior to use, once the release liner in removed, the Appod™ adheres to the skin site of application. After the Appod™ is adhered, the top release liner will be removed to have the structural integrity of the thin polymeric layer based on the polyurethane player film, this is illustrated in FIG. 22.

In some embodiments, the Appod™ has two release liners one on the top and one on the bottom on the Appod™ will have a design or a product name on it.

In some embodiments, the inner inner non-woven fabric 20 can be non-adherent gauze in a gauze-based dressing, made of cellulose acetate and coated with petrolatum, non-adherent sponge gauze impregnated with PHMB (Polyhexamethylene Biguanide), knitted cellulose acetate fabric and impregnated with a specially formulated petrolatum emulsion, Hydrocolloids dressings containing polymers held in suspension plus gel-forming agents (methylcellulose, pectin, gelatin, polyisobutylene), alginate dressings, hydrogel dressing.

In some embodiment the, the inner non-woven fabric 20 can have thickness of 30 grams/m$^2$ to 700 grams/m$^2$.

In some embodiments, the Outer polymeric fabric layer 19 has a weight of between about 10 g/m$^2$ to about 400 g/m$^2$.

In some embodiments, the Outer polymeric fabric layer 19 has a weight of between about 30 g/m$^2$ to about 280 g/m$^2$.

In some embodiments, the Outer polymeric fabric layer 19 has a thickness between about 0.001 mm to 25 mm.

In some embodiments the inner non-woven fabric layer 20 is composed of spunlace non-woven made up of viscose, polyester, polypropylene, Tenel, wood pulp, cotton, nylon and microfiber or the combination of these materials.

In some embodiments, the Outer polymeric fabric layer 19 has a thickness between about 0.01 mm to 2.0 mm.

The outer polymer fabric layer 19 is from the list of synthetic polymers includes elastomers, i.e., polybutadiene, hydrin rubber, polysiloxane, silicone rubber, nitrile polymer, acrylonitrile, butyl rubber, styrene-butadiene rubber, Styrene-isoprene block copolymers, neoprene polymers, etc. Among other synthetic polymers are polyvinyl alcohol (PVA), polyvinyl chloride (PVC), polyurethane, polyethylene, polypropylene, polyacrylate, polyamide, polyurea, polyvinyl pyrrolidone, polymethyl methacrylate (PMMA), epoxy polymers, etc.

In some embodiments the adhesive can be any one or the combination pressure sensitive adhesives or non-pressure sensitive adhesive. Examples of suitable pressure sensitive adhesives include a natural rubber-based adhesive, a silicone-based adhesive, a synthetic rubber based adhesive, a styrene block copolymer-based adhesive, a polyvinyl ether-based adhesive, a poly(methyl acrylate)-based adhesive, or a polyolefin-based adhesive.

In some embodiments of the present disclosure also include a release liner.

In some embodiments, the THADS™ system uses "Hands free" approach by pumping the "ready to act" solution from the Air less container into the applicator and the pumped solution can be applied to the part of the treatment area using the sponge tip, the same ready to act solution can be used by applying the Appod™ and the solution can be pumped into the Appod™ and can be used to treat extended treatment time.

In specific embodiment of the invention an improved container system that is a child resistant, delivers the exact dose of the drug into the applicator and the drug from the applicator can be applied to the treatment area without using the hand.

In some embodiments, the drug product used in THADS™ Drug product includes solvent enhancers that increase the penetration by swelling the drug pathways and fluidizing the lipids on the way of permeation through epidermis skin layers. Polar pathways are swelled by water, alcohols (Methanol, Ethanol, Isopropyl alcohol), alkyl methyl sulfoxides (e.g., dimethyl sulfoxide (DMSO)), dimethylacetamide, dimethylformamide, pyrrolidones (2-pyrrolidone, N-methyl, 2-pyrrolidone), laurocapram (azone) and miscellaneous other solvents including propylene glycol, glycerol, silicone fluids and isopropyl palmitate.

In some embodiments, the drug product used in THADS™ drug product includes surfactants Cationic surfactants cetyltrimethylammonium bromide, sodium lauryl sulfate (SLS) and diacetyl sulfosuccinate, and dodecyl methyl sulfoxide, the anionic surfactant, nonionic surfactants, pluronic F127 and pluronic F68 and the amphoteric surfactant, N-dodecyl-N,N-dimethyl betaine.

In some embodiments THADS™ drug product consist natural constituents capable of behaving as permeation enhancers like bile acid salts, oleic and lauric acids, propylene glycol-oleic acid and 1,4-butane diol-linoleic acid, urea, 4-decyloxazolidin-2-one, N, N-dimethyl-m-toluamide, calcium thioglycolate, eucalyptol, di-o-methyl-β-cyclodextrin, soybean casein, imidic cyclic urea, cyclopentadecalactone, cyclodextrins, L-menthol, eucalyptus, peppermint and ylang-ylang essential oils, isopropyl myristate, limonene and honey.

In some embodiments, the drug product (solution, suspension, emulsion, gel, and creams) used in THADS™ includes nanosized particles that enhance the solubility and skin permeation.

In specific embodiments treating various acute localized skin disease conditions like topical pain, surgical pain, infection, Acne, Psoriasis, Shingles, Dermatitis, Skin Cancer, Eczema, Rosacea, and drugs that are highly toxic in nature or highly potent and sensitizing in nature and for administering drug for systemic administration for human and animals. The THADS™ uses the drugs in ready to act condition, and the drug can be taken exact dose with the metered dose in the Airless dispenser container, it can be applied to skin with the applicator sponge very smoothly to the affected area and the Appod™ will keep the drug in one place for longer time, consistent drug permeability and prevents adhering to cloths and improved patient compliance and efficacy of the topical drugs. These findings have led to the completion of the present invention.

Nasal applicator: In specific embodiments, the topical analgesic includes at least one of or the combination of drugs in its topical formulation: Diclofenac sodium, Piroxicam, Acetaminophen, Buprenorphine, Fentanyl, Bupivacaine, menthol, trolamine salicylate, camphor, capsaicin, lidocaine HCl, lidocaine, cannabinoids, propofol and methyl salicylate.

In specific embodiments method of treating using Appod™ for various acute and chronic systemic disease conditions like Chronic pain, Essential Hypertension, Cancer, ADHD disorder, Dementia, Major depression disorder, Hypogonadism, Bladder muscle dysfunction, Diabetes, osteoporosis, Flu, Arthritis, obesity, and Alzheimer's disease.

In specific embodiments the Appod™ materials can be sterilized by various means such as autoclaving or gamma radiation or by Ethylene oxide and used for open wounds and surgeries.

In specific embodiments the THADS™ product solution or suspension can be filled in a unit dose container made of polyethylene, polypropylene, glass using a Form Fill Seal technology and this unit dose container can be sterilized using autoclaving or ethylene oxide to by Gamma radiation, this product can be used along with sterilized Appod™ on open wounds or surgeries.

In specific embodiments, the topical analgesic includes as stand alone or in combination of: 0.5-20% menthol, 10-30 wt. % trolamine salicylate, 1-15% camphor, 0.01-5 wt. % capsaicin, 4-10% lidocaine, 0.5-5%, Diclofenac sodium, 0.1-10% cannabinoids and 10-30 wt. % methyl salicylate.

In specific embodiments, the topical analgesic includes the systemic analgesic: Oxycodone, Morphine, Fentanyl, Hydromorphone, Oxymorphone, tramadol, methadone, Duloxetine, pregabalin, Ziconotide.

In specific embodiments, the topical analgesic includes an emulsifier.

In specific embodiments, the topical analgesic includes the emulsifier polysorbate 60, laureth-4, potassium cetyl sulfate, cetyl alcohol, cetearyl alcohol, stearyl alcohol, glyceryl stearate, propylene glycol, polyglyceryl-6 laurate, ceteareth-20, PEG-100 stearate, sodium lauroyl lactylate, myristyl myristate, carbomer, polysorbate 80, polawax, sorbitan stearate, gum Arabic, brassica alcohol, cabomer 980 QD, sodium stearate, polyhydroxystearic acid, PEG-150 distearate, glyceryl oleate, emulsifying wax, glyceryl monooleate, phospholipids, polyoxyethylene alkyl ethers, polyoxyethylene, castor oil derivatives, sorbitan fatty acid esters, polyoxyethylene stearates, polyoxylglycerides, polysorbate, sorbitan esters, lecithin, or any combination thereof.

In some embodiments the outer polymer fabric layer 19 has several functions. It serves as a barrier between pressure sensitive adhesive 26 and hold or acts as pod for the readily active drug products such as solution, suspension, emulsion foam etc. or a pod like silicone pod that holds the ready to act solution or sustained acting solution or suspension, The outer polymer fabric layer 19 also protects the treatment site from contamination during the treatment period, has high moisture vapor transmission rate to allow the skin to perspire, protects the content from water while taking bath.

The outer polymer fabric layer 19 of Appod™ is thin, highly flexible, or deformable, water-impervious, or water pervious or substantially impervious to external fluids, yet breathable. In some embodiments, in some embodiments a second or multiple polymeric fabric layer can be adhered or blended to the outer polymer fabric layer 19 and these layers are water-impervious, or substantially impervious to external fluids. In general, the thickness of outer polymer fabric layer 19 is between about 15 to about 300 microns ("um"), preferably between about 80 to about 200 µm and most preferably, about 150 µm to achieve the forming and flexing characteristics desired.

In some embodiments, the polymeric materials used in outer polymer fabric layer 19 are conformable to the contours of the body, and flexible so as to permit free movement of the body part wearing an Appod™ outer polymer fabric layer 19 is very lightweight, and may be elastic (elastomeric) in character. It can be a woven or nonwoven fabric, a film, or a foam. Preferred polymeric materials useful in forming the wound cover 20 could include polyolefin (such as polyethylene), polyurethane, and polyvinylchloride. Other examples of backings include, but are not limited to, non-woven, woven, or knitted fabrics such as cotton, polyester, polyurethane, rayon, and the like.

A polyethylene film may be used as outer polymer fabric layer 19. However, particularly effective results can be achieved with stretchable, elastomeric films formed of polyurethane, which has the further advantage of gas (including water vapor) transmissibility. In addition, outer polymer fabric layer 19 may be made from other polyolefins, vinyl polyethylene acetate, textile non-woven fabrics, rubber, tissue paper, plastic netting, adsorbent pads, or other materials known in the adhesive article art.

In some embodiments, outer polymer fabric layer 19 is substantially transparent. The Appod™ may be particularly desirable to protect small wounds, such as non-bleeding cuts and the like, without visible bandages. In other embodiments, outer polymer fabric layer 19 is substantially translucent. In still other embodiments, outer polymer fabric layer 19 is substantially opaque. An opaque outer polymer fabric layer 19 can serve to hide the wound from view. In other embodiments, such as for use in children's wound Appod™, the outer polymer fabric layer 19 may be decorated. Decorations include color or colors, decals, printed messages, or cartoons. The decoration serves the dual purpose of hiding the wound site from view, as well as providing entertainment for the wearer of the Appod™

Again, outer polymer fabric layer 19 has disposed thereon a pressure sensitive adhesive 26 arranged and configured to adhere to mammalian skin during use. Adhesive 26 comprises at least one colloidal absorbent component dispersed therein. The colloidal absorbent component used may be any substance that has a good performance in this utilization. Preferred colloidal absorbent components include hydrocolloids, such as, sodium carboxymethylcellulose, pectin, xanthan gum, polysaccharides, sodium or calcium alginates, chitosan, seaweed extract (carrageenan), polyaspartic acid, polyglutamic acid, hyaluronic acid or salts and derivatives thereof, among others. polyesters, polyethylenes, polypropylenes, polystyrenes, polyvinylchloride, and a polyethylene terephthalate/ethylene vinyl acetate laminate.

Hydrocolloids, such as sodium carboxymethylcellulose and pectin, among others, are agents that form gels as soon as they come into contact with the bodily fluids from the wound. When used in adhesive bandages, these hydrocolloids are combined with elastomers and/or adhesives. Preferably, the wound cover provides a humid environment but without saturation, cicatrisation, which is a situation suitable for acceleration of the healing.

In some embodiment the content of the pressure-sensitive adhesive in Appod™ is preferably 5 to 30% % by mass, for example, based on the total mass of the adhesive layer, more preferably 10 to 20% by mass, and further preferably 5 to 15% by mass.

The adhesive substance used in the flexible substrate of the present invention may, for example, be any suitable adhesive substance. Preferably, the adhesive substance is a medical grade adhesive, such as acrylic based pressure sensitive adhesives (PSAs), rubber based pressure sensitive adhesives, silicone pressure sensitive adhesives, mixtures thereof, or the like. Examples of polymeric rubber bases include one or more of styrene-isoprene-styrene polymers, styrene-olefin-styrene polymers including styrene-ethylene/propylene-styrene polymers, polyisobutylene, styrene-butadiene-styrene polymers, polyisoprene, polybutadiene, natural rubber, silicone rubber, acrylonitrile rubber, nitrile rubber, polyurethane rubber, polyisobutylene rubber, butyl rubber, halobutyl rubber including bromobutyl rubber, butadiene-acrylonitrile rubber, polychloroprene, and styrene-butadiene rubber.

Examples of the acrylic pressure-sensitive adhesive base include a polymer of an alkyl (meth)acrylate, and a copolymer of an alkyl (meth)acrylate and a comonomer. In this regard, the alkyl (meth)acrylate means an alkyl acrylate, or an alkyl methacrylate. Examples of the alkyl (meth)acrylate include butyl (meth)acrylate, isobutyl (meth)acrylate, hexyl (meth)acrylate, octyl (meth)acrylate, 2-ethylhexyl (meth) acrylate, and decyl (meth)acrylate. The alkyl (meth)acrylates may be used singly or in combinations of two or more thereof.

Adhesive 26 may be any conventional adhesive known for such use, as for example pressure acrylic adhesives, among others. The interfacing adhesive layer is comprised of one or more polymers selected from selected from acrylates, acrylate copolymers, polyisobutylene, silicone, polystyrene butyl rubber, polyethylene vinyl acetate and copolymers thereof, and plasticized polymers Additionally, such an adhesive may contain a resin for increasing adhesion, a cohesion increasing agent, an absorption agent (preferably a polyacrylate superabsorbent, a polyacrylate salt superabsorbent or a mixture thereof), a plasticizer and optionally a pigment. Adhesive 26 may further be configured in discontinuous patterns, arranged in lines, screen, spray or any other which a person skilled in the art understands as discontinuous, composed by an elastomeric base.

The therapeutic or active agent may be selected from any of the various classes of such agents including, but not limited to, analgesic agents, anesthetic agents, anti-anginal agents, antiarthritic agents, anti-arrhythmic agents, antiasthmatic agents, antibacterial agents, anti-BPH agents, anticancer agents, anticholinergic agents, anticoagulants, anticonvulsants, antidepressants, antidiabetic agents, antidiarrheals, anti-epileptic agents, antifungal agents, antigout agents, antihelminthic agents, antihistamines, antihypertensive agents, anti-inflammatory agents, antimalarial agents, antimigraine agents, antimuscarinic agents, antinauseants, antineoplastic agents, anti-obesity agents, antiosteoporosis agents, antiparkinsonism agents, antiprotozoal agents, antipruritics, antipsychotic agents, antipyretics, antispasmodics, antithyroid agents, antitubercular agents, antiulcer agents, anti-urinary incontinence agents, antiviral agents, anxiolytics, appetite suppressants, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, decongestants, diuretics, gastrointestinal agents, genetic materials, histamine receptor antagonists, hormonolytics, hypnotics, hypoglycemic agents, immunosuppressants, keratolytics, leukotriene inhibitors, lipid-regulating agents, macrolides, mitotic inhibitors, muscle relaxants, narcotic antagonists, neuroleptic agents, nicotine, nutritional oils, parasympatholytic agents, sedatives, sex hormones, sympathomimetic agents, tranquilizers, vasodilators, vitamins, and combinations thereof.

Suitable therapeutically active proteins and Biological drugs include fibroblast growth factors, epidermal growth factors, platelet-derived growth factors, macrophage-derived growth factors such as granulocyte macrophage colony stimulating factors, ciliary neurotrophic factors, tissue plasminogen activator, B cell stimulating factors, cartilage induction factor, differentiating factors, growth hormone releasing factors, human growth hormone, hepatocyte growth factors, immunoglobulins, insulin-like growth factors, interleukins, cytokines, interferons, tumor necrosis factors, nerve growth factors, endothelial growth factors, osteogenic factor extract, T cell growth factors, tumor growth inhibitors, enzymes and the like, as well as fragments thereof.

The therapeutic or active agent may be selected from any of the various classes of biological drugs for example, an antibody, a cytokine, a vaccine, a fusion protein or a growth factor. In a preferred embodiment, the medication is a TNF alpha. inhibitor, insulin, a TNF fusion protein, or a recombinant TNF binding protein, such as infliximab, anti-TNF dAb, golimumab, adalimumab, etanercept The active agent(s) also can be administered with olaparib, bevacizumab, paclitaxel, altretamine, capecitabine, cyclophosphamide, etoposide, gemcitabine, ifosfamide, irinotecan, doxorubicin, melphalan, pemetrexed, topotecan, or vinorelbine, Cisplatin, mechlorethamine, chlorambucil, cyclophosphamide, ifosfamide, melphalan, streptozocin, carmustine, lomustine, busulfan Triazines: dacarbazine, temozolomide, thiotepa, altretamine fulvestrant, tamoxifen, toremifene, clomifene, raloxifene, mifepristone, ulipristal acetate, aglepristone, lilopristone and onapristone bicalutamide, flutamide, nilutamide anastrozole, exemestane, letrozole, megestrol acetate Estrogens Gonadotropin-releasing hormone, leuprolide, goserelin Estradiol, Norethindrone, Drospirenone, Ethinyl Estradiol, Conjugated d Estrogens and Medroxyprogesterone.

Active agent(s) can also be administered with anesthetics including ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and/or phenazopyridine.

The present application also includes methods for treating a patient suffering from a condition such as allergy, ADHD, diabetes, epilepsy, pain, inflammation, nausea, convulsions, muscle spasms, depression, and shingles comprising administering THADS™ Appod™ as described below. The specific formulation of the Silicone dome, non-woven fabric and adhesive material may be varied depending upon the condition(s) being treated, as can the location of application of the THADS™ Appod™.

EXAMPLES

Example 1

Example 1 illustrates the THADS™ formulation efficacy, ready to act for fast onset of its effect, patients' compliance and its method for treatment and comparative analytical test data of the marketed products. Lidocaine 4% Topical solution for pain relief. ACTIVE INGREDIENT: THADS™ Lidocaine 4.0%.

TABLE 4

| Ingredients | % Composition |
| --- | --- |
| Lidocaine USP | 4 |
| Ethanol | 10 |
| Dimethyl Sulfoxide | 10 |
| Propylene Glycol | 10 |
| Hydroxy Propyl Methylcellulose | 0.2 |
| Purified water USP | 45.8 |
| Glycerin | 20 |

The in vitro dissolution was carried out using jacketed Franz diffusion cell and maintained the temperature at with 32° C. during this study, 3.0-micron nylon membrane was used, 30:70 ratio of the Ethanol: Purified water was used as dissolution medium, 12 mL of the dissolution medium was used, 800 rpm of the stirrer RPM was set during the study, the samples solution was replaced at each and every time point. The withdrawn samples were tested using HPLC.

Figure 23:
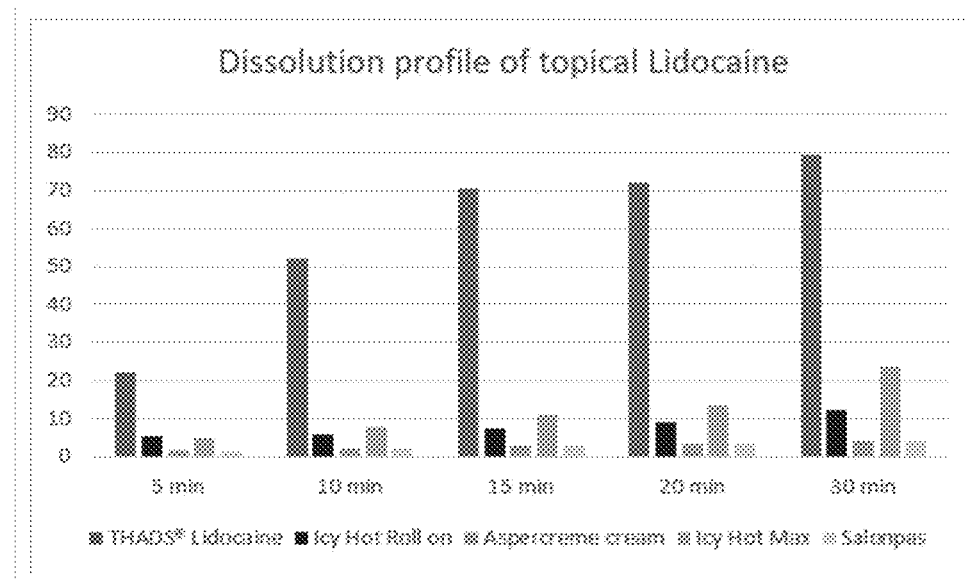
FIG. 23 is a bar graph of the dissolution profile of topical lidocaine.

Using the above test procedure, the THADS™ Lidocaine and the marketed product was tested, and the result are shown in the table 5 and in graphical format at FIG. 23.

a) Fast Onset Time:

Dissolution data from the Table 5 and FIG. 23, indicates the THADS™ lidocaine releases faster around 70% in 15 minutes compared to 7.4%, 2.8%, 10.9% and 3.1% respectively for the currently marketed products. This shows that THADS™ product is faster onset and in "Ready to act" state compared to the marketed products that were tested.

Dissolution profile of the THADS™ Lidocaine in Appod™ versus marketed Icy Hot Lidocaine patch.

TABLE 6

| | % of drug dissolved | | | | |
|---|---|---|---|---|---|
| | 5 min | 10 min | 15 min | 20 min | 30 min |
| THADSTM Lidocaine | 22 | 52.1 | 70.5 | 72.2 | 79.3 |
| Icy Hot Roll on | 5.2 | 5.6 | 7.4 | 8.9 | 12.3 |
| Aspercreme cream | 1.9 | 2.2 | 2.8 | 3.2 | 4 |
| Icy Hot Max cream | 4.8 | 8 | 10.9 | 13.6 | 23.7 |
| Salonpas cream | 1.3 | 2.1 | 3.1 | 3.5 | 4.3 |

| | % Drug dissolved | | |
|---|---|---|---|
| | 5 min | 10 min | 15 min |
| Icy Hot patch | 6.3 | 7.9 | 74.8 |
| THADSTM Lidocaine | 85 | 96.0 | 96.2 |

TABLE 6

| | % Drug dissolved | | |
|---|---|---|---|
| | 5 min | 10 min | 15 min |
| Icy Hot patch | 6.3 | 7.9 | 74.8 |
| THADSTM Lidocaine | 85 | 96.0 | 96.2 |

Data from Table 6 that used the following dissolution method to test the THADS™ Lidocaine in Appod™ versus the marketed Icy Hot Patches in 5 minutes by testing dissolution using USP Apparatus 5 (paddle over disk method), with purified water as the medium volume, 200 mL per vessel. The temperature is maintained at 32±0.5° C. a distance of 25±2 mm between the paddle blade and the surface of the disk assembly. The rotation speed was set at 50 rpm. THADS™ Lidocaine in Appod™ had released 85% of drug in 5 minutes interval than the 6.3% of the marketed Icy Hot Patches, this show the THADS™ Appod™ has rapid onset. The lower dissolution rate of the marketed product is due to the drug added with the adhesive in the patches, that hold the drug from releasing faster.

All the marketed transdermal products Transdermal Scop™, Secuado™, Butrans™, Catapres-TTS™, Estraderm™, Climara™, Vivelle™, Duragesic™, Sancuso™, Daytrana™, Nitrodur™, Minitran™, Oxytrol™, Excelon™, Neupro™, Emsam™, Androderm™ Nioderm™, Zecuity™, Qutenza™, Flextor™, Lidoderm™ Salonpas™, Aspercreme™, Biofreeze™, Icy Hot™ patches all has the drug mixed with adhesive and adhesives covers the entire patches size that is adhering to the skin.

THADS™ system is very effective for when used standalone using the sponge applicator and the Appod™ and it will provide a rapid onset of action.

b) High Efficacy of THADS™ System

Figure 24:
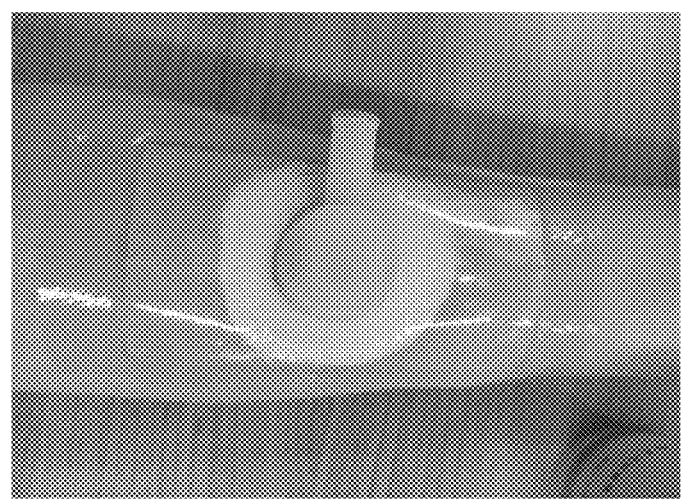
FIG. 24 is a photograph showing an Initial THADS™ Appod™ was added with 4% Lidocaine topical solution through the inlet of the silicone dome, shows the spreading of solution through the non-woven fabric.
Figure 25:
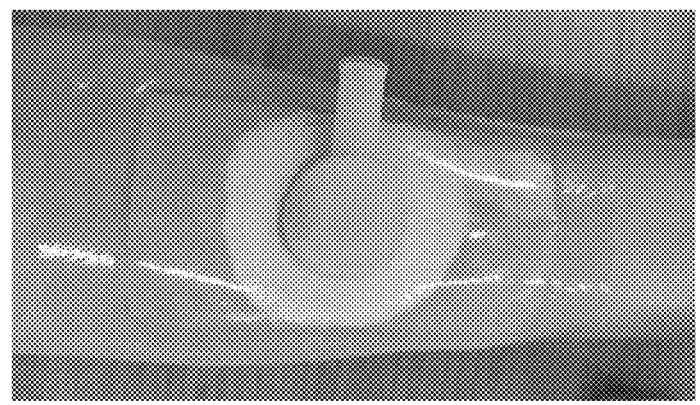
FIG. 25 is a photograph showing 1st hour THADS™ Appod™ with 4% Lidocaine topical solution and 1% Hydrocortisone solution.
Figure 26:
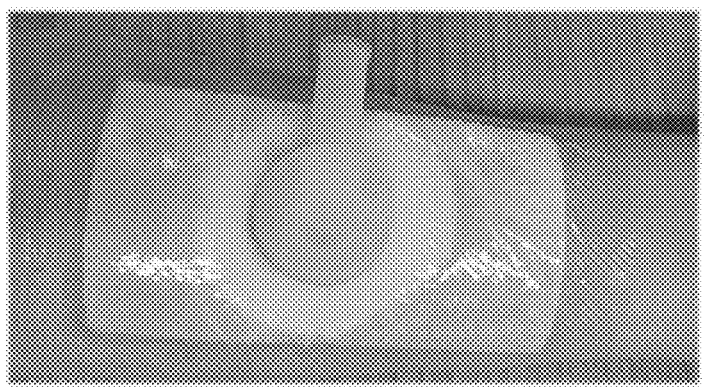
FIG. 26 is a photograph showing 6th hour THADS™ Appod™ with 4% Lidocaine topical solution and 1% Hydrocortisone solution.
Figure 27:
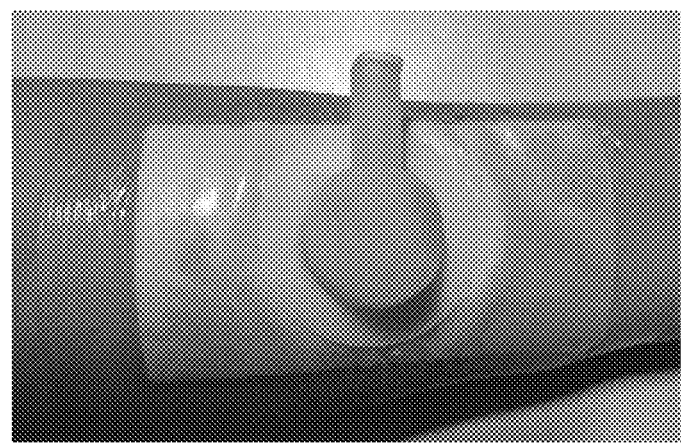
FIG. 27 is a photograph showing 12th hour THADS™ Appod™ with 4% Lidocaine topical solution and 1% Hydrocortisone solution.
Figure 28:
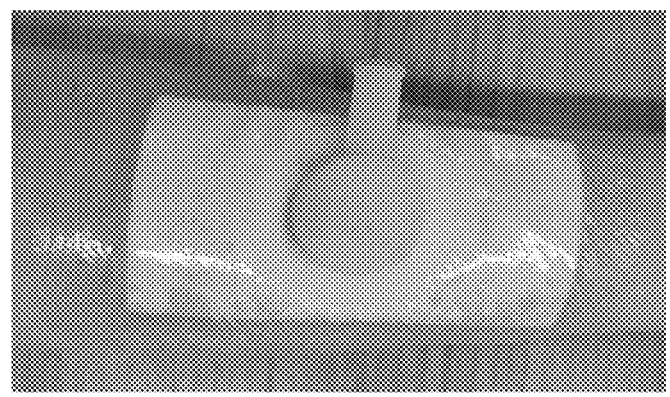
FIG. 28 is a photograph showing 24th hour THADS™ Appod™ with 4% Lidocaine topical solution and 1% Hydrocortisone solution.

FIG. 24 illustrates Appod™ administered with THADS™ lidocaine product and shows the initial time, when the 6 mL (240 mg of Lidocaine) was administered through the inlet of Appod™, THADS™ lidocaine 4% product spread across the Appod™ through the non-woven fabric intended for the treatment area, after 1 hours the FIG. 25 shows the Lidocaine spread throughout the Appod™ and it is wet across the area of the Appod™. FIG. 26 shows the lidocaine spread throughout the Appod™ at 6th hour and it is wet across the area of the Appod™ and shows little dry area on the top left corner. FIG. 27 shows the lidocaine spread throughout the Appod™ at 12th hour and it is wet across the area of the Appod™ and shows little more dry area on the top left corner. FIG. 28 shows the lidocaine spread throughout the Appod™ at 24th hour and it is still wet and shows more dry area on the top left corner. This pictures illustrate, by applying 240 mg of Lidocaine into the inlet as 6 mL solution, it spread itself to the treatment area without using the hand and also due to the presence of the non-woven fabric and due to the presence of the top layer of the Polyurethane film layer it breaths and protect the non-woven from drying rapidly and due to the THADS™ Lidocaine is aqueous based and the once administrated THADS™ product can duration of action for 24 hours. This demonstrate "Hands free application" of a topical product and also cloths can be worn on the Appod™ without getting soiled or interfering with the drug applied on to the skin and enhances the patient compliance.

c) Low Dose and High Efficacy:

The Over-the-counter topical pain marketed product Salonpas a lidocaine 4% patch contains 560 mg of drug/patch (10), directions indicate apply to affected area not more than 3 to 4 times daily (i.e., per day it requires 1680 mg to 2240 mg of lidocaine drug) and Aspercreme another marketed pain reliver path includes lidocaine 4% patch contains 246 mg/patch, Directions indicate apply to affected are not more than 3 to 4 times daily. i.e. per day it requires 738 mg to 984 mg of lidocaine, compared to 240 mg of lidocaine using THADS™ solution and THADS™ Appod™, it shows the improved and enhanced efficacy of the THADS™ system.

d) Patient Compliance: Adhesion Issues with the Marketed Transdermal Patches

A commonly reported issue with topical patch products including the 5% lidocaine hydrogel patch is adhesion. FDA Adverse Events Reporting System found that for the lidocaine patch (Lidoderm), about 70% of concerns reported regarded poor product adhesion.

FDA adverse events reporting system 9 FAERS public dashboard. Data as of Dec. 31, 2018 [cited 2019 Feb. 13].

Figure 29:
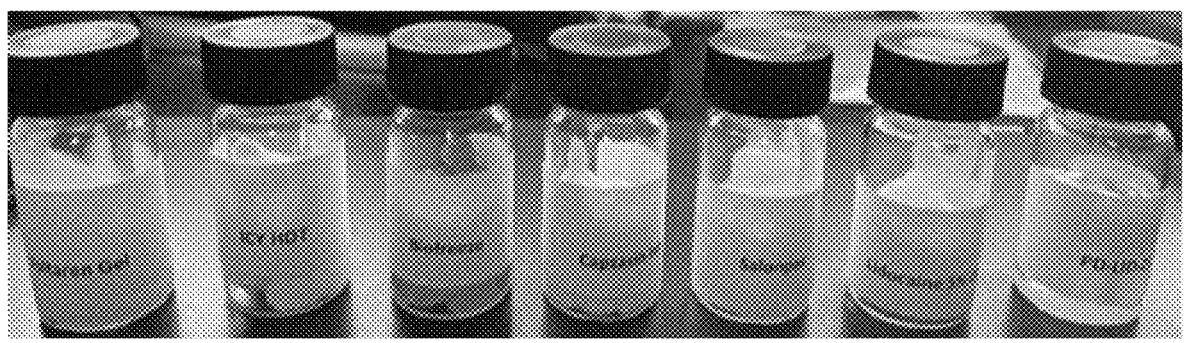
FIG. 29 is a photograph illustrating is marketed topical products for temporary pain relief in a bottle at normal positon.
Figure 30:
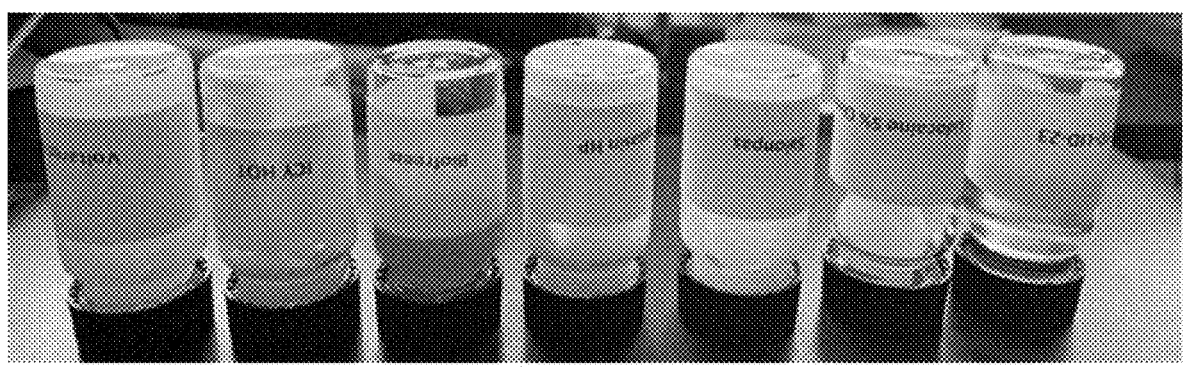
FIG. 30 is a photograph of marketed topical products for temporary pain relief in a bottle at upright positon.

THADS™ Appod™ from FIGS. 24-28 demonstrates its adherence to skin for 24 hours without any leakage or bursting or cold flow or any partial loss of adhesion or lifting at the edges in response to daily activities. This is due to the design of 3 cms of adhesion on the borders and the flexibility of the Polyurethane film.

e) Effect of Cold Conditions on Topical Products:

The currently marketed topical products (Table 2) like ointment and creams uses a vehicle or base to hold the drug and when rubbed at the skin it will melt and leave the drug for the treatment, but when exposed to cold conditions the vehicle becomes hard and thick in consistency and may not release the drug in cold conditions. This was demonstrated below using the marketed topical temporary pain relief products of various formulation like creams, ointments. When the creams and ointment were at upright position at room temperature in a bottle as shown in FIG. 29, after two hours of upright position and when it is inverted after 2 hours, the creams and ointment slowly moved or slide down easily as illustrated in FIG. 30.

Figure 31:
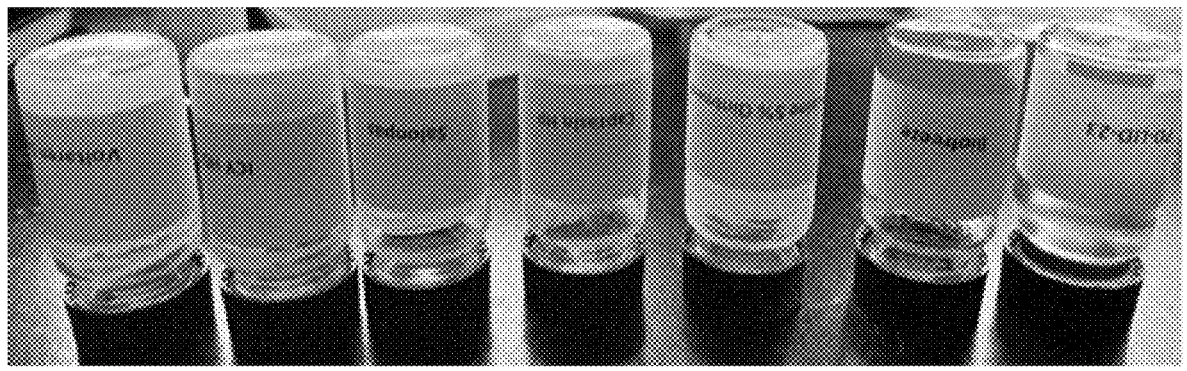
FIG. 31 is a photograph of marketed topical products for temporary pain relief in a bottle at upright positon after exposing it to 2 hours at refrigerator conditions.

When the marketed products of creams and ointment stored at refrigerated conditions for 2 hours and inverted, there is no movement of the products to its bottom, the creams and ointments became thicker and more viscous during cold conditions, this shows that these products may not work in cold conditions, during winter states like Minnesota, Michigan, Illinois, New York, and other Northern states gets colder and typical topical product may not work effectively. Whereas the THADS™ Lidocaine PD-IID-23 on the right corner in FIG. 31 remained as solution and it will work in old conditions.

The invention is very much required to relieve pain in cold regions of Minnesota, New York, New Jersey, and Northeastern States. The THADS™ ready to act will work in the same pattern in hot, warm, and cold conditions with is very unique to the marketed topical products.

Example 2

Example 2 illustrates the THADS™ formulation its method for treatment using multi-model treatment and comparative analytical test data of the marketed products. Lidocaine 4% Topical solution for pain relief. ACTIVE INGREDIENT: THADS™ Diclofenac sodium 1.0%.

TABLE 7

| Ingredients | % Composition |
|---|---|
| Diclofenac sodium | 1 |
| Ethanol | 10 |
| Dimethyl Sulfoxide | 45.5 |
| Propylene Glycol | 10 |
| Hydroxy Propyl Methylcellulose | 0.2 |
| Purified water USP | 13.3 |
| Glycerin | 20 |

The in vitro dissolution was carried out using jacketed Franz diffusion cell and maintained the temperature at with 32° C. during this study, 3.0-micron nylon membrane was used, 30:70 ratio of the Ethanol: Purified water was used as dissolution medium, 12 mL of the dissolution medium was used, 800 rpm of the stirrer RPM was set during the study, the samples solution was replaced at each and every time point. The withdrawn samples were tested using HPLC.

0.5 grams of the marketed Volaren gel was added first followed by 0.5 g of Aspereme cream was added and the dissolution was performed in Franz diffusion cell and the results are shown in Table 7.

TABLE 7

Dissolution profile of marketed combination
Diclofenac sodium and Lidocaine topical products
% of drug Dissolved

|  | 5 min | 10 min | 15 min | 20 min |
|---|---|---|---|---|
| Voltaren gel | 3.2 | 5.6 | 11.8 | 12.3 |
| Aspercreme cream | Did not show much release | | | |

0.5 mL of Lidocaine 4% solution from example 1 was used first followed by 0.5 mL of the Diclofeanc 1% solution form example 2 was added and the dissolution was performed in Franz diffusion cell and the results are shown in Table 8.

TABLE 8

Dissolution profile of THADS ™ combination
Diclofenac sodium and Lidocaine topical products
% of drug dissolved

|  | 5 min | 10 min | 15 min | 20 min |
|---|---|---|---|---|
| THADS ™ Diclofenac | 16.3 | 34.7 | 40.4 | 74.2 |

TABLE 8-continued

Dissolution profile of THADS ™ combination
Diclofenac sodium and Lidocaine topical products
% of drug dissolved

|  | 5 min | 10 min | 15 min | 20 min |
|---|---|---|---|---|
| THADS ™ Lidocaine | 2.8 | 13.5 | 25.7 | 73.5 |

Dissolution profile on Table 7, the combination of the marketed product does not show much release and the among the two drugs added, the Aspercreme cream did not show any release at all. This multimodal treatment is not feasible with the marketed product using the conventional ointment and creams.

Dissolution profile on Table 8, the combination of the THADS™ product shows both the drug was released considerably at 20 minutes, the release of both the drug is not interfered and with the release of 74.2% THADS™ Diclofenac and 73.5% of THADS™ lidocaine it shows, THADS™ product can be administered for a rapid onset of action and also a successful method of multi-modal treatment in topical treatment and this system will deliver multiple drug at the same time in "ready to act state".

Example 3

The application of transdermal patches is not free from disadvantages. In fact, irritant contact dermatitis (ICD) provoked by the adhesive, the active principle or the excipients may often appear, and also allergic contact dermatitis (ACD), consequent to sensitization to the administered active principles (7).

The side effects of the application of the transdermal system are primarily dues to 1) API irritation, some of the drug included in the transdermal system can cause irritation. 2) Transdermal system composed of occlusive backing polymer, which will not allow the system to breathe and also the formulation does not water in it, so it causes the dryness of the skin and causes the skin irritation 3) the adhesive in the transdermal system, most transdermal patches the adhesives are mixed with the drug in a form of matrix, the adhesive from the patches causes the irritation.

Figure 32:
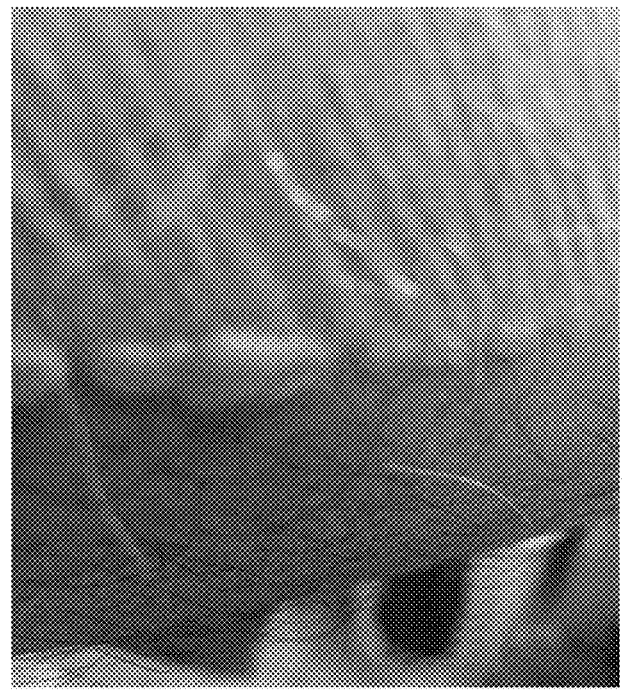
FIG. 32 is a photograph showing blisters and a rash on the skin with Polyurethane dressing.
Figure 33:
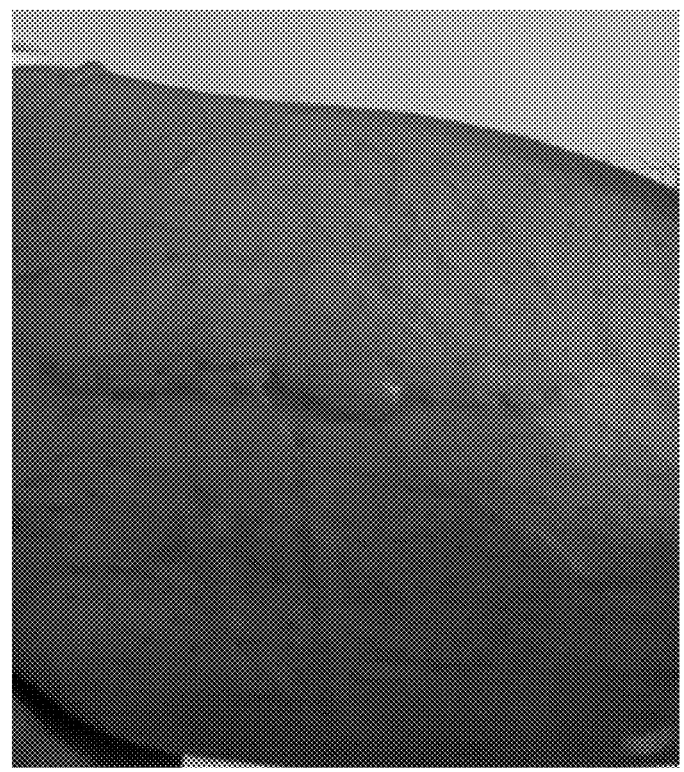
FIG. 33 is a photograph showing blisters and a rash on the skin with after 24 hours of Polyurethane dressing removed.

The primary component that causes the skin irritation is from the adhesives. FIGS. 32 and 33 illustrate the blisters that form a Polyurethane film from Nexcare Tegaderm of size 4 in×4¾ in sterile dressing after 24 hours of applying to the skin. FIG. 32 shows a blister and rash on the skin with marketed Polyurethane dressing on the hand. FIG. 33 shows a blister formed on the skin after applying marketed Polyurethane dressing for 24 hours.

Lidocaine 4% Topical solution for pain relief. ACTIVE INGREDIENT: THADS™ Hydrocortisone 1.0%.

TABLE 9

| Ingredients | % Composition |
|---|---|
| Hydrocortisone | 1 |
| Ethanol | 12 |
| Dimethyl Sulfoxide | 30 |
| Propylene Glycol | 26 |
| isopropyl myristate | 0.2 |
| Purified water USP | 12.7 |
| Glycerin | 18 |
| Tween 80 | 0.1 |

FIG. 22 illustrates the THADS™ Appod™, which has a silicone dome to pump in the THADS™ product for treatment, the pumped solution spread throughout the nonwoven fabric and the Polyurethane fabric hold the Appod™ in the treatment area for the desired period.

THADS™ system has the Polyurethane film, which is highly breathable also the silicone dome in the appod has an inlet, which allows the skin to breathe and the THADS™ products is not mixed with adhesive and the Topical drug products that contains high amount of water in the formulation compared to marketed transdermal patches (which has high drug load and negligible amount of water) and also THADS appod contains adhesive in the periphery of the appod, which is very less of adhesive area compared to the marketed transdermal patches keeps the skin under the appod moist and breathable and prevents the skin irritation.

In some cases, the 0.5 mL of the hydrocortisone 1% solution in example 3 can be added into the Appod™ along with the drug product intended for treatment can be added, which prevent and eliminated the skin irritant contact dermatitis (ICD), this is a unique method of treatment of topical drug delivery system that prevents or eliminate irritant contact dermatitis (ICD).

Example 4

Example 4 illustrates the THADS™ formulation efficacy, and its method for treatment. Lidocaine 4% Topical solution with inorganic salts to recover of the muscle cramps after workout. ACTIVE INGREDIENT: THADS™ Lidocaine 4.0%.

TABLE 10

| Ingredients | % Composition |
| --- | --- |
| Lidocaine USP | 40 |
| Ethanol | 10.0 |
| Dimethyl Sulfoxide | 10.0 |
| Propylene Glycol | 10.0 |
| Sodium Chloride | 0.9 |
| Magnesium Sulphate | 1.0 |
| Purified water USP | 43.1 |
| Strontium Nitrate | 1.0 |
| Glycerin | 20.0 |

THADS™ Lidocaine topical products with inorganic salts includes Sodium chloride, Magnesium Sulphate and Strontium Nitrate is dissolved in 40% of water and these dissolved salts helps recovery during cramps and muscle fatigue after the workout. Appod™ of FIG. 22 is used, the non-woven fabric if of 12 cms diameter and it is applied after or during workout and added 6 ml of solution this helps to recover from muscle fatigue.

Example 5

Shingles usually appears on the side of the chest and back, but it can also occur on the face. On the face. The rash is usually painful, itchy, or tingly. These symptoms may precede rash onset by several days, The rash develops into clusters of vesicles. New vesicles continue to form over three to five days and progressively dry and crust over. They usually heal in two to four weeks.

Figure 34:
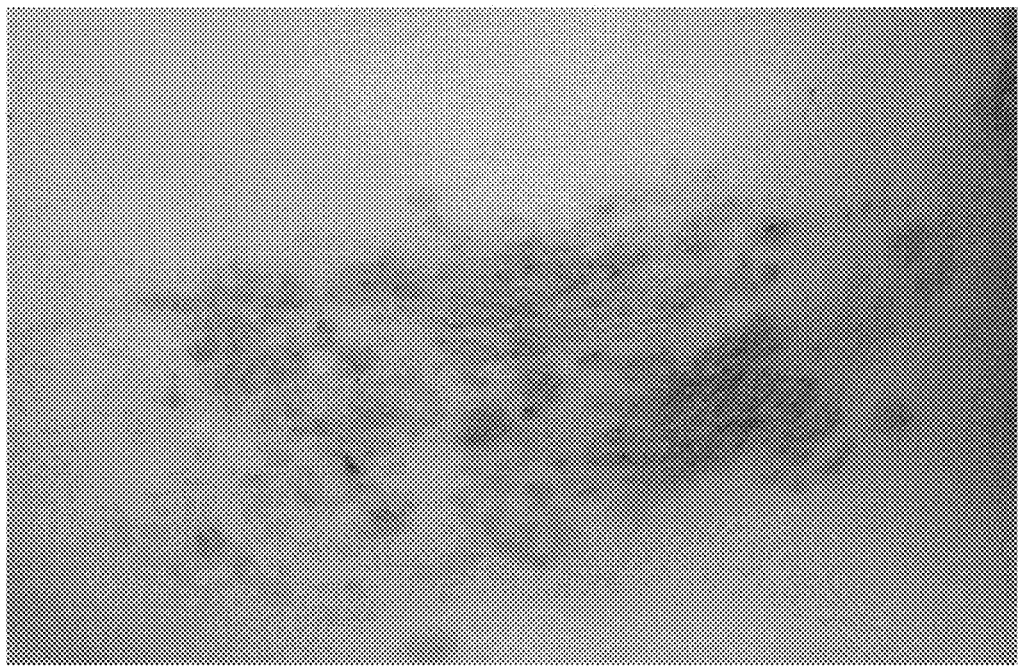
FIG. 34 is a photograph of images of the shingles in chest.

FIG. 34 is a picture of a shingles rash, and it very painful and itchy, and it is impossible to wear cloths when the rash is on the chest and back due to the itchiness and pain and the blisters. The current treatment involves oral antiviral medication followed by Lidocaine ointment or cream or transdermal patches. The pain may be a constant, dull, or burning sensation and its intensity can vary from mild to severe. One may experience sharp stabbing pains from time to time, and the affected area of skin will usually be tender. Current Treatment: FDA approved drug for the treatment of Shingles.

TABLE 11

| Description | Drug | Dosage form | |
| --- | --- | --- | --- |
| Antiviral medicines: Reduces viruses' ability to replicate | Acyclovir | Tablet, capsule, suspension, cream, and ointment | 800 mg every 4 hours orally, 5 times daily for 7 to 10 days |
| | Valacyclovir | Caplet & Suspension | 1 gram 3 times a day |
| | Famciclovir | Tablet | 500 mg three times daily for seven days. |
| Local anesthetic: Blocks pain at and near the site where it's given | Lidocaine | Topical solution, ream, ointment and transdermal patches | No more than one-half tube, approximately 17 g to 20 g of ointment or 850 mg to 1000 mg lidocaine base, should be administered in any one day |
| Analgesic: Relieves pain and reduces inflammation | Diclofenac | Tablets | 100 mg orally once, then 50 mg orally every 8 hours as needed |
| | | Topical gel | Apply the gel (4 g) to the affected area 4 times daily |
| | Naproxen | Tablets, oral suspension | not to exceed 1250 mg/day |
| | Ibuprofen | Tablets | |

Current treatment of shingles requires minimum of three drugs i.e., Antiviral, Analgesic & Anti-inflammatory and continuous local anesthetic administered simultaneously to treat shingles.

Shingles is impossible to treat shingles as a topical treatment with current FDA approved drugs products:

Option #1: If Acyclovir is applied as topical ointment or cream, it is impossible to apply diclofenac gel or the lidocaine topical cream on top of the acyclovir ointment, so this option is not possible, if acyclovir ointment is applied as topical product, diclofenac can be taken orally, but lidocaine can't be taken topically to relieve from itchiness.

Option #2: If Diclofenac topical solution is applied then it is impossible apply Acyclovir ointment and Lidocaine cream or ointment on top of the Diclofenac topical product.

Option #3: If Lidocaine topical cream or the transdermal patches can be applied and the Ayclovir and diclofenac can be taken a soral tablets.

It is impossible to treat shingles with topical treatment that contains antiviral, analgesic and local anesthetic.

Example 6—THADS™ Shingles Treatment

Example 6 illustrates the THADS™ formulation efficacy, and its method for treatment.

Method of Treatment:

Appod™: Apply Appod™ as shown in FIG. 22 to the rashes and blister or to the area of treatment, circular with inner non-woven fabric is 12 cms diameter with 40 gsm/m$^2$ with no adhesive and with outer polymeric layer with 16 cms diameter and has adhesive at boundary of 4 cms and a silicone dome inlet, this appod can hold 12 mL of solution.

After applying the appod add on pump from the THADS™ airless container following drug products:

Example 5: THADS™ acyclovir: 3 mL+THADS™ Diclofenac Sodium 3 ml and THADS™ Lidocaine from example #1 of 6 mL (from FIGS. 24-28 indicates 6 mL of Lidocaine can treat for 24 Hours) This total 12 mL is administered once, if needed additional 1 or 2 ml of THADS Lidocaine can be applied if needed into the appod.

TABLE 14

| Description | Current Option | THADS System |
|---|---|---|
| 100% Topical treatment Drug Dose/day | No | Yes |
| Acyclovir | 4800 mg | 150 mg |
| Diclofenac | 200 mg | 60 mg |
| Lidocaine | 800 mg | 240 mg to 320 mg |
| Dose administration | Multiples times a day | Once a day |
| Effectiveness | Lidocaine in ointment or cream or transdermal patch can't be applied between the blisters | Lidocaine ready to act solution can easily spread through the non-woven fabric and it will be close contact with blisters |
| Clinical significance | Drug -drug interaction is possible between the drug when administered oral route which is absorbed into systemic circulation | Drug- drug interaction is not possible with topical drug delivery system |
| Management of Shingles | Pain and Itchiness will occur during the consecutive dose regimen and cloths can't be worn | Pain and Itchiness is well managed as the ready to act drug will be in constant touch with rashes and blister for 24 hours and Appod protects the rash and blisters, cloths can be worn without any issue |

ACTIVE INGREDIENT: THADS™ Acyclovir 5.0%

TABLE 12

| Ingredients | % Composition |
|---|---|
| Acyclovir | 5.0 |
| Ethanol | 8.0 |
| Dimethyl Sulfoxide | 26.0 |
| Propylene Glycol | 12.0 |
| Sodium Lauryl Sulphate | 0.25 |
| Cetosteryl alcohol | 0.4 |
| Purified water USP | 29.5 |
| Glycerin | 20.0 |

ACTIVE INGREDIENT: THADS™ Diclofenac Sodium 2.0%

TABLE 13

| Ingredients | % Composition |
|---|---|
| Diclofenac sodium | 2.0 |
| Ethanol | 10.0 |
| Dimethyl Sulfoxide | 45.5 |
| Propylene Glycol | 12.0 |
| Purified water USP | 15.5ci |
| Glycerin | 15.0 |

The THADS™ system makes the Singles treatment very effectively compared to the conventional treatment in which, the drug is taken orally, the drugs get absorbed systemically and high doses are required along with its side effects, compared to the doses of the drugs used in THADS™ system is very low. With the THADS system it is very convenient to treat the shingles at the local/topical site and with THADS appod dose adjusted is flexible and it can be once a day.

THADS™ system is an example of method of treatment that acts locally to cure the shingles rather than conventional uses of systemic drugs, low dose of drugs will be used as it uses local topical approach and due to rapid onset of action, this system is very conveniently used for multimodal drug approach and with use of Appod the cloths and bed will not get soiled and this provides high patient compliance.

According to the present invention, a pharmaceutical product and the treatment of topical disease for local treatment or for systemic treatment. More specifically, a pharmaceutical solution, appod a THADS™ system for the prevention and/or treatment of various topical disease and drug intended for systemic administration can administered hand free, fast onset of action, provide exact dose, highly efficacious and high patient compliance.

The efficiency of transdermal drug delivery systems using patches depends often on the rate of absorption of water from the skin and dissolve the active drug from the transdermal matrix and diffusion rate of the active substance through the skin, which on one hand depends on the active substance and its solubility and the water from the skin and dissolving the drug on the other hand the amount of water from the skin entering into the matrix and dissolve the drug varies from human being to human being, and also from the body area the patch is applied to. The constructions of the patches known from prior art usually try to control these dependencies, but the efficiency is not achieved.

It is an object of the present invention to provide a topical delivery system for an which avoids the draw backs known from the prior art. It is a further object of the present invention to provide a THADS technology which is able to administrate the topical drug delivery hands free and delivery drugs, very efficaciously with high patient compliance to a subject over a period of time in a consistent and controllable way.

While the present disclosure has been shown and described herein, it will be obvious to those skilled in the art that such aspects are provided by way of example only. Numerous variations, changes, and substitutions will now occur to those skilled in the art without departing from the disclosure. It should be understood that various alternatives to the aspects of the disclosure described herein may be employed in practicing the disclosure. It is intended that the following claims define the scope of the disclosure and that methods and structures within the scope of these claims and their equivalents be covered thereby.

Any discussion of references cited in this description of the Previous Art merely summarizes the disclosures of the cited references and Applicant makes no admission that any cited reference or portion thereof is relevant prior art. Applicant reserves the right to challenge the accuracy, relevancy and veracity of the cited references.

REFERENCES

1. TRANSDERMAL DRUG DELIVERY: PRINCIPLES AND OPIOID THERAPY LYN MARGETTS, FRCA, RICHARD SAWYER, FRCA FIPP CONTINUING EDUCATION IN ANAESTHESIA CRITICAL CARE & PAIN, VOLUME 7, ISSUE 5, OCTOBER 2007, PAGES 171-176.
2. FELDMAN S R, CAMACHO F T, KREJCI-MANWARING J, CARROLL C L, BALKRISHNAN R. ADHERENCE TO TOPICAL THERAPY INCREASES AROUND THE TIME OF OFFICE VISITS. J AM ACAD DERMATOL. 2007; 57:81-83. DOI: 10.1016/J.JAAD.2007.04.005. [PUBMED]
3. OLIVEIRA C., GAIO A. R., LOBO J. M. S., DE ALMEIDA I. F. M., TEIXEIRA A. DEVELOPMENT AND VALIDATION OF A NOVEL QUESTIONNAIRE FOR ADHERENCE WITH TOPICAL TREATMENTS IN PSORIASIS (QATOP) AM. J. CLIN. DERMATOL. 2017; 18:571-581. [PUBMED] [GOOGLE SCHOLAR]
4. KREJCI-MANWARING J., MCCARTY M. A., CAMACHO F., CARROLL C. L., JOHNSON K., MANUEL J., BALKRISHNAN R., HARTLE J., FLEISCHER A., FELDMAN S. R. ADHERENCE WITH TOPICAL TREATMENT IS POOR COMPARED WITH ADHERENCE WITH ORAL AGENTS: IMPLICATIONS FOR EFFECTIVE CLINICAL USE OF TOPICAL AGENTS. J. AM. ACAD. DERMATOL. 2006; 54: S235-S236. DOI: 10.1016/J.JAAD.2005.10.060. [PUBMED] [CROSSREF]
5. KREJCI-MANWARING J, TUSA M G, CARROLL C, CAMACHO F, KAUR M, CARR D, FLEISCHER A B, JR, BALKRISHNAN R, FELDMAN S R. STEALTH MONITORING OF ADHERENCE TO TOPICAL MEDICATION: ADHERENCE IS VERY POOR IN CHILDREN WITH ATOPIC DERMATITIS. J AM ACAD DERMATOL. 2007; 56:211-216.
6. MEDICATION THERAPY MANAGEMENT IN DERMATOLOGY: A CALL TO ACTION, ARTICLE, APRIL 2021, J DERMATOL TREAT. AMARIS N GEISLER, CAITLIN G. PURVIS, DIEM-PHUONG D DAO
7. CONTACT DERMATITIS DUE TO TRANSDERMAL THERAPEUTIC SYSTEMS: A CLINICAL UPDATE ROMITA PAOLO,[1] FOTI CATERINA,[1] CALOGIURI GIANFRANCO,[2] CANTORE STEFANIA,[3,4,5] BALLINI ANDREA,[3,4] DIPALMA GIANNA,[3,4,5] AND INCHINGOLO FRANCESCO[3],
8. HTTPS://WWW.NCBI.NLM.NIH.GOV/PMC/ARTICLES/PMC6017304/
9. HTTPS://DAILYMED.NLM.NIH.GOV/DAILYMED/
10. HTTPS://DAILYMED.NLM.NIH.GOV/DAILYMED/DRUGINFO.CFM?SETID=4F3A438C-F378-4D2A-A95C-58E56CF1E797

What is claimed is:

1. A topical product system comprising:
an airless metered pump product container or a container with a modified nozzle configured to hold an applicator wand or tube for unit dose or multiple dose application, wherein the airless metered pump product container or container holds a topical pharmaceutical product in a "ready to act state;"
wherein a product outlet in the modified nozzle connects and disconnects a first end of the wand of the applicator, and the wand directs the topical pharmaceutical product to a second wand end that is connected to an applicator sponge tip;
wherein the sponge tip is configured to connect to or disconnect from the wand;
wherein the wand is flexible and has a straight or bent shape, and is 0.01 inch to 30 inches in length;
wherein the applicator sponge tip includes a soft sponge that holds the topical pharmaceutical product;
wherein the wand is configured to be disconnected from a first end of the modified nozzle after pumping the topical pharmaceutical product;
wherein the applicator sponge tip is configured to be disconnected from the wand and the modified nozzle inserted into an opening of an adhesive application pod device such that the topical pharmaceutical product is pumped as one dose or multiple doses into the device;
wherein the device comprises a rate controlling layer that includes a non-woven fabric or coated woven fabric, an interior, and an outer skin barrier seal ring configured to house the topical pharmaceutical product within the device interior, and an adhesive layer;
wherein the device is configured to spread and deliver the topical pharmaceutical product continuously for one application or for one day or more; and
wherein the device includes a polymer dome comprising silicone with an opening, and wherein the dome includes a duckbill valve to prevent backflow of the topical pharmaceutical product.

2. The system of claim 1, wherein the topical pharmaceutical product is a liquid, or is a nanosized or micronized suspension, gel or an emulsion with a viscosity of 5000 centipose (cP) or less, wherein the topical pharmaceutical product releases above 15% in 15 minutes using a diffusion cell using a 3.0 micron nylon filter at 800 rpm stirring rate and a volume of 10 ml dissolution medium of water: ethanol 70:30;
wherein the topical pharmaceutical product does not freeze or change mobility or rheological properties when stored at a refrigerated condition for 2 hours between 35° F. and 38° F.

3. The system of claim 2, wherein the topical pharmaceutical product has a load below 190 or 180 grams, when tested using a Texture analyzer, and using a probe at the following settings, Test Type: Compression, Test Target: Distance with Target value of 15 mm and target load of 10 grams with test speed of 1.0 mm/second.

4. The system of claim 1 wherein the topical pharmaceutical product includes an anti-itch agent, 5 to 90% water, and a skin permeation enhancer.

5. A method of treating a subject with the topical pharmaceutical product, the method comprising:
applying or adhering the device of claim 1 into an area of treatment of the skin;
adding the topical pharmaceutical product to the interior of the device, wherein the topical pharmaceutical product will spread onto the area of treatment of skin and the device will hold the topical pharmaceutical product in place for delivery through the area of treatment of skin via a bottom part of the device that adheres to the skin;

wherein the topical pharmaceutical product is pumped or added from a syringe or from a single unit dose or from the container of claim 1 after removing the applicator sponge tip;

whereby the device adheres to the area of treatment of skin, thereby holding the topical pharmaceutical product in the area of treatment of skin for local and systemic action;

wherein the device is adhered for 1 minute, an hour, 3 hours, one day, or multiple day treatment for months.

6. The method of claim 5, wherein two or more topical pharmaceutical products are administered using the device;

wherein the topical pharmaceutical products each include an active drug that is nano-sized, micro-sized, lipid encapsulated and dispersed evenly for topical application;

wherein the two or more topical pharmaceutical products are each configured to penetrate passively into the area of treatment after applying to the skin;

wherein the device includes multiple interior compartments to administer the two or more topical pharmaceutical products simultaneously in respective compartments for a synergistic effect of the two or more topical pharmaceutical products.

7. The method of claim 6 wherein the device includes a first interior compartment comprising a topical pharmaceutical product with penetration enhancers and skin anti-irritants are added to one compartment of the device and the device includes a second compartment comprises small molecules, peptides, biological drugs, or combinations thereof;

wherein the penetration enhancers are pumped continuously onto the area of treatment of skin for a fixed number of hours, followed by pumping a desired dose of the small molecules, peptides, and biological drugs, or combinations thereof from the second compartment pod;

wherein the subject is suffering from one or more of atopic dermatitis, shingles, psoriasis, eczema, nausea vomiting, cancer of the central nervous system, pain disorder, gastrointestinal disorder, or acute disease conditions.

8. The method of claim 5, wherein the topical pharmaceutical product is not touched by hand and is pumped into the device for systemic and local use three times a day or once a day application, for 2-day application, for 3-day application, for 4-day application, for 5-day application, for 6-day application, for weekly application and up to one month application;

wherein the device includes an integrated solution reservoir that can delivers the topical pharmaceutical product through a battery operated miniature pump configured to deliver 1 microliter/min to 1000 microliter/min through a programmable logic system for drug treatment for 1 hour, 4 hours, 8 hours, 12 hours, 1 day, 2 days, 3 days, 4 days, 5 days, 6 days, 7 days, or months using local action and systemic action.

9. The method of claim 5 for the treatment of a systemic disease or condition, the method comprising adhering the device in one place or more than one place on a body of the subject, wherein the one place or more than one place is selected from both arms, both thighs, both arms and both thighs, stomach, back, or thigh.

10. The method of claim 5, wherein the device loaded topical pharmaceutical product releases 40 to 90% of the topical pharmaceutical product 5 minutes after delivery to a subject.

11. The method of claim 5, wherein the odor of the topical pharmaceutical product is reduced compared to delivery without the device; and wherein the system minimizes, prevents, or does not cause irritant contact dermatitis (ICD) and blisters after treatment; and wherein hydrocortisone solution or other steroid solution or anti-allergenic solution is added into the device along with the topical pharmaceutical product.

12. The system of claim 1, wherein the wand is connected into the container as snap on mechanism so that the first end is connected to the container and seamless transfer of the topical pharmaceutical product to the second end is enabled;

wherein the wand includes a flow control mechanism on the first end of the wand;

wherein the wand includes a sponge applicator or a leveling mechanism or an opening to deliver the topical pharmaceutical product to the device.

13. The system of claim 1, wherein the topical pharmaceutical product has a load above 1.0 kg or above 5.0 kg when tested using a Texture analyzer, using a probe at the following settings, Test Type: Compression, Test Target: Distance with Target value of 10 mm and target load of 250 grams with test speed of 1.0 mm/second;

wherein a tension of the container prevents back flow of the topical pharmaceutical product from the applicator wand in the upright position.

14. The system of claim 1, wherein the device includes more than one compartment within the interior, wherein each compartment is configured to hold multiple topical pharmaceutical products separately, or one compartment where multiple drugs are added;

wherein the device includes a chamber configured with uncontrolled delivery of the topical pharmaceutical product or controlled delivery of the topical pharmaceutical product over a 6 hour, 12 hour, 24 hour, 72 hour, or 1 week period.

15. The system of claim 1, wherein the topical pharmaceutical solution includes an anti-itching drug selected from antihistamine or steroids, and an antimicrobial drug is coated with anti-itching and antimicrobial drugs.

16. The system of claim 1, wherein the device rate controlling layer comprises a non-woven fabric or woven fabric that is coated with Diphenhydramine HCl or Hydrocortisone to prevent irritation;

wherein the interior of the device holds a volume of 0.1 ml to 50 ml and the device is configured to deliver 0.25 to 25 ml/day of the topical pharmaceutical product;

wherein the topical pharmaceutical product is within the outer skin barrier seal ring, and wherein the outer skin barrier seal ring is soft, flexible and includes an adhesive;

wherein the outer skin barrier seal ring is coated with antibacterial, antiviral or anti itching and anti-irritating drug;

wherein an outer layer of the outer skin barrier seal ring is absorbent to any residual topical pharmaceutical product seeping or leaking out of the barrier seal ring;

wherein the system includes a bag that houses the topical pharmaceutical product and controls the delivery of the topical pharmaceutical product into the device to deliver the drug for treatment for 0.1 hours to 3 months;

wherein the bag is connected to the device using a micro-motor to pump a predetermined amount of the topical pharmaceutical product from the bag to a treatment area.

17. The system of claim 1, wherein the device comprises a silicone or medical grade polymer open dome that includes the duckbill valve, or a silicone or medical grade polymer closed dome that includes the duckbill valve and a micro porous opening or a micro hole at a bottom of the open or closed dome;
   wherein a bottom layer of the device includes a nonirritating adhesive layer applied on to the non-woven or woven fabric, the non-woven or the woven fabric is coated with a drug that prevents irritation to the skin;
   wherein the outer skin barrier seal ring includes ethylene vinyl acetate (EVA) foam or a polymer that is non-absorbent but retains the topical pharmaceutical product within the ring and wherein the ring holds 0.1 mL to 10 mL, and a top layer of the device includes breathable or non-breathable fabric.

18. The system of claim 1, wherein the topical pharmaceutical product includes one or more pain-relieving drugs selected from diclofenac sodium, Ibuprofen, acetaminophen, menthol, camphor, methyl salicylate, naproxen, benzocaine, lidocaine, tetracaine, propofol, meloxicam, piroxicam, gabapentin, pregabalin, corticosteroids, dexamethasone, hydrocortisone, clobetasol, cortisone, magnesium sulphate, sodium chloride, potassium chloride, potassium nitrate, strontium chloride, strontium nitrate, zinc chloride, along with 5 to 95 weight % water.

19. The system of claim 1, wherein the device is prefilled with the topical pharmaceutical product by removing a release liner from the outer skin barrier seal ring to initiate release of the topical pharmaceutical product from the device interior.

\* \* \* \* \*